US008960004B2

(12) United States Patent
Zaghloul et al.

(10) Patent No.: US 8,960,004 B2
(45) Date of Patent: Feb. 24, 2015

(54) SYNCHRONOUS ONE-POLE SURFACE ACOUSTIC WAVE RESONATOR

(75) Inventors: Mona E. Zaghloul, Bethesda, MD (US); Hsu-Cheng Ou, Gaithersburg, MD (US)

(73) Assignee: The George Washington University, Washington, DC (US)

( * ) Notice: Subject to any disclaimer, the term of this patent is extended or adjusted under 35 U.S.C. 154(b) by 660 days.

(21) Appl. No.: 13/075,088

(22) Filed: Mar. 29, 2011

(65) Prior Publication Data

US 2012/0073390 A1   Mar. 29, 2012

Related U.S. Application Data

(60) Provisional application No. 61/387,806, filed on Sep. 29, 2010.

(51) Int. Cl.
| | |
|---|---|
| *G01N 29/12* | (2006.01) |
| *G01N 29/02* | (2006.01) |
| *G01N 29/036* | (2006.01) |
| *H03H 9/64* | (2006.01) |

(52) U.S. Cl.
CPC ............ *G01N 29/022* (2013.01); *G01N 29/036* (2013.01); *H03H 9/6476* (2013.01); *G01N 2291/0256* (2013.01); *G01N 2291/0423* (2013.01)
USPC ............................................... 73/579; 73/580

(58) Field of Classification Search
USPC ..................................... 73/579, 580; 331/154
See application file for complete search history.

(56) References Cited

U.S. PATENT DOCUMENTS

| | | | |
|---|---|---|---|
| 4,065,735 A | 12/1977 | Palfreeman et al. | |
| 4,065,736 A | 12/1977 | London | |
| 4,124,828 A | 11/1978 | Bert | |
| 4,194,171 A | 3/1980 | Jelks | |
| 4,354,166 A | 10/1982 | Grudkowski | |
| 4,387,355 A | 6/1983 | Uno et al. | |
| 4,453,242 A | 6/1984 | Toda | |
| 4,647,881 A | 3/1987 | Mitsutsuka | |
| 4,665,374 A | 5/1987 | Fathimulla | |
| 4,801,836 A * | 1/1989 | Mariani .................... | 310/313 D |
| 5,166,646 A | 11/1992 | Avanic et al. | |
| 5,196,720 A | 3/1993 | Sugai et al. | |

(Continued)

FOREIGN PATENT DOCUMENTS

| | | |
|---|---|---|
| EP | 1 804 059 A2 | 4/2007 |
| WO | WO 92/01931 A1 | 2/1992 |
| WO | 2004012331 A1 | 2/2004 |

OTHER PUBLICATIONS

Buff, et al., "Universal Pressure and Temperature Saw Sensor for Wireless Applications," 1997 IEEE Ultrasonics Symposium, 1997, pp. 359-362, vol. 1, Oct. 5-8, 1997.

(Continued)

*Primary Examiner* — Hezron E Williams
*Assistant Examiner* — Paul West
(74) *Attorney, Agent, or Firm* — Cahn & Samuels, LLP

(57) ABSTRACT

A surface acoustic wave resonator including an input interdigital transducer (IDT), an output IDT, and a pair of gratings with each being spaced from each other by a predetermined distance and attached to a substrate. In at least one embodiment, the distance is equal to one-half of the wavelength of the acoustic wave produced by the input IDT. In a further embodiment, the surface acoustic wave further includes a polymer layer and a biomedical coating covering at least a part of the polymer layer. The surface acoustic wave resonator has uses in the mass sensor and communications fields.

18 Claims, 30 Drawing Sheets

(56) References Cited

U.S. PATENT DOCUMENTS

| | | | |
|---|---|---|---|
| 5,214,338 A | 5/1993 | Tanski | |
| 5,235,233 A | 8/1993 | Yamamoto | |
| 5,265,267 A | 11/1993 | Martin et al. | |
| 5,392,013 A * | 2/1995 | Yamamoto et al. | 333/195 |
| 5,477,098 A | 12/1995 | Eguchi et al. | |
| 5,492,840 A | 2/1996 | Malmqvist et al. | |
| 5,559,483 A | 9/1996 | Kajihara et al. | |
| 5,571,401 A | 11/1996 | Lewis et al. | |
| 6,285,866 B1 | 9/2001 | Lee et al. | |
| 6,336,368 B1 | 1/2002 | Chung et al. | |
| 6,404,101 B1 | 6/2002 | Taniguchi et al. | |
| 6,407,486 B1 | 6/2002 | Kimura et al. | |
| 6,448,064 B1 | 9/2002 | Vo-Dinh et al. | |
| 6,495,892 B2 | 12/2002 | Goodman et al. | |
| 6,518,084 B1 | 2/2003 | Seitz et al. | |
| 6,555,946 B1 | 4/2003 | Finder et al. | |
| 6,580,198 B2 | 6/2003 | Nakano et al. | |
| 6,621,134 B1 | 9/2003 | Zum | |
| 6,627,154 B1 | 9/2003 | Goodman et al. | |
| 6,657,269 B2 | 12/2003 | Migliorato et al. | |
| 6,686,675 B2 | 2/2004 | Koshido | |
| 6,743,581 B1 | 6/2004 | Vo-Dinh | |
| 6,842,091 B2 | 1/2005 | Yip | |
| 6,848,295 B2 | 2/2005 | Auner et al. | |
| 6,861,754 B2 | 3/2005 | Lin et al. | |
| 6,872,902 B2 | 3/2005 | Cohn et al. | |
| 6,877,209 B1 | 4/2005 | Miller et al. | |
| 6,933,808 B2 | 8/2005 | Ma et al. | |
| 6,937,052 B2 | 8/2005 | Tam | |
| 6,937,114 B2 | 8/2005 | Furukama et al. | |
| 6,951,047 B2 | 10/2005 | Tomioka et al. | |
| 6,974,707 B1 | 12/2005 | Barie et al. | |
| 7,170,213 B2 | 1/2007 | Yamanaka et al. | |
| 7,295,089 B2 | 11/2007 | Shibahara et al. | |
| 7,301,423 B2 | 11/2007 | Furuhata et al. | |
| 7,369,014 B1 | 5/2008 | Fehsenfeld et al. | |
| 7,400,219 B2 | 7/2008 | Furuhata et al. | |
| 7,451,649 B2 | 11/2008 | Edmonson et al. | |
| 7,473,551 B2 | 1/2009 | Warthoe | |
| 7,498,898 B2 | 3/2009 | Nakanishi et al. | |
| 7,647,814 B2 | 1/2010 | Nakaso et al. | |
| 7,888,842 B2 * | 2/2011 | Pereira da Cunha et al. | 310/324 |
| 8,018,010 B2 | 9/2011 | Tigli et al. | |
| 2002/0041218 A1 | 4/2002 | Tonegawa et al. | |
| 2002/0068157 A1 | 6/2002 | Wischerhoff | |
| 2003/0231082 A1 | 12/2003 | Takata et al. | |
| 2004/0021403 A1 | 2/2004 | Ayazi et al. | |
| 2004/0048241 A1 | 3/2004 | Freeman et al. | |
| 2004/0070312 A1 | 4/2004 | Penunuri et al. | |
| 2004/0110299 A1 | 6/2004 | Sivavec | |
| 2004/0178698 A1 | 9/2004 | Shimoe et al. | |
| 2004/0189148 A1 | 9/2004 | Yamanaka et al. | |
| 2004/0232802 A1 | 11/2004 | Koshido | |
| 2004/0245891 A1 | 12/2004 | Kawachi et al. | |
| 2005/0017896 A1 | 1/2005 | Klofer et al. | |
| 2005/0029960 A1 | 2/2005 | Roh et al. | |
| 2005/0043894 A1 | 2/2005 | Fernandez | |
| 2005/0131998 A1 | 6/2005 | Takashima | |
| 2005/0242891 A1 | 11/2005 | Ash | |
| 2005/0281210 A1 | 12/2005 | Makino | |
| 2006/0032312 A1 | 2/2006 | Auner et al. | |
| 2006/0131678 A1 | 6/2006 | Yajima et al. | |
| 2006/0197408 A1 | 9/2006 | Chen | |
| 2006/0230833 A1 | 10/2006 | Liu et al. | |
| 2007/0159027 A1 | 7/2007 | Tsai et al. | |
| 2008/0230859 A1 | 9/2008 | Zaghloul et al. | |
| 2009/0114798 A1 | 5/2009 | Tigli et al. | |
| 2009/0124513 A1 | 5/2009 | Berg et al. | |
| 2010/0007444 A1 | 1/2010 | Nordin et al. | |
| 2010/0029226 A1 | 2/2010 | Visser | |

OTHER PUBLICATIONS

Smole, et al., "Magntically Tunable SAW-Resonator," Proceedings of the 2003 IEEE International Frequency Control Symposium and PDA Exhibition Jointly with the 17th European Frequency and Time Forum, 2003, pp. 903-906, May 4-8, 2003.

Pohl, et al., "Wireless Sensing Using Oscillator Circuits Locked to Remote High-Q Saw Resonators," IEEE Transactions on Ultrasonics, Ferroelectrics and Frequency Control, vol. 45, No. 5, pp. 1161-1168, Sep. 1998.

Nomura, et al., "Chemical Sensor Based on Surface Acoustic Wave Resonator Using Langmuir-Blodgett Film," IEEE Transactions on Ultrasonics, Ferroelectrics and Frequency Control, vol. 45, No. 5, pp. 1261-1265, Sep. 1998.

Datta, "Resonators," Prentice Hall, 1986, Ch. 10, pp. 225-239.

Ruby, et al., "Thin Film Bulk Wave Acoustic Resonators (FBAR) for Wireless Applications," 2001 IEEE Ultrasonics Symposium, vol. 1, pp. 813-821, 2001.

Visser, "Surface Acoustic Wave Filters in ZnO-SiO2-Si Layered Structures: Design, Technology and Monolithic Integration with Electronic Circuitry," Ph.D. dissertation, Delft University of Technology, Delft, The Netherlands, Dec. 1989.

Vellekoop, et al., "Acoustic-Wave Based Monolithic Microsensors," Invited, Proc. of 1994 IEEE Ultrasonics Symposium, Cannes, France, 1994, pp. 565-574.

Baca, et al., "Development of a GaAs Monolithic Surface Acoustic Wave Integrated Circuit," IEEE J. Solid-State Circuits, vol. 34, No. 9, Sep. 1999, pp. 1254-1258.

Nordin, et al., "Design and Implementation of a 1 GHz Resonator Utilizing Surface Acoustic Wave," presented at the Int. Sym. Circuits and Systems, Kos, Greece, 2006.

Morgan, "Surface-Wave Devices for Signal Processing," New York: Elesevier Science, 1985, Ch. 4 and 6, pp. 57-105 and 129-155.

van Zeijl, "Fundamental Aspects and Design of an FM Upconversion Receiver Front-End with On-Chip SAW Filters," Ph.D. dissertation, Delft University of Technology, Delft, Netherlands, Feb. 1990.

Datta, et al., "An Analytical Theory for the Scattering of Surface Acoustic Waves by a Single Electrode in a Periodic Array on a Piezoelectric Substrate," J. Appl. Phys., vol. 51, No. 9, pp. 4817-4823, 1980.

Tigli, et al., "Design and Fabrication of a Novel SAW Bio/Chemical Sensor in CMOS," 2005 Proc. IEEE Sensors Conf., pp. 137-140.

Vellekoop, "A Smart Lamb-Wave Sensor System for the Determination of Fluid Properties," Ph.D. dissertation, Delft University of Technology, Delft, the Netherlands, Dec. 1989.

Zhu, et al., "Wet-Chemical Etching of (1120) ZnO Films," Journal of Electronic Materials, Jun. 2004, vol. 33, No. 6, pp. 556-559.

AMIS, "Process Technology," http://www.amis.com/pdf/C5_process_spec.pdf.

Conventor, Inc. "Conventor Ware 2008 Using Conventor Wave," http://www.coventor.com, Mar. 3, 2008.

Cascade Microtech, Inc., "Layout Rules for GHz-Probing," Application Note, http://www.cmicro.com/index.cfm/fuseaction/pg.view/pID/1172IEEE.

IEEE, "Standard Definitions and Methods of Measurement for Piezoelectric Vibrators," ANSI/IEEE Standard 177, New York, NY, May 1966, pp. 1-19.

IEEE, "An American National Standard: Standard on Piezoelectricity," ANSI/IEEE Standard 176, New York, NY, 1988, pp. 1-66.

Iwai, "CMOS Technology for RF Application," Proc. 22nd International Conference on Microelectronics (Miel 2000), vol. 1, No. 1, Serbia, May 14-17, 2000, pp. 27-34.

Hassan, et al., "Impact of Technology Scaling on RF CMOS," IEEE International SOC Conference Proceedings, Sep. 12-15, 2004, Santa Clara, CA, pp. 97-101.

Burghartz, "Tailoring Logic CMOS for RF Applications," VLSI Technology Systems and Applications, 2001, pp. 150-153.

Bingxue, "Challenges in RF Analog Integrated Circuits," IEEE Proceedings 4th International Conference on ASIC, 2001, pp. 800-805.

Iwai, "RF CMOS Technology," IEEE Proceedings Asia-Pacific Radio Science Conference, 2004, pp. 296-298.

Huang, et al., "The Impact of Scaling Down to Deep Submicron on CMOS RF Circuits," IEEE Journal of Solid-State Circuits, 1998, vol. 33, No. 7, pp. 1023-1036.

Steyaert, et al, "Low-Voltage Low-Power CMOS-RF Transceiver Design," IEEE Transactions on Microwave Theory and Techniques, Jan. 2002, vol. 50, No. 1, pp. 281-287.

(56) References Cited

OTHER PUBLICATIONS

Lin, et al, "Micropower CMOS RF Components for Distributed Wireless Sensors," 1998 IEEE Radio Frequency Integrated Circuits Symposium, 1998, pp. 157-160.

Campbell, "Surface Acoustic Wave Devices for Mobile and Wireless Communications," Academic Press, 1998, pp. 114-122.

Tan, et al., "Minmization of Diffraction Effects in Saw Devices using a Wide Aperture," 1986 Ultrasonics Symposium, 1986, pp. 13-17, IEEE.

Nakagawa, "A New Saw Convolver Using Multi-Channel Waveguide," 1991 Ultrasonics Symposium, 1991, pp. 255-258, IEEE.

Green, et al., "Focused Surface Wave Transducers on Anisotropic Substrates: A Theory Developed for the Waveguided Storage Correlator," 1980 Ultrasonics Symposium, 1980, pp. 69-73, IEEE.

Wilcox, et al., "Time-Fourier Transform by a Focusing Array of Phased Surface Acoustic Wave Transducers," J. Appl. Phys. vol. 58, No. 3, Aug. 1985, pp. 1148-1159.

Brooks, et al., "Saw RF Spectrum Analyzer/Channelizer Using a Focusing, Phased Array Transducer," 1985 Ultrasonics Symposium, 1985, pp. 91-95, IEEE.

Wu, et al., "Analysis and Design of Focused Interdigital Transducers," IEEE Transactions on Ultrasonics, Ferroelectrics and Frequency Control, vol. 52, No. 8, Aug. 2005, pp. 1384-1392.

Qiao, et al., "Focusing of Surface Acoustic Wave on a Piezoelectric Crystal," Chin. Pys. Lett., vol. 23, No. 7, 2006, pp. 1834-1837.

Fang, et al., "Saw Focusing by Circular-Arc Interdigital Transducers on YZ-LiNbO3," IEEE Transactions on Ultrasonics, Ferroelectrics, and Frequency Control, vol. 36, No. 2, Mar. 1989, pp. 178-184.

Kharusi, et al., "On Diffraction and Focusing in Anistropic Crystals," Proceedings of the IEEE, vol. 60, No. 8, Aug. 1972, pp. 945-956.

Oezguer, et al., "A Comprehensive Review of ZnO Materials and Devices," Journal of Applied Physics, vol. 98, 2005, pp. 041301-1-041301-103.

Tigli, et al., "A Novel Saw Device in CMOS: Design, Modeling, and Fabrication," IEEE Sensors Journal, vol. 7, No. 2, Feb. 2007, pp. 219-227.

Coventor, "3D MEMS Design Automation & Virtual Fabrication—Coventor" at http://www.coventor.com, printed on Nov. 2, 2010.

Farnell, "Elastice Surface Waves," Surface Wave Filters: Design, Construction, and Use, 1977, pp. 1-53.

Tigli, et al., "Design, Modeling, and Characterization of a Novel Circular Surface Acoustic Wave Device," IEEE Sensors Journal, vol. 8, No. 11, Nov. 2008, pp. 1808-1815.

Tigli, et al., "A Novel Circular SAW (Surface Acoustic Wave) Device in CMOS," IEEE Sensors Journal, 2007, pp. 474-477.

Bender, Florian, et al., "Acoustic Wave-Based Sensors Using Mode Conversion in Periodic Gratings," IEEE Transactions on Ultrasonics, Ferroelectrics and Frequency Control, Nov. 1999, pp. 1497-1503, vol. 46, No. 6.

Campbell, Colin K., "Surface Acoustic Wave Devices for Mobile and Wireless Communications," Applications of Modern Acoustics, 1998, pp. 20-33, 76-82, 114-122, 200-205, 297-298, Academic Press.

Campbell, C. K., et al. "Narrow-Band Filter Design Using a Staggered Multimode SAW Resonator," IEEE Transactions on Sonics and Ultrasonics, Jan. 1985, pp. 65-70, vol. SU-32, No. 1.

Campbell, C. K., et al, "Analysis and Design of Low-Loss Saw Filters Using Single-Phase Unidirectional Transducers," IEEE Transactions on Ultrasonics, Ferroelectrics, and Frequency Control, May 1987, pp. 357-367, vo. UFFC-34, No. 3, IEEE.

Chen, Dong-Pei, et al., "Analysis of Metal-Strip SAW Gratings and Transducers," IEEE Transactions on Sonics and Ultrasonics, May 1985, pp. 395-408, vol. Su-32, No. 3.

Cross, Peter S., et al., "Synchronous IDT SAW Resonators With Q Above 10,000," 1979 Ultrasonics Symposium, 1979, pp. 824-829, IEEE.

Flory, Curt, "Diffraction Minimization in SAW Devices Using Wide Aperature Compensation," IEEE Transactions on Ultrasonics, Ferroelectrics and Frequency Control, Jul. 1988, pp. 498-502, vol. 35, No. 4.

Hartmann, C.S., et al., "Overview of Design Challenges for Single Phase Unidirectional SAW Filters," 1989 Ultrasonics Symposium, 1989, pp. 79-89, IEEE.

Hietala, Susan L., et al., "Dual Saw Sensor Technique for Determining Mass and Modulus Changes," IEEE Transactions on Ultrasonic, Ferroelectrics, and Frequency Control, Jan. 2001, pp. 262-267, vol. 48, No. 1.

Isobe, Atsushi, et al. "Large k2 and Good Temperature Stability for SAW on New Double-Rotated Cut of a-Quartz with Gold Film," 1993 Ultrasonic Symposium, 1993, pp. 323-326, IEEE.

Lehtonen, Saku, et al., "Unidirectional SAW Transducer for Gigahertz Frequencies," IEEE Transactions on Ultrasonics, Ferroelectrics, and Frequency Control, Nov. 2003, pp. 1404-1406, vol. 50, No. 11.

Lehtonen, Saku, et al., "Unidirectional SAW Transducer for GHz Frequencies," 2003 IEEE Ultrasonics Symposium, 2003, pp. 817-820, IEEE.

Naraine, P. M., et al., "Gigahertz SAW Filters on YZ-Lithium Niobate without the Use of Sub-Micron Line Widths," 1984 Ultrasonics Symposium, 1984, pp. 93-96, IEEE.

Nomura, Tooru, et al., "Mass Flow Sensor Using Dual SAW Device," 2007 Frequency Control Symposium, May 29-Jun. 1, 2007, pp. 25-30, IEEE.

Paige, E.G.S., et al., "SAW Reflection from Aluminium Strips on LiNb03," 1981 Ultrasonics Symposium, 1981, pp. 144-147, IEEE.

Saw, C. B., et al., "Improved Design of Single-Phase Unidirectional Transducers for Low-Loss SAW Filters," 1987 Ultrasonics Symposium, 1987, pp. 169-172, IEEE.

Trancrell, R. H., et al., "Acoustic Surface Wave Filters," Proceedings of the IEEE, Mar. 1971, pp. 393-409, vol. 59, No. 3.

Xu, J., et al., "Mass Sensitivity of Dual Mode SAW Delay Lines on AlN/sapphire Structure," Electronics Letters, Oct. 27, 2005, vol. 41, No. 22.

Zhang, Zheng, et al., "A Mass-Loading Effect LiNbO3 SAW Sensor," Proceedings 6th International Conference on Solid-State and Integrated Circuit Technology, 2001, pp. 781-784, IEEE.

Nordin, Anis Nurashikin, et al., "CMOS Surface Acoustic Wave Oscillators," 48th Midwest Symposium on Circuits and Systems, 2005, pp. 607-610, vol. 1, IEEE.

Nordin, Anis Nurashikin, et al., "Modeling and Fabrication of CMOS Surface Acoustic Wave Resonators," IEEE Transactions on Microwave Theory and Techniques, May 20, 2006, pp. 992-1001, vol. 5, No. 5, IEEE.

Yamanouchi, Kazuhiko, "GHz-Range SAW Device Using Nano-Meter Electrode Fabrication Technology," 1994 Ultrasonics Symposium, 1994, pp. 421-428, IEEE.

Drafts, Bill, "Acoustic Wave Technology Sensors," Sensors, Oct. 1, 2000, downloaded from http://www.snesormag.com/sensors/acoustic-ultrasound/acoustic-wave-technology-sensors-936.

Ou, Hsu-Cheng, et al., "Design and Implementation of Parallel-IDT Surface Acoustic Waves (SAW) Low Loss RF Filters," Circuits and Systems, 2009. ISCAS 2009, IEEE International Symposium on/, vol., No., pp. 273-276, May 24-27, 2009.

Puccio, D., et al., "SAW Senors Using Orthogonal Frequency Coding," IEEE Transitions on Ultrasonics, Ferroelectronics and Frequency Control, Feb. 13, 2006, pp. 377-384, vol. 53, iss. 2.

Shen, Jie, et al, "Development of a Surface Acoustic Wave LB Membrane Immunity Sensor," Journal of Tongji Medical University, 2000, vol. 20, No. 1, pp. 20-22.

Soofi, Wafa, "Nanoscale Surface Acoustic Wave Sensors for Early Cancer Detection," 2005 NNIN REU Research Accomplishments, pp. 140-141.

Zaki, A., et al., "Implementation of MEMS-SAW Device on RF Circuits for Wireless Applications," Circuits and Systems, 2007. MWSCAS 2007. 50th Midwest Symposium on/, vol., No., pp. 614-617, Aug. 5-8, 2007 doi: 10.1109/MWSCAS.2007.4488656 URL: http://ieeexplore.ieee.org/stamp/stamp.jsp?tp=&arnumber=4488656&isnumber=4488527.

(56) References Cited

OTHER PUBLICATIONS

Nordin, et al., "CMOS Surface Acoustic Wave Oscillators," IEEE 48th Midwest Symposium on Circuits and Systems, 2005, pp. 607-610.

Yamanouchi, "GHz-Range SAW Device Using Nano-Meter Electrode Fabrication Technology," IEEE Ultrasonics Symposium Proceedings, 1994, vol. 1, pp. 421-428.

Devreux, Vincent, et al., "Synthesis and Biological Evaluation of Cyclopropyl Analogues of Fosmidomycin as Potent Plasmodium falciparum Growth Inhibitors", J. Med. Chem., Mar. 24, 2006, pp. 2656-2660, vol. 49, No. 8.

Silber, Katrin, et al., "AFMoC Enhances Predictivity of 3D QSAR: A Case Study with DOXP-reductoisomerase", J. Med. Chem., Apr. 16, 2005, pp. 3547-3563, vol. 48, No. 10.

Verbrugghen, Thomas, et al., "Synthesis and Evaluation of alpha-Halogenated Analogues of 3-(Acetylhydroxyamino) propylphosphonic Acid (FR900098) as Antimalarials", J. Med. Chem., Jun. 22, 2010, pp. 5342-5346, vol. 53, No. 14.

* cited by examiner

SYNCHRONOUS ONE-POLE SURFACE ACOUSTIC WAVE RESONATOR

This patent application claims the benefit of U.S. Provisional Patent Application No. 61/387,806, filed Sep. 29, 2010, which is hereby incorporated by reference.

I. FIELD OF THE INVENTION

This invention relates to surface acoustic wave devices having applications as mass detectors, filters, oscillators, and in transmitters and/or receivers in communication systems including wireless communication systems.

II. BACKGROUND OF THE INVENTION

The surface acoustic wave (SAW) devices have been used in many applications, such as resonators; replacements for inductance-capacitance (LC) filters; chemical or gas sensors; and radio frequency applications. SAW resonators are used in sensor applications because of their high sensitivity to surface mass perturbations based on the presence of a mass. The changes of the mass on the surface cause changes in phase velocity and center frequency of the waves. These characteristics of SAW resonators can be harnessed for use as biosensors, gas sensors and chemical sensors. S. L. Hietala et al., "Dual SAW sensor technique for determining mass and modulus changes," *IEEE Trans. Ultrason., Ferroelectr., Freq. Control*, vol. 48, no. 1, pp. 262267, January 2001 and F. Bender et al., "Acoustic wave-based sensors using mode conversion in periodic gratings," *IEEE Trans. Ultrason., Ferroelectr., Freq. Control*, vol. 46, no. 6, pp. 1497-1503, November 1999. The operating frequencies of SAW resonators depend on the width of electrodes; however the low insertion loss (<−6 dB) of common existing SAW filter designs limit them to being suitable primarily as radio frequency (RF) or narrowband filters.

In recent years, there has been much research in using SAW resonators as sensors. The applications of SAW resonators include chemical, thermal, pressure or biological areas. These devices sense differences by the interferences of acoustic waves on the piezoelectric surface. These interferences are from the change of total mass on the surface or the path of the transmission line. They cause a decrease in the velocity, center frequency and/or amplitude of acoustic waves. The time of acoustic waves' propagation between input and output transducers is also increased by these interferences. These changes can be sensed by the decrease of the center frequency, propagation loss or the increase of propagating time in the output transducer. A common design for a SAW sensor attracts the substance being measured so that the electrical signals collected at the output interdigital transducer (IDT) are different than the signals without the attracted substance.

Attention has been drawn in recent years to the use of SAW resonators in microfluidic devices. The acoustic waves are mechanical waves, which have motions in the Z direction on the surface. These surface motions typically have approximately 10 Å displacements and allow the SAW resonators to be used as microactuators. The acoustic waves can propagate into the fluid and become an inertial force. This mechanism to drive fluid actions allows the possibility for the SAW resonators being used in pumping, mixing or jetting devices of microfluidic devices.

SAW resonators have been used to design analog electrical filters and to substitute for inductance-capacitance (LC) filters in high-volume TV components, because they have very competitive performance for the price for use in intermediate-frequency (IF) circuit stages. Their operating frequency is typically in the range of 10 MHz to 1 GHz. There was intensive research done early on due to their wide range of applications; however, the SAW technology reached the limit of its low insertion loss (IL). The insertion loss of existing SAW filter designs is smaller than −6 dB (i.e., more negative or less than), which limits the utilization in the IF stages. For the receivers stage in telecommunications, the IF stages, which operate in millivolt signals, can tolerate the high loss of SAW filters. The RF filter circuits, which only have microvolt-level inputs, cannot use SAW filters due to the limitations of the signal-to-noise ratio and insertion loss. There are wider applications of low-loss SAW filters in RF front-end filters and antenna duplexers in communications.

The research and development of SAW resonators is related in the following three fields: (1) the geometry of the metal-film IDTs, (2) piezoelectric substrate, and (3) the wave propagation type. The insertion loss and frequency response characteristics can also be improved from these three factors. In general, the various SAW resonators for communication systems can be categorized into the four types discussed below. The frequencies for mobile and wireless applications typically range from 800 MHz to 2.4 GHz. The SAW filters are used in IF and RF stages in wireless communications. Bidirectional IDTs have uses as the delay lines for oscillators or equalizers, a PN-coded trapped-delay line for CDMA-TDMA systems, delay lines to reduce the multipath interference, fixed frequency reference oscillators, VCOs for first- or second-mixing stages in mobile transceivers, intermediate frequency (IF) filters for mobile receivers, and Nyquist filters. Resonator/filters have uses as fixed frequency and tunable oscillators, resonators for transmitter circuits, RF front-end filters for mobile systems, RF front-end filters for wireless receivers, and high-power antenna duplexers. Unidirectional IDTs have uses as low-loss IF filter for wireless circuits (>−3 dB), RF front-end filters for wireless communications, and multimode oscillators for spread-spectrum communications. Nonlinear operation SAW resonators have use as convolvers for spread-spectrum communications.

III. SUMMARY OF THE INVENTION

The research leading to the embodiments described in this disclosure had a first objective to develop a low-loss and one-pole frequency response for SAW resonators. The insertion loss, which is the receiving power in the output transducer, is typically smaller than −6 dB. One research goal was to achieve a low-loss response (>−3 dB) by improving the performance of SAW as a filter and as a biosensor. The research found that at least one embodiment having a bidirectional SAW resonator on a $LiNbO_3$ piezoelectric substrate could have two-pole frequency response and a low Q factor.

The second objective in the research was to develop at least one embodiment having a SAW mass sensor on a $LiNbO_3$ substrate. When the additional mass is deposited on the surface, it results in a decrease in velocity and center frequency of acoustic waves. This decrease of the center frequency, or frequency shift, was found to linearly relate to the additional mass. A frequency shift, due to the additional mass, can be observed by the low-loss and one-pole response in the output from the output IDT(s). This mechanism allows a synchronous low-loss one-pole SAW resonator to have potential application in sensors; however, it is easier to determine the frequency shifts if the SAW resonator has a one-pole response in the output IDT. The mass sensitivity for at least one embodiment is approximately $8.23e^{12}$ Hz·mm$^2$/g for a 978 MHz SAW mass sensor.

The third objective for this research was to use a SAW mass sensor operational in a liquid-phase environment for mass detection. The acoustic waves are excited by conductive electrodes on the piezoelectric surface, but the signal on these electrodes will short when the SAW resonator is in liquid. In order to protect the electrodes in at least one embodiment, a polymer coating is applied to the surface in order to avoid the short circuit. This polymer-coated SAW mass sensor in part makes it possible to sense antibody-antigen reactions in liquid.

This invention provides a surface acoustic wave resonator including: a substrate; an input interdigital transducer mounted to the substrate, the input interdigital transducer having a plurality of electrode pairs; an output interdigital transducer spaced a distance L from the input interdigital transducer and mounted to the substrate, the output interdigital transducer having a plurality of electrode pairs; a first grating spaced the distance L from the input interdigital transducer and mounted to the substrate; a second grating spaced the distance L from the output interdigital transducer and mounted to the substrate; and wherein the distance L equals $$\frac{\lambda}{2}.$$

In a further embodiment, the substrate includes piezoelectric material. In another embodiment, the substrate is a 128° YX $LiNbO_3$ crystal. In a further embodiment, the input interdigital transducer and the output interdigital transducer have an identical number of electrode pairs; and the first and second gratings each include at least 15 shorted reflectors. In at least one embodiment, the surface acoustic wave resonators of the above embodiment have an insertion loss is between 0 dB and −5 dB. In a further embodiment, the surface acoustic wave resonator further includes: a second input interdigital transducer mounted to the substrate, the second input interdigital transducer having a plurality of electrode pairs; a second output interdigital transducer spaced a distance L from the second input interdigital transducer and mounted to the substrate, the second output interdigital transducer having a plurality of electrode pairs; a third grating spaced the distance L from the second input interdigital transducer and mounted to the substrate; a fourth grating spaced the distance L from the second output interdigital transducer and mounted to the substrate; and wherein the input interdigital transducer, the output interdigital transducer, the first grating and the second grating are aligned along a first path of the acoustic waves generated by the input interdigital transducer, the second input interdigital transducer, the second output interdigital transducer, the third grating and the fourth grating are aligned along a second path of the acoustic waves generated by the second input interdigital transducer, and the first path and the second path are parallel to each other. In a further embodiment, any of the above surface wave resonator embodiments further includes a polymer layer covering the first input interdigital transducer, the first output interdigital transducer, the second input interdigital transducer, the second output interdigital transducer, the first grating, the second grating, the third grating, and the fourth grating; and a biochemical coating over at least a part of the polymer layer.

This invention provides a mass sensor including: a support member, a surface acoustic wave resonator comprising a substrate having piezoelectric material, an input interdigital transducer mounted to the substrate to receive an input electrical signal and transmit a pair of corresponding acoustic waves within the substrate, an output interdigital transducer spaced a distance L from the input interdigital transducer and mounted to the substrate to receive the acoustic waves generated by the input interdigital transducer and transmit an output electrical signal, a first grating spaced the distance L from the input interdigital transducer and mounted to the substrate, a second grating spaced the distance L from the output interdigital transducer and mounted to the substrate, a polymer layer having a bottom surface attached to the input interdigital transducer, the output interdigital transducer, the first grating, and the second grating, and a biochemical coating over at least a portion of a top surface of the polymer layer; a first connector in electrical communication with the input interdigital transducer; and a second connector in electrical communication with the output interdigital transducer; and wherein the distance L equals $$\frac{\lambda}{2}.$$

This invention provides a mass sensor including: a support member; a support structure on which sits the support member; a first acoustic wave resonator and a second acoustic wave resonator, each of which includes a piezoelectric substrate, an input interdigital transducer mounted to the substrate to receive the input electrical signal and transmit a pair of corresponding acoustic waves within the substrate, an output interdigital transducer spaced a distance L from the input interdigital transducer and mounted to the substrate to receive the acoustic waves and transmit a reference output electrical signal, a first grating spaced the distance L from the input interdigital transducer and mounted to the substrate, and a second grating spaced the distance L from the output interdigital transducer and mounted to the substrate; a first connector; a second connector; a third connector; a fourth connector; and a controller electrically connected to the first connector, the second connector, the third connector, and the fourth connector, the controller is capable of transmitting an input electrical signal to the first connector and the third connector and receiving output electrical signals from the second connector and the fourth connector with the difference in frequency in the output electrical signals representing a presence of a mass; and wherein at least one of the first surface acoustic wave resonator and the second surface acoustic wave resonator further includes a well disposed over at least two of the input interdigital transducer, the output interdigital transducer, the first grating, and the second grating; and the support member is connected to the first connector, the second connector, the third connector, and the fourth connector, the support member includes lines electrically connecting the following the input interdigital transducer and the second interdigital transducer of the surface acoustic wave resonator to the first connector, the output interdigital transducer and the second output interdigital transducer of the surface acoustic wave resonator to the second connector, the input interdigital transducer and the second interdigital transducer of the second surface acoustic wave resonator to the third connector, and the output interdigital transducer and the second output interdigital transducer of the second surface acoustic wave resonator to the fourth connector.

Given the following enabling description of the drawings, the apparatus should become evident to a person of ordinary skill in the art.

IV. BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is described with reference to the accompanying drawings. In the drawings, like reference numbers indicate identical or functionally similar elements. The use of cross-hatching and shading within the drawings is not intended as limiting the type of materials that may be used to fabricate or manufacture any embodiment according to the invention.

FIG. 3A illustrates an alternative SAW embodiment according to the invention.

Figure 7:
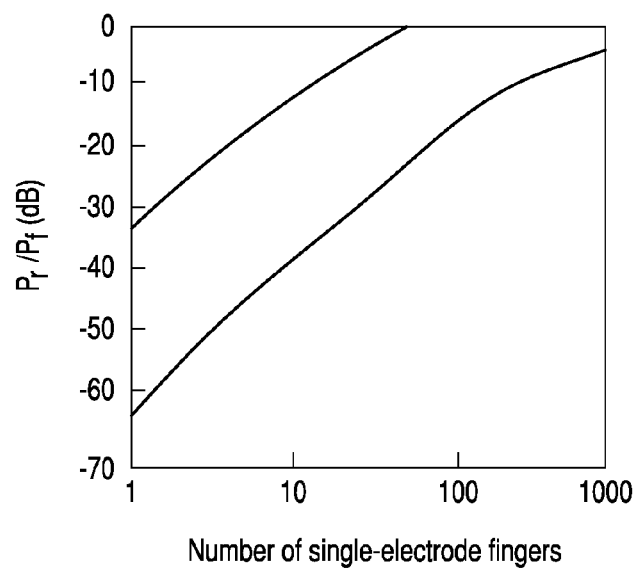

FIG. 7 depicts the ratio of power reflection from the electrodes of the gratings on a 128° YX $LiNbO_3$ substrate and a ST Quartz substrate. The metallization η is 0.5. The power reflected by ten electrodes on the 128° YX $LiNbO_3$ substrate is substantially equal to the same power reflected by 100 electrodes on the ST Quartz.

Figure 8:
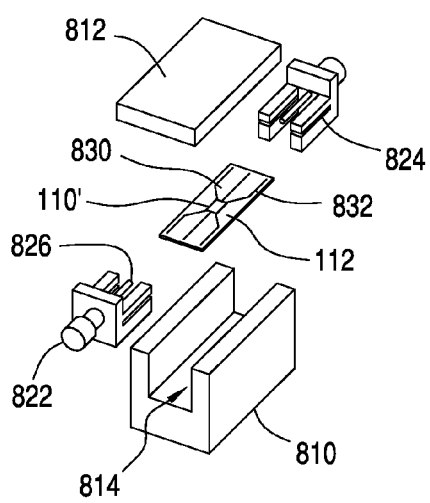

FIG. 8 illustrates an exploded view of a housing embodiment according to the invention.

Figure 9:
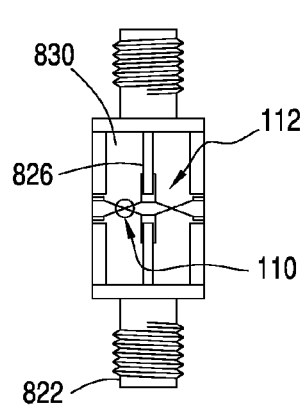

FIG. 9 illustrates a top view of some of the components illustrated in FIG. 8.

Figure 10:
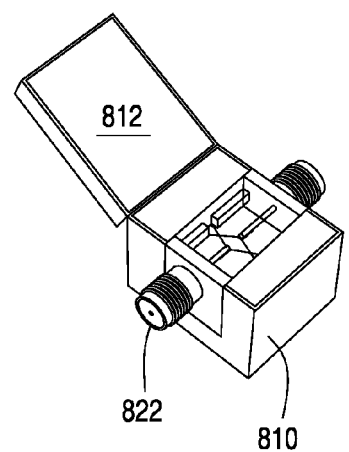

FIG. 10 illustrates a perspective view of an assembled housing of FIG. 8 according to the invention.

Figure 11:
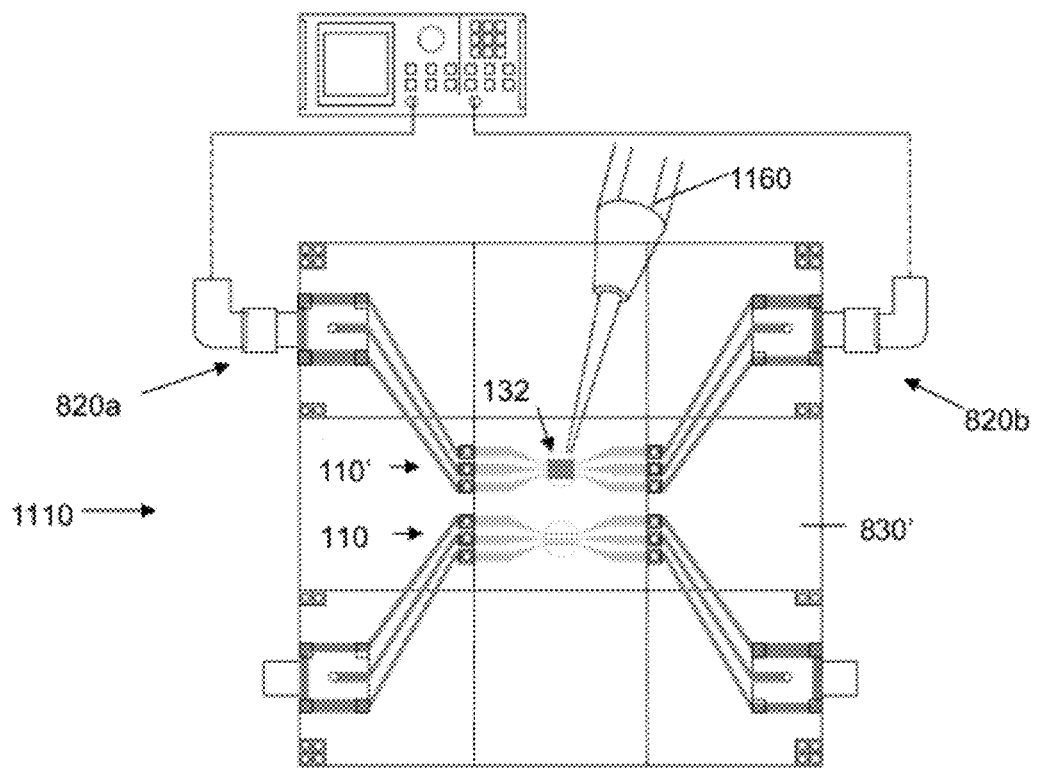

FIG. 11 illustrates another housing embodiment according to the invention showing an example of a configuration of a SAW mass sensor and measurement equipment (depicted as a network analyzer).

Figure 12:
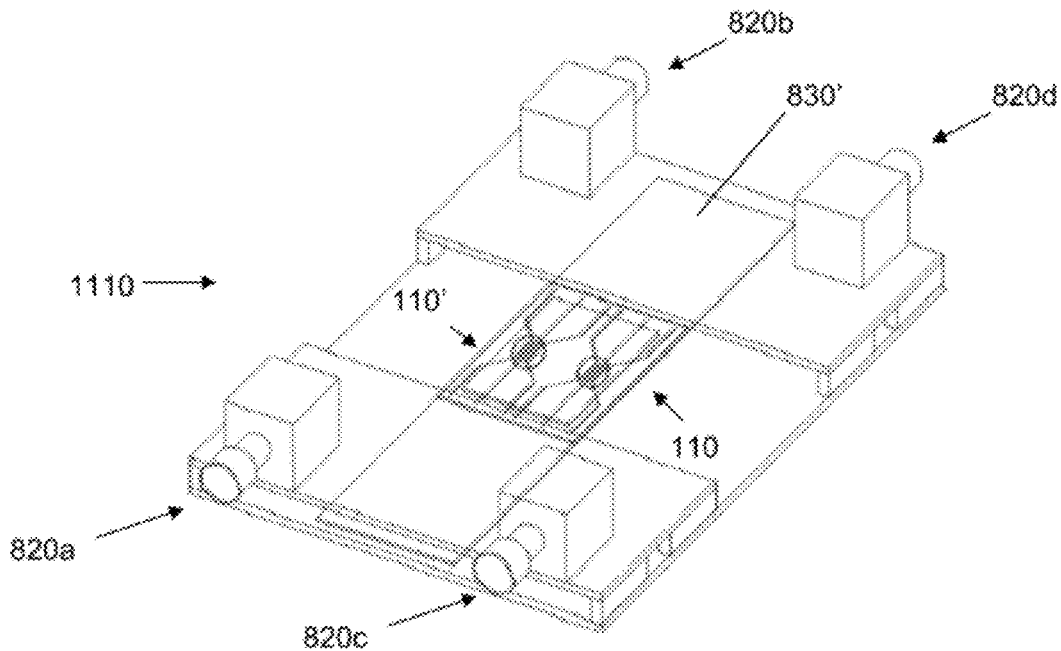

FIG. 12 illustrates a perspective view of the housing illustrated in FIG. 11.

Figure 13:
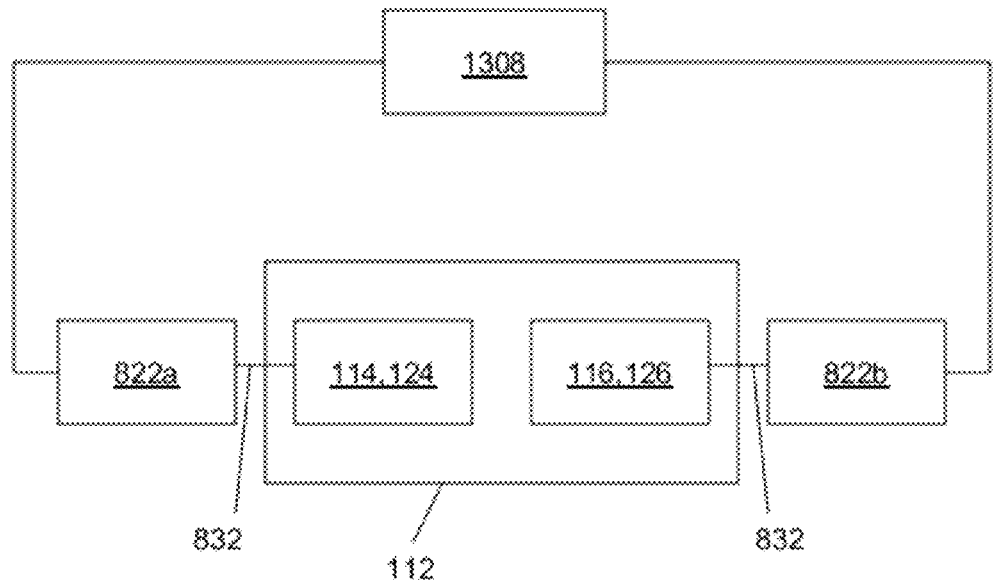

FIG. 13 illustrates a block diagram of a controller embodiment according to the invention.

Figure 14:
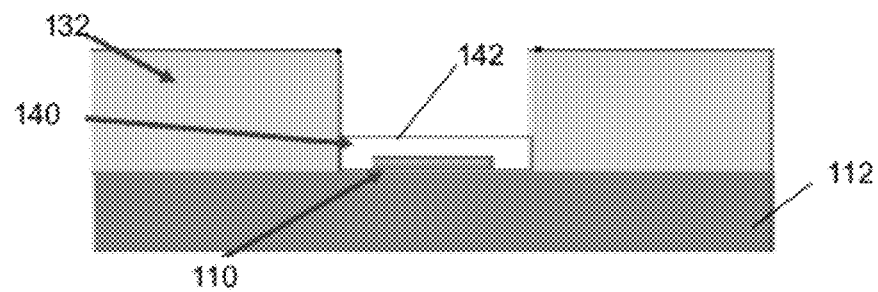

FIG. 14 illustrates a side view of a well embodiment according to the invention.

Figure 15:
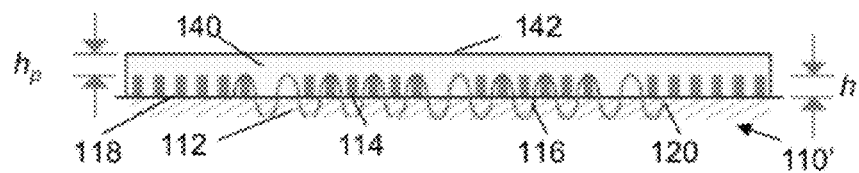

FIG. 15 illustrates a representation of a sensing area according to the invention.

Figure 16:
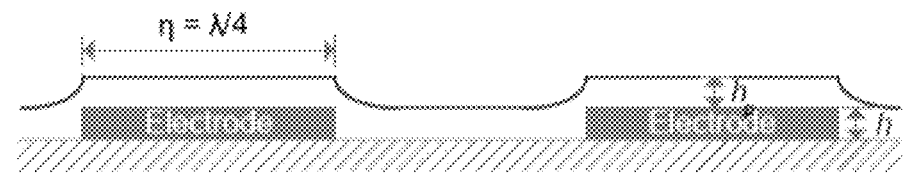

FIG. 16 illustrates a portion of the SAW resonator covered by a polymer layer according to the invention.

Figure 17:
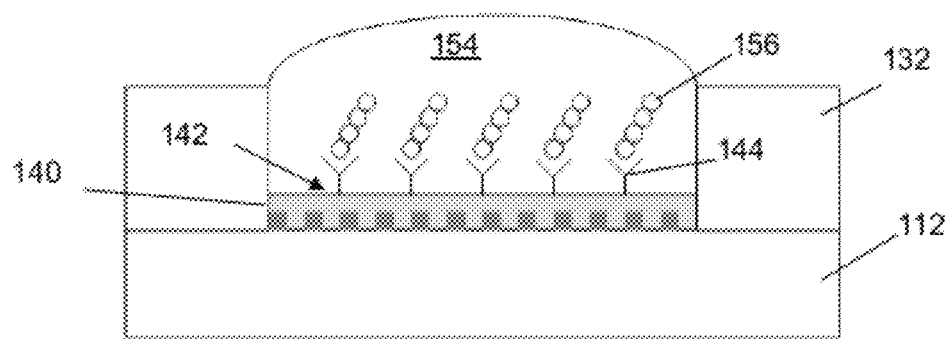

FIG. 17 illustrates a SAW mass sensor embodiment with a well and material to be analyzed according to the invention.

Figure 18:
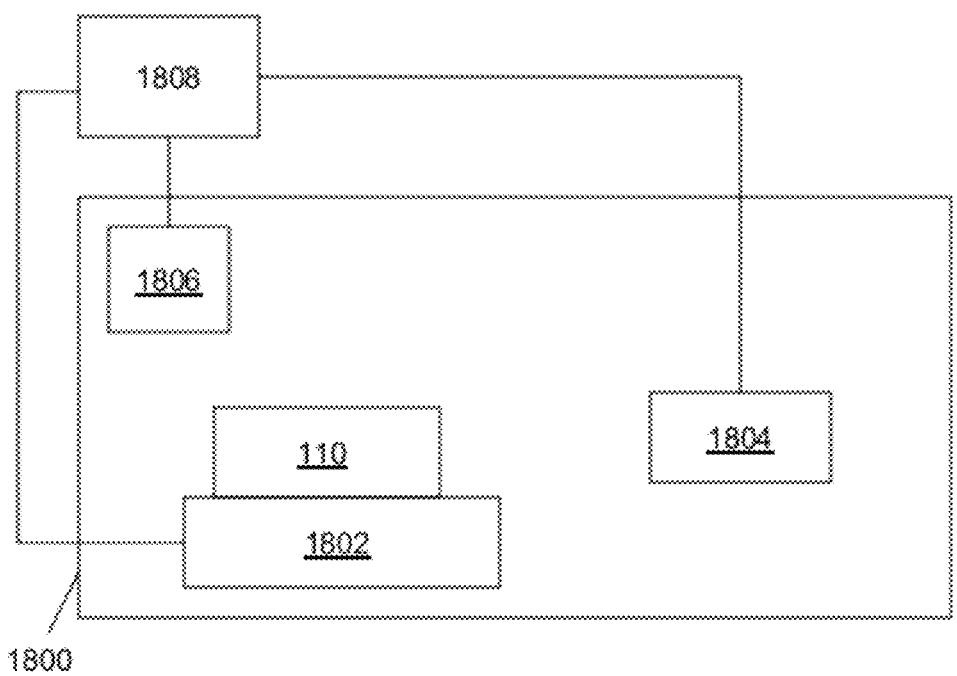

FIG. 18 illustrates a block diagram of a temperature control embodiment according to the invention.

Figure 19:
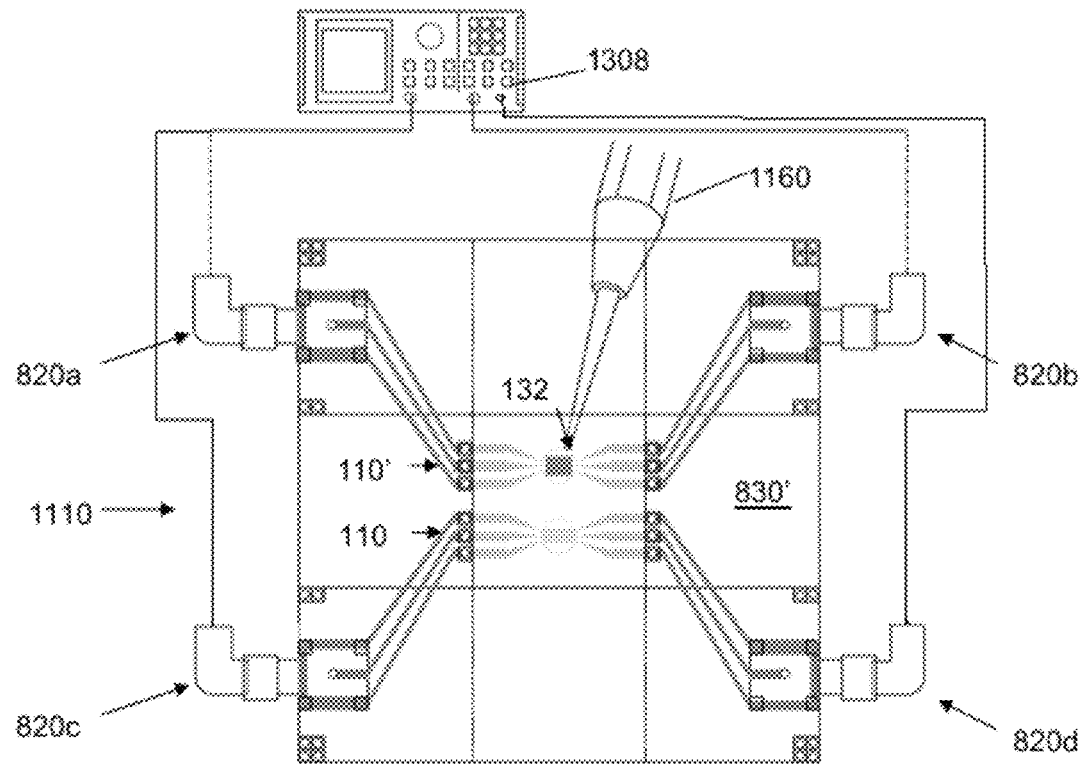

FIG. 19 illustrates an embodiment to account for environmental shifts in performance of a SAW mass sensor according to the invention.

Figure 20:
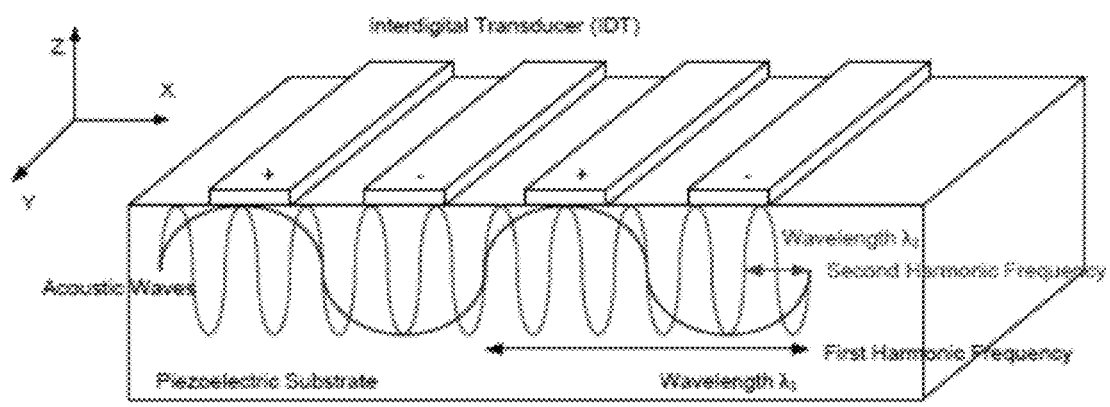

FIG. 20 illustrates the propagation of Rayleigh waves on a piezoelectric surface having different harmonic frequencies that are excited between the electrodes.

Figure 21:
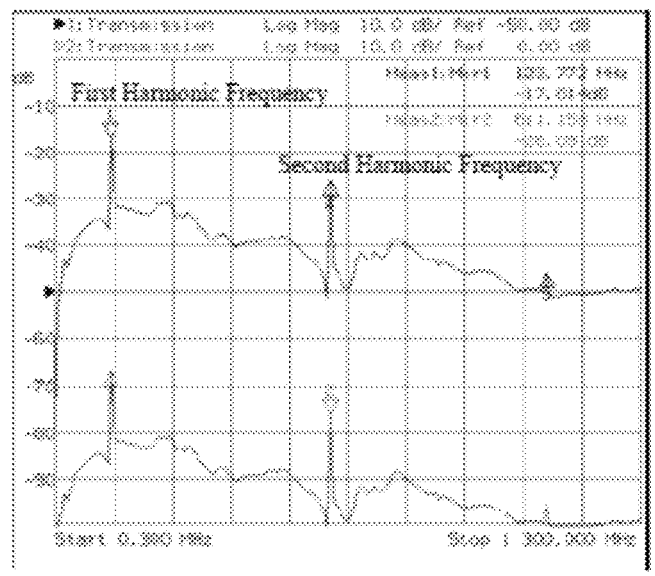

FIG. 21 illustrates the frequency response of two harmonic frequencies on a 128° YX $LiNbO_3$ substrate.

Figure 22A:
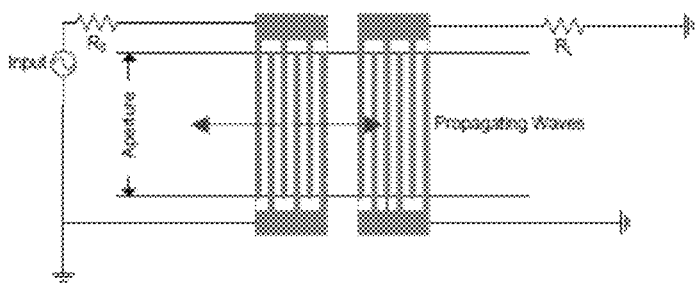
Figure 22B:
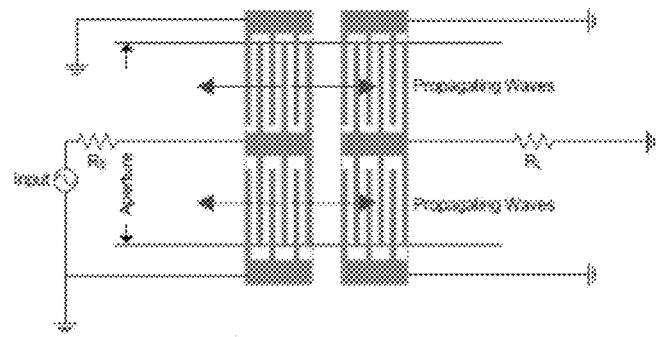

FIGS. 22A and 22B illustrate single-track and parallel track bidirectional SAW resonators.

Figure 23:
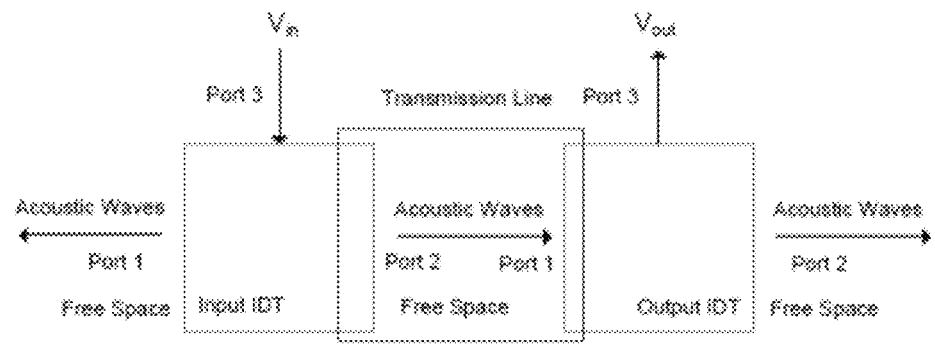

FIG. 23 illustrates a block representation of bidirectional SAW resonators where the input IDT can be translated into a three-port network.

Figure 24:
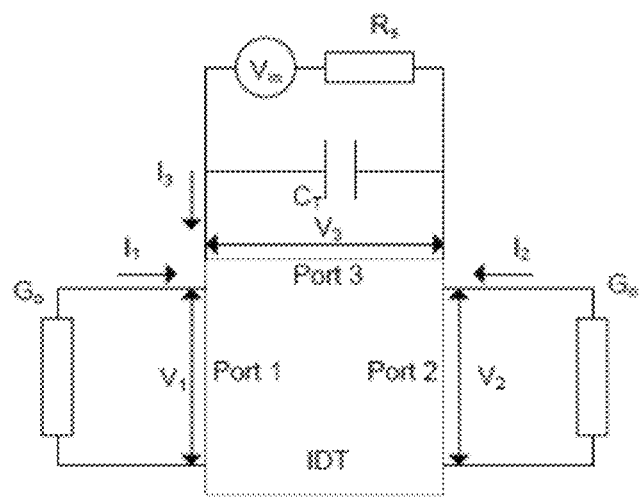

FIG. 24 illustrates a three-port equivalent Y admittance network of an IDT where $G_0$ is the equivalent electrical conductance and $C_T$ is the total capacitance of the electrodes.

Figure 25:
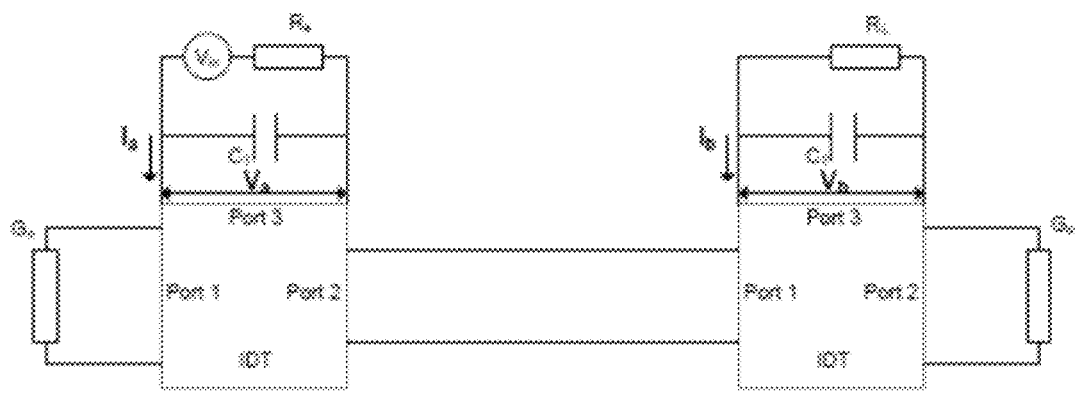

FIG. 25 illustrates a three-port network of input/output IDTS with $V_a$ and $V_b$ being the electrical port of input and output, respectively, which can be translated into a two-port equivalent circuit.

Figure 26:
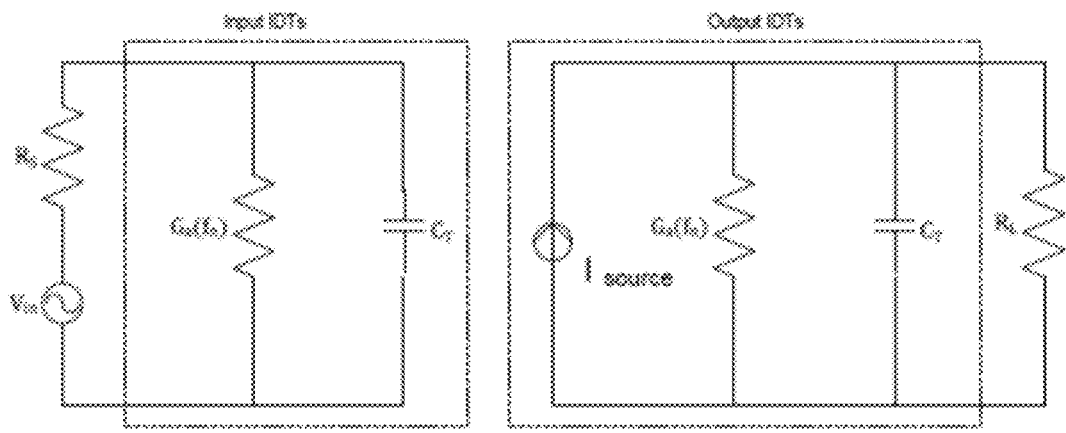

FIG. 26 illustrates an equivalent circuit for a bidirectional SAW resonator where the three-port networks of input and output IDTs are translated into two-port circuits with $R_S$ and $R_L$ being the source and load resistances.

Figure 27A:
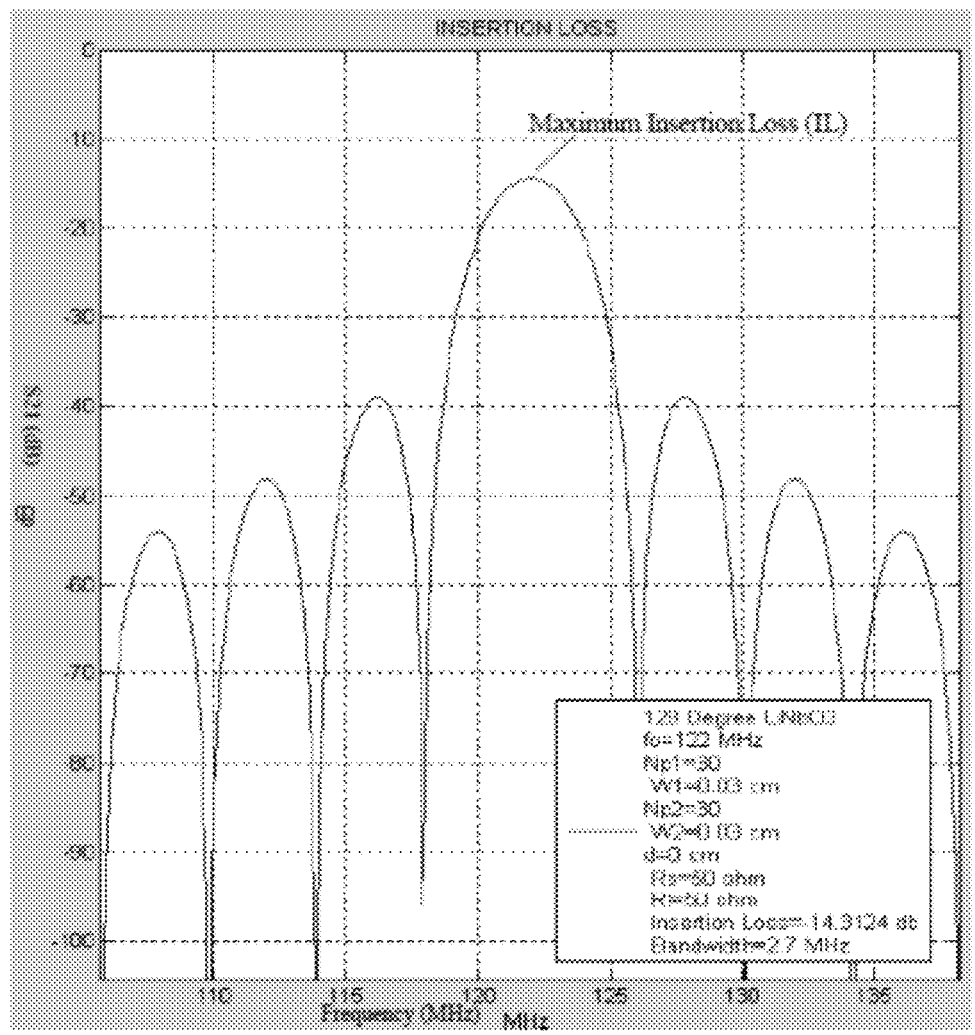

FIG. 27A depicts a graph from a MATLAB simulation of a bidirectional SAW resonator on a 128° YX $LiNbO_3$ substrate where the maximum insertion loss of $S_{21}$ response is −14.3124 dB in a 121 MHz SAW resonator with thirty finger pairs in the input IDT and the output IDT.

Figure 27B:
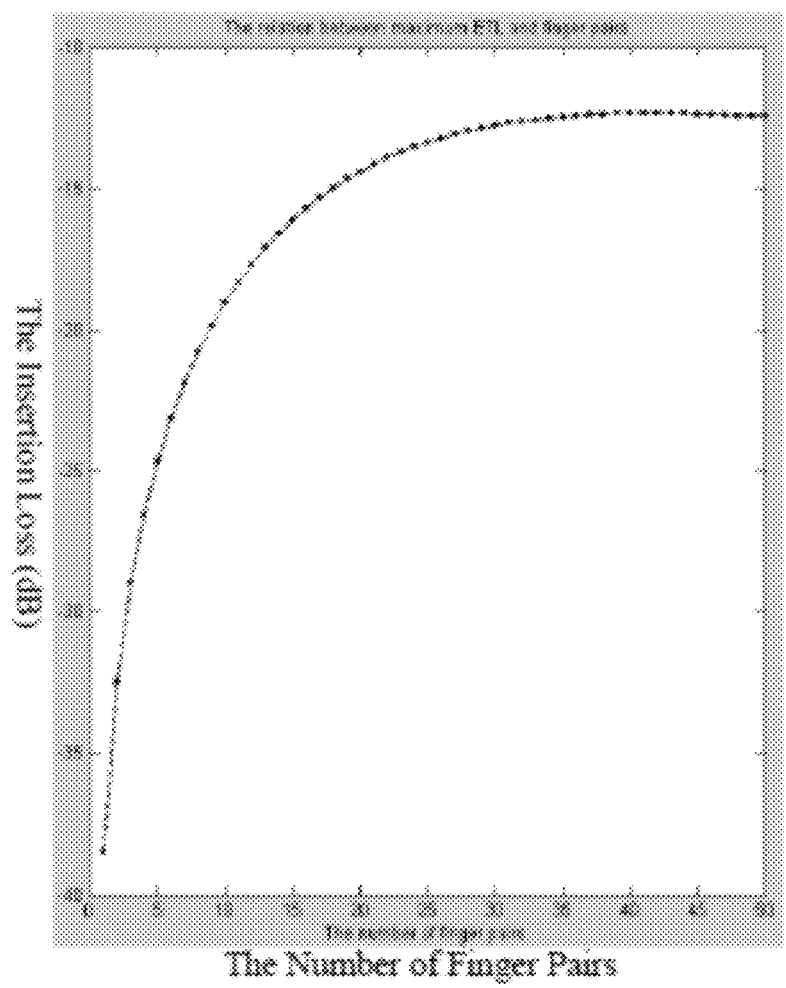

FIG. 27B depicts the insertion loss of bidirectional SAW resonators on a 128° YX $LiNbO_3$ substrate based on the number of finger pairs.

Figure 28:
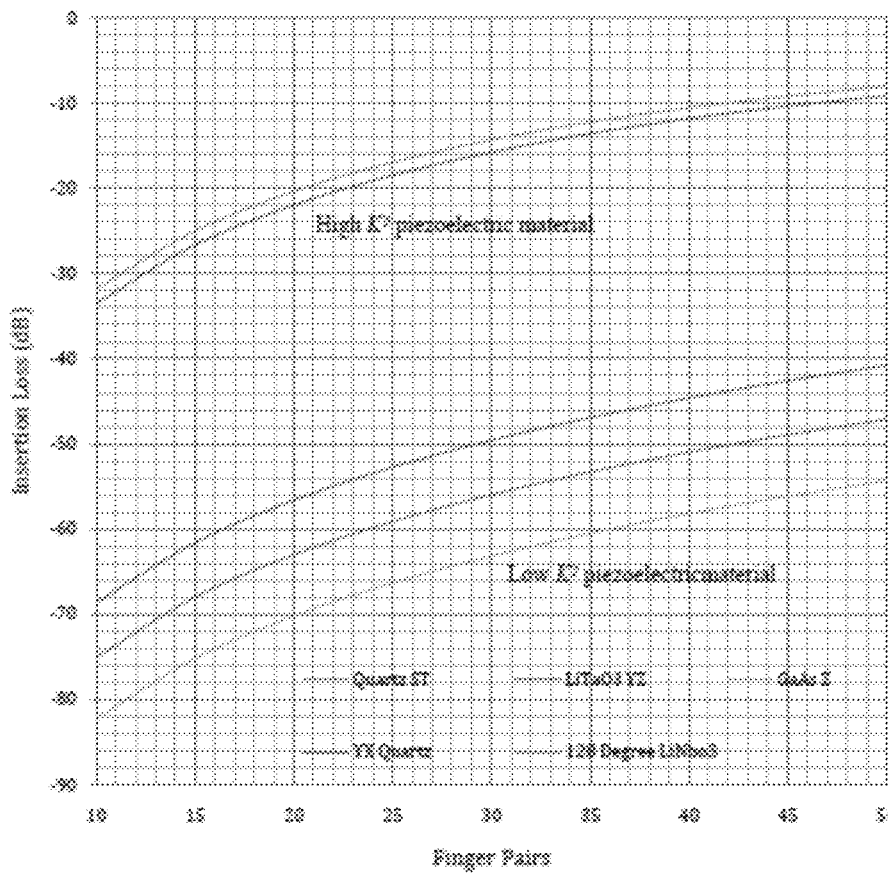

FIG. 28 depicts a graph showing the maximum insertion loss of bidirectional SAW resonator versus finger pairs using different substrate material.

Figure 29:
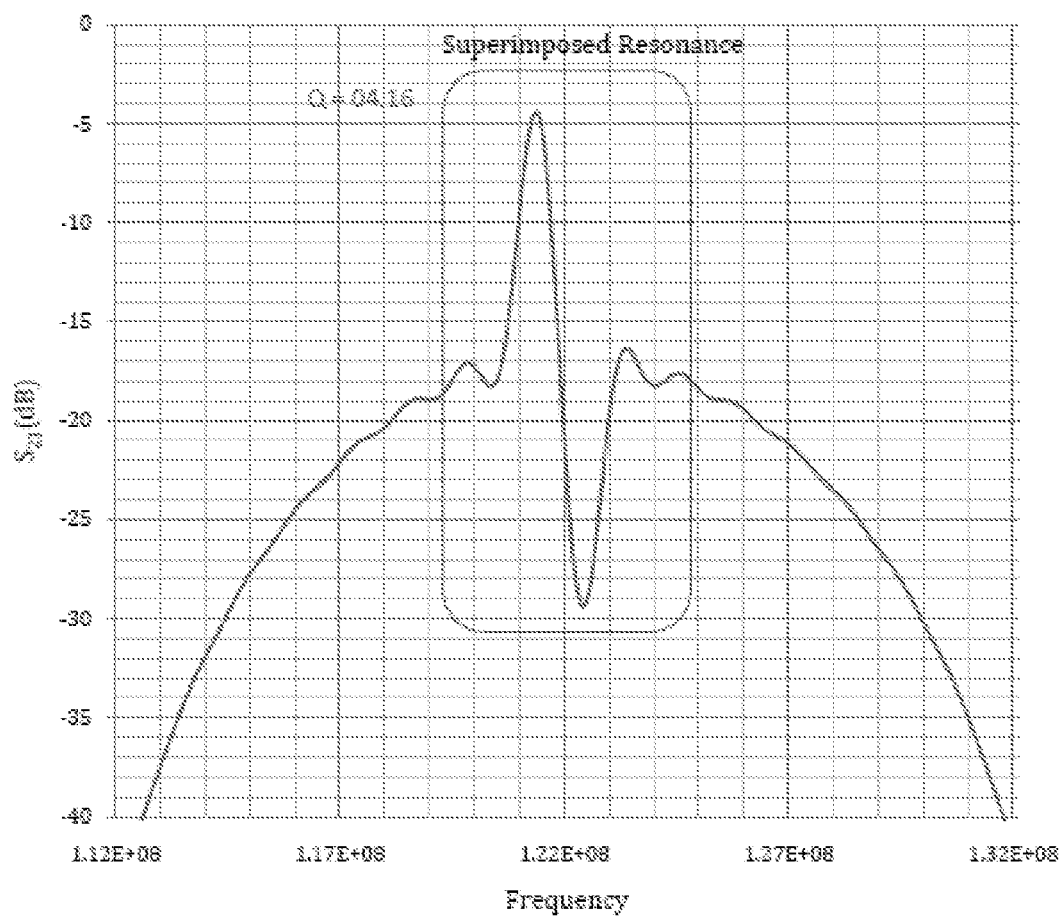

FIG. 29 shows a graph from a MATLAB simulation of a SAW resonator with shorted reflectors symmetrically placed around the input and output IDTs showing an asymmetric resonance superimposed on the center frequency with a maximum insertion loss of −4.86 dB for a 121 MHz SAW resonator.

Figure 30:
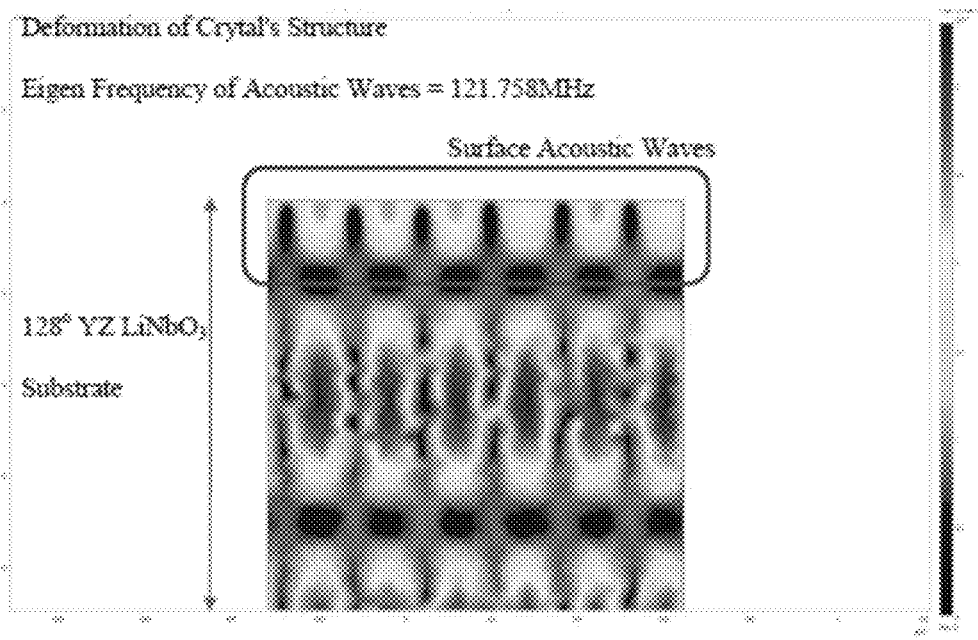

FIG. 30 depicts a cross view of $LiNbO_3$ crystal structures disturbed by surface acoustic waves with a scale along the right side of the figure.

Figure 31A:
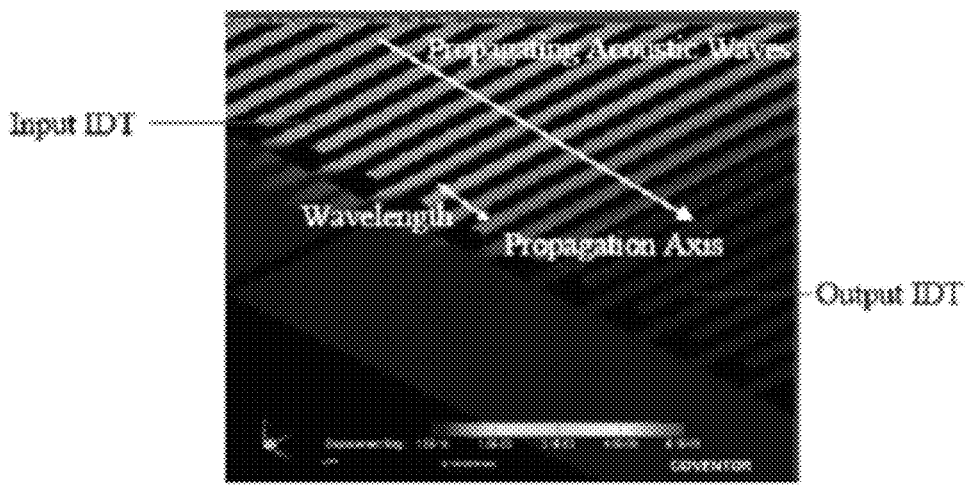
Figure 31B:
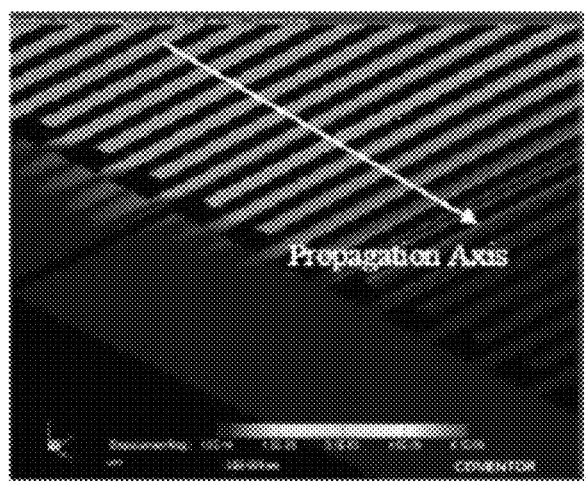
Figure 31C:
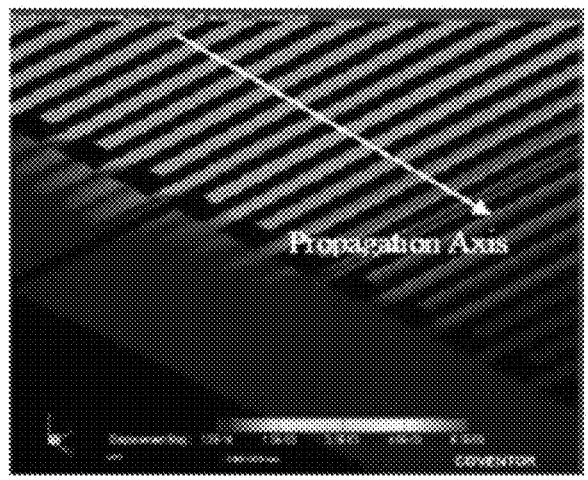

FIGS. 31A-31C depict a transit simulation in Coventorware that shows the acoustic waves propagate gradually from the input IDT to the output IDT at $3.1e^{-8}$ s, $3.5e^{-8}$ s, and $3.9e^{-8}$ s.

Figure 32:
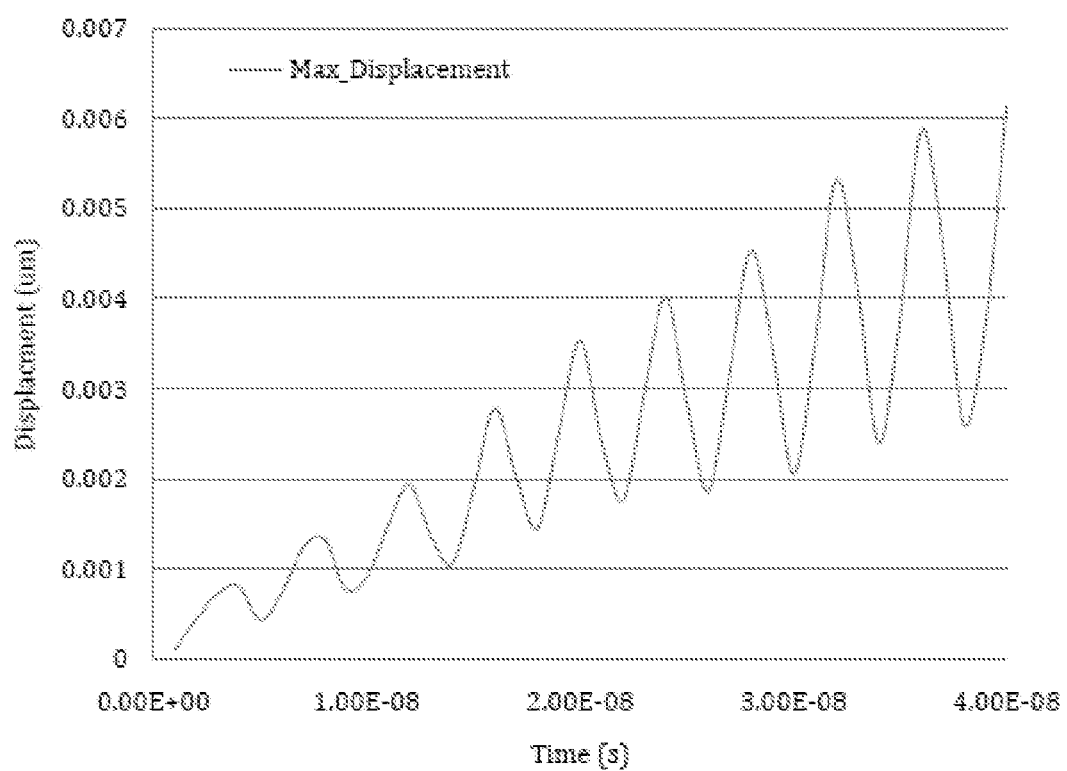

FIG. 32 depicts a graphical representation of how the maximum displacement of a 121 MHz resonator increases gradually in a transit simulation.

Figure 33A:
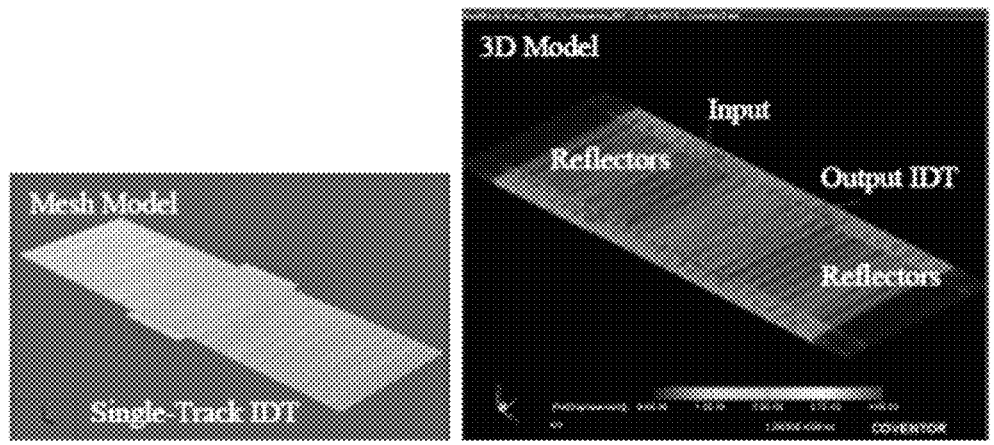
Figure 33B:
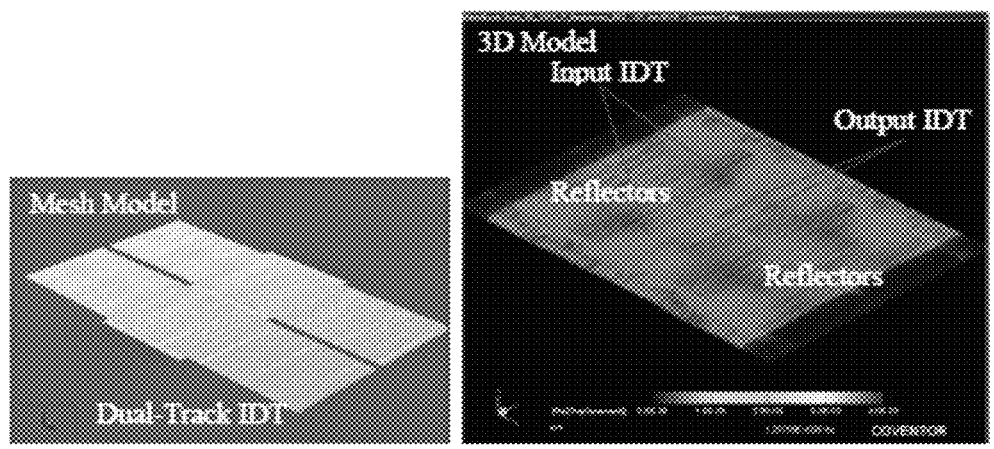

FIGS. 33A and 33B depict a mash model and a 3D model for a single-track SAW resonator and a parallel track (dual-track) SAW resonator both with shorted reflectors, respectively, with the magnitudes of displacement shown in different colors.

Figure 34:
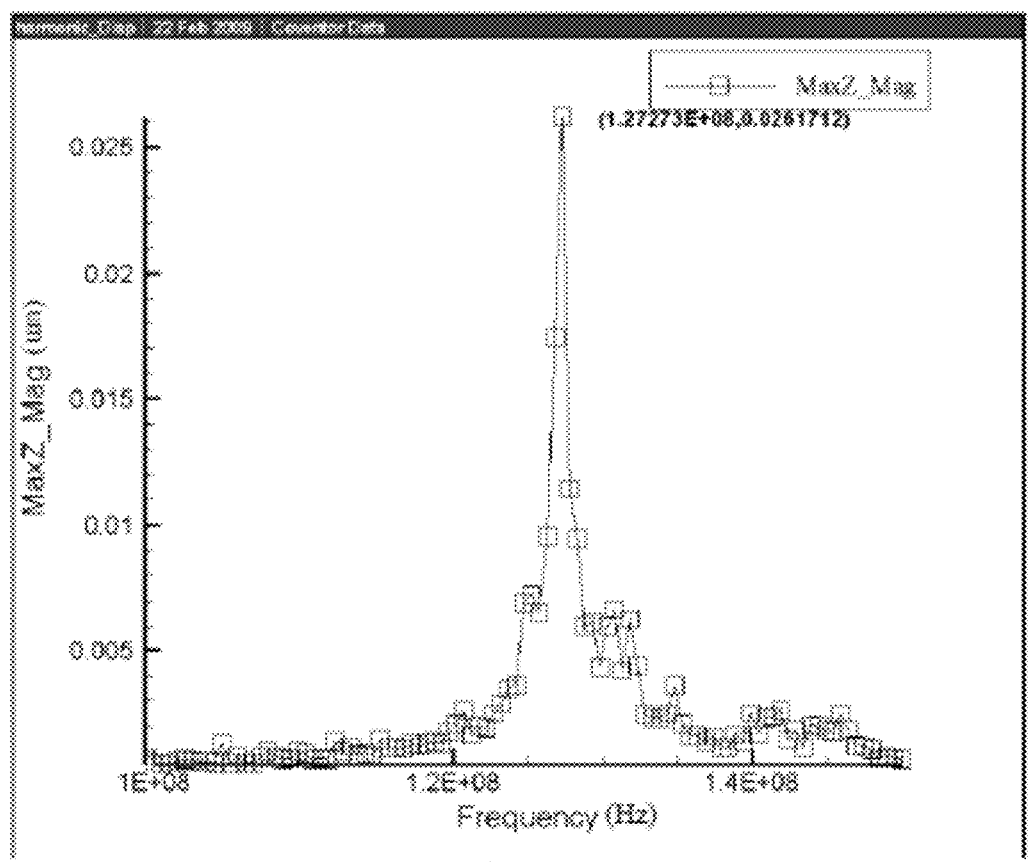

FIG. 34 graphically depicts the displacement in the Z axis of a SAW resonator with shorted reflectors where the maximum displacement occurs in the center frequency.

Figure 35:
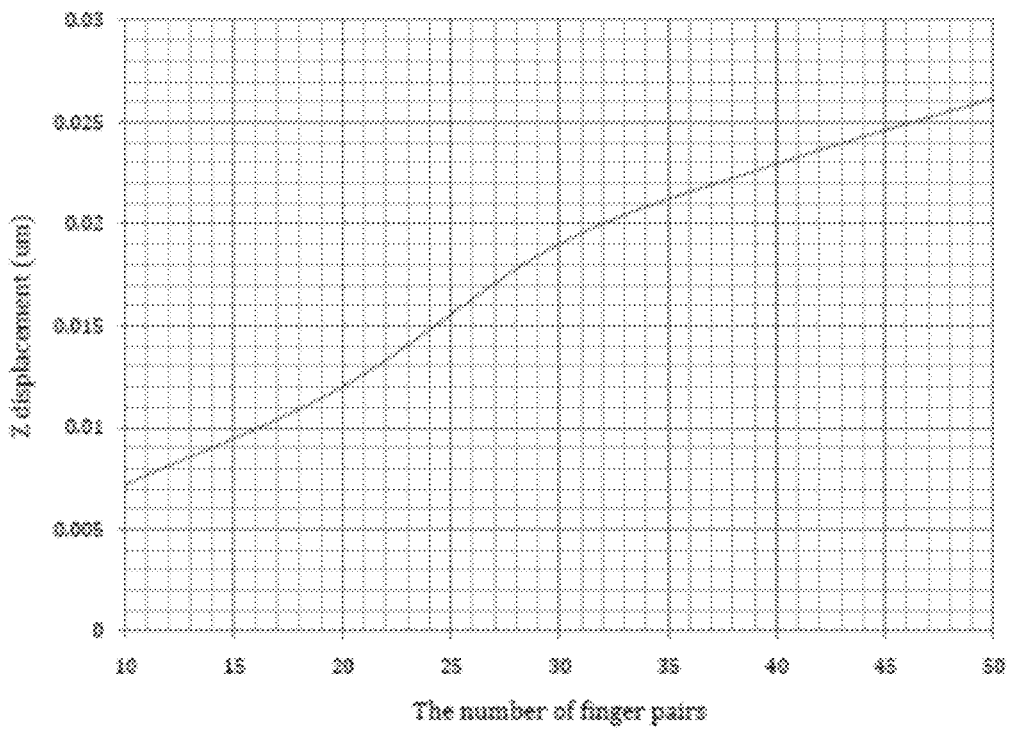

FIG. 35 graphically depicts the maximum displacement in the Z axis versus finger pairs from a Coventorware simulation.

Figure 36:
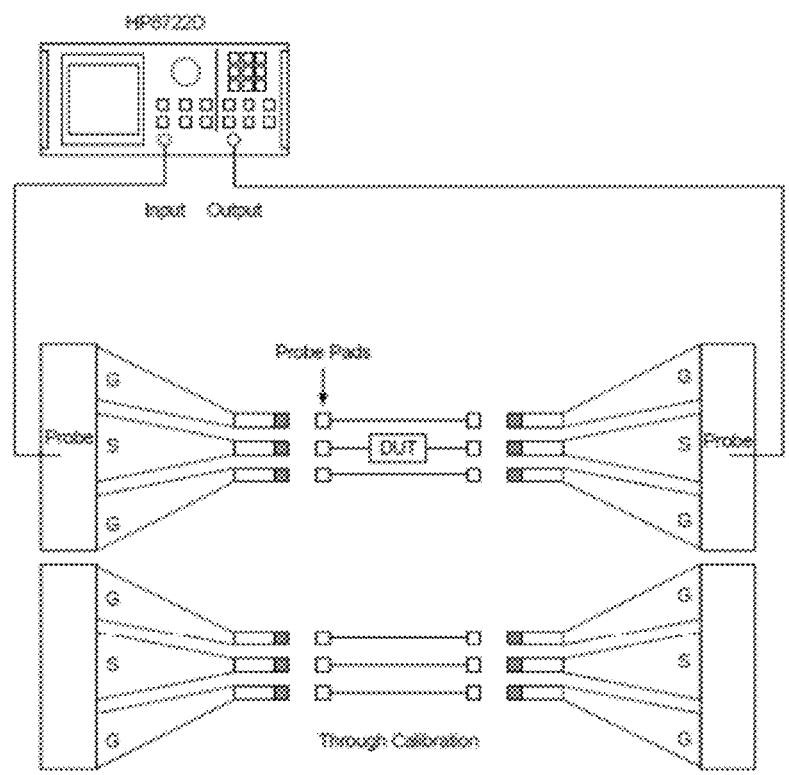

FIG. 36 illustrates a measurement and calibration setup that allowed for the parasitic effects between the probe pads and the network analyzer to be calibrated by the through circuit where the device under test is a SAW resonator built according to the invention connected to the probe pads.

Figure 37:
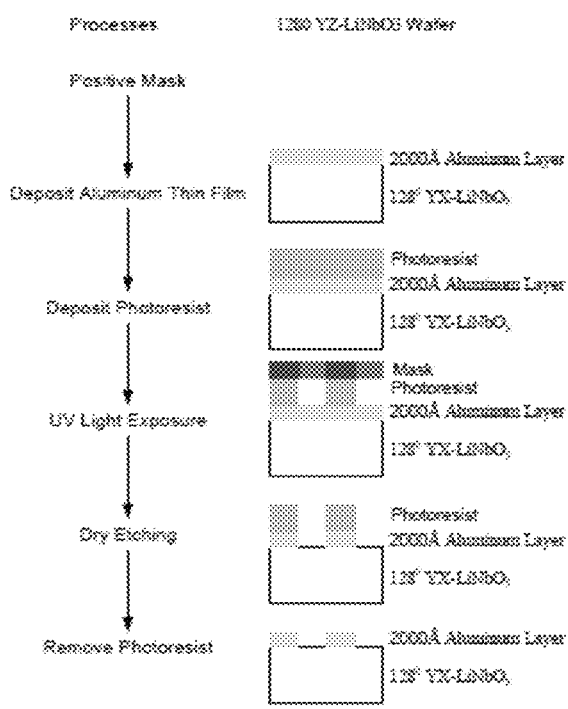

FIG. 37 illustrates the process flow of micro fabrication on a four inch 128° YX $LiNbO_3$ wafer with cross views of a portion of the wafers at each step.

Figure 38:
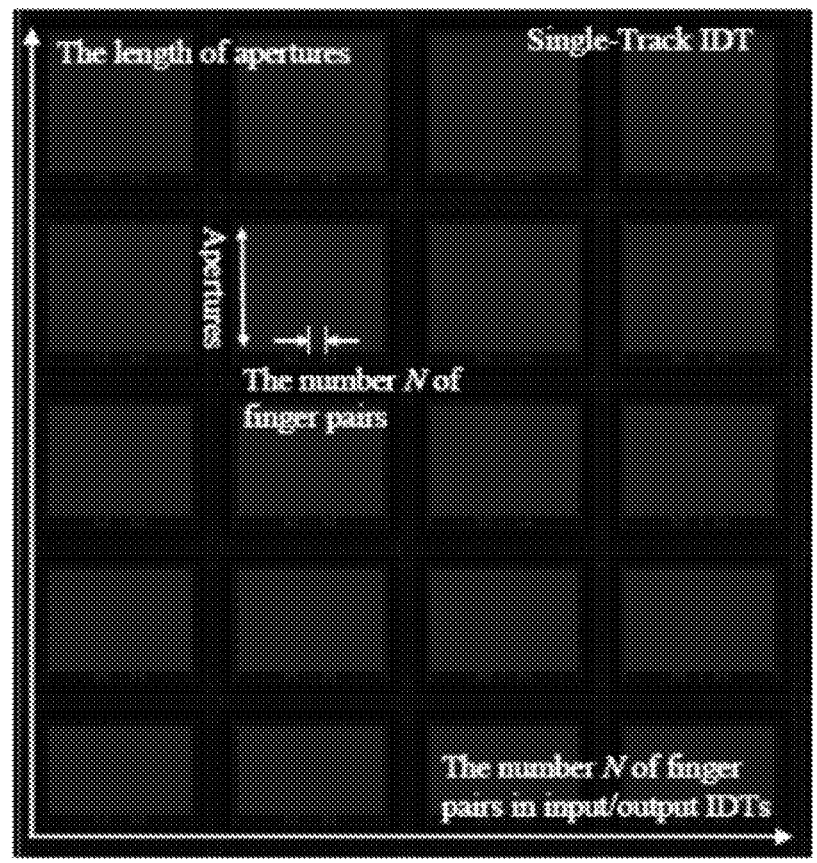

FIG. 38 depicts a layout of SAW resonators in Cadence with different sizes of SAW resonators being designed on the four inch wafer.

Figure 39A:
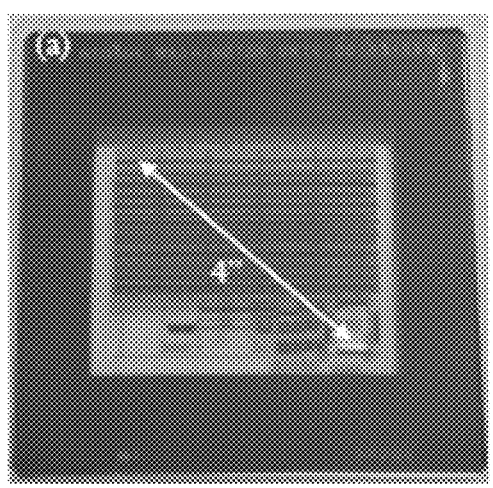
Figure 39B:
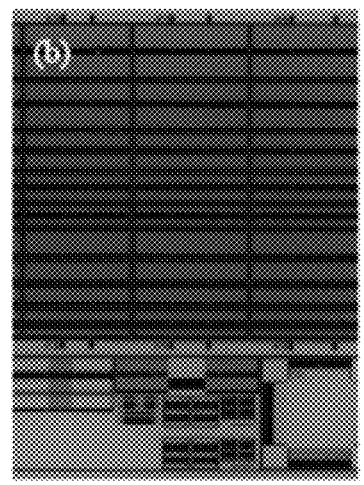

FIG. 39A depicts a five inch mask for the lithography of the four inch wafer. FIG. 39B depicts the SAW structures on a four inch 128° YX $LiNbO_3$ wafer.

Figure 40A:
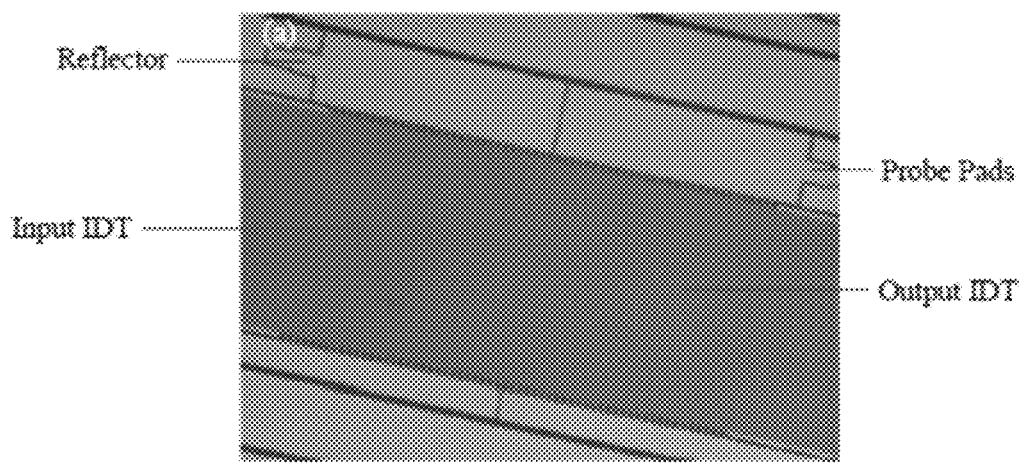
Figure 40B:
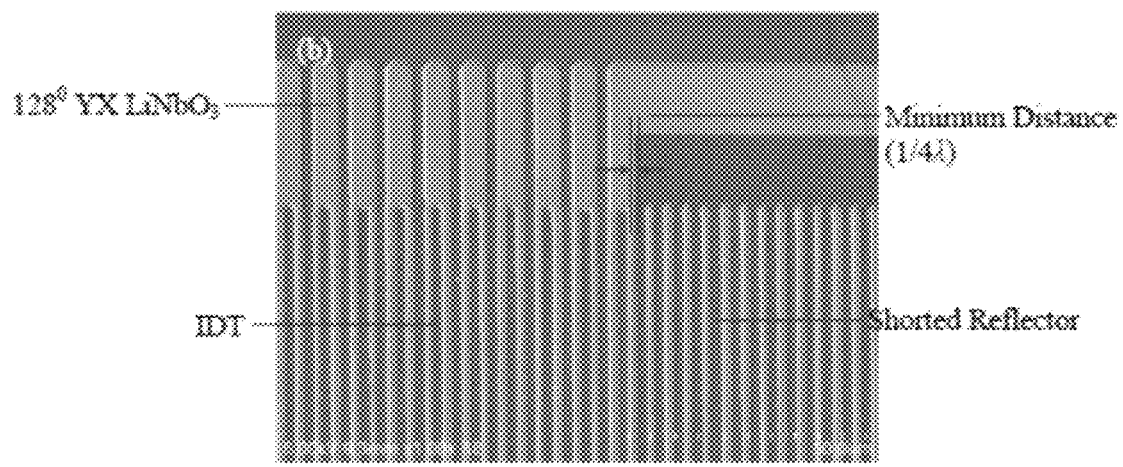
Figure 40C:
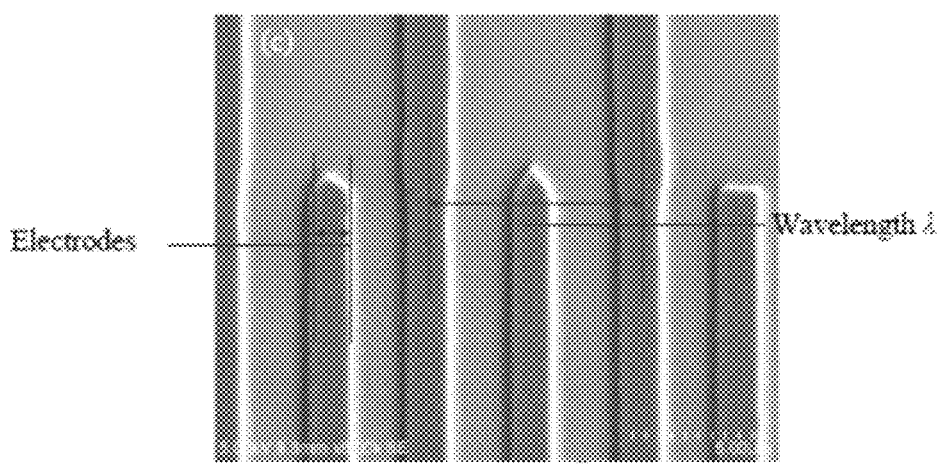

FIGS. 40A-40B depict SEMs of the IDTs and gratings on a 128° YX LiNbO$_3$ wafer where the width of the electrodes is 8 μm, which yields a center frequency of up to 121 MHz. FIG. 40A depicts the input and output IDTs with shorted gratings. FIG. 40B depicts the minimum distance between an IDT and a grating. FIG. 40C depicts the width of the electrodes where the metallization is equal to 50%.

Figure 41:
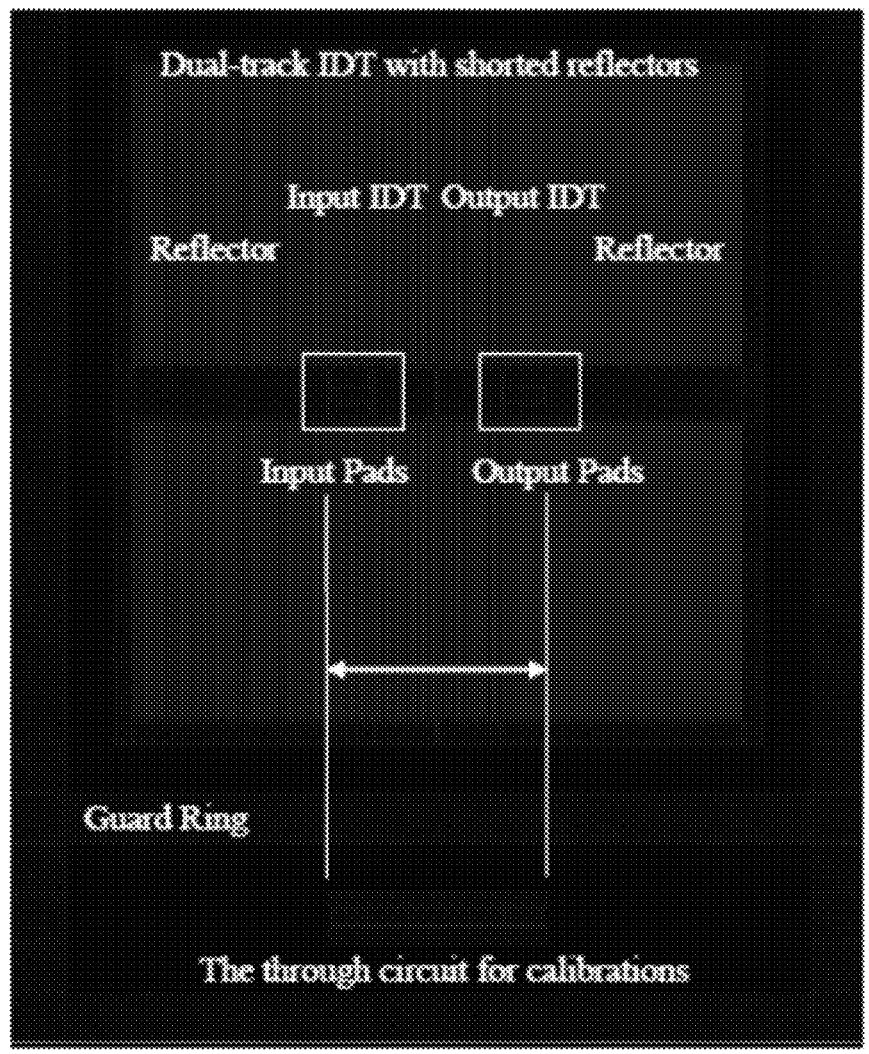

FIG. 41 depicts a layout of probe pads for the through calibration where the distance between the input and output pads is the same as the calibration pads.

Figure 42:
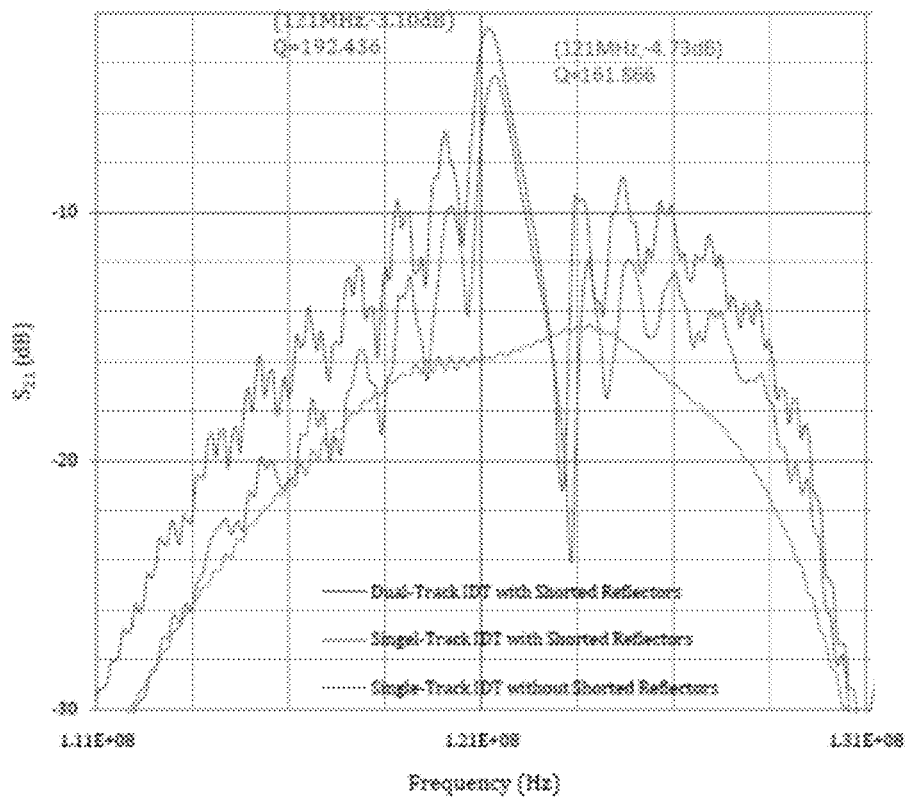

FIG. 42 graphically depicts the frequency response for 121 MHz SAW resonators to show the differences between a single-track SAW resonator without gratings, a single-track SAW resonator with gratings, and a parallel track (or dual-track) SAW resonator with gratings where the gratings provide for a one-pole resonance with 90° phase shift superimposed on the center frequency.

Figure 43:
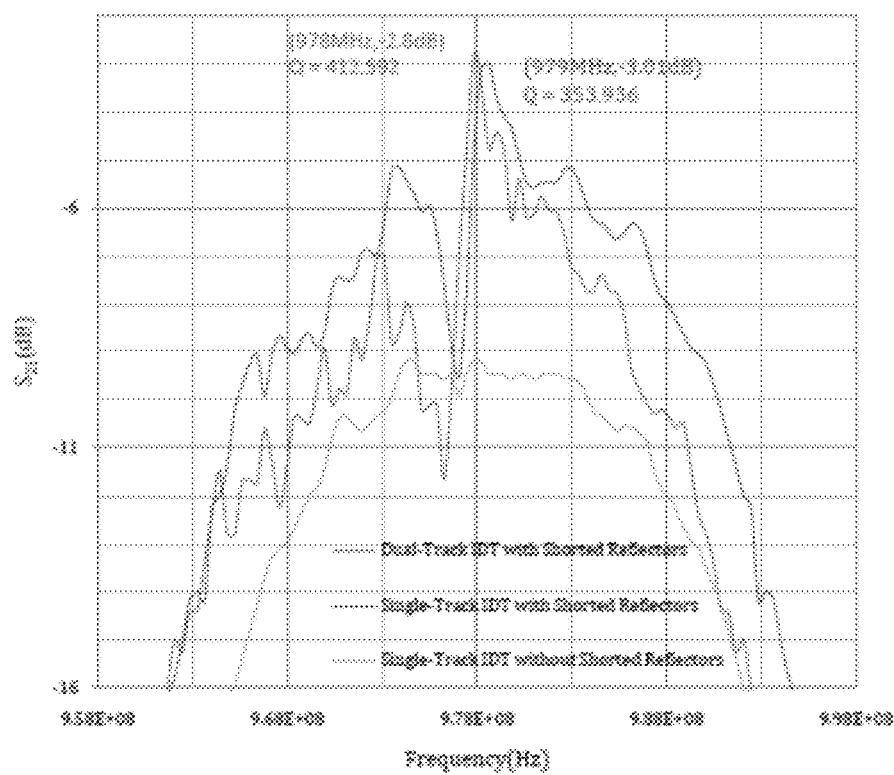

FIG. 43 graphically depicts the frequency response for 978 MHz SAW resonators to show the differences between a single-track SAW resonator without gratings, a single-track SAW resonator with gratings, and a parallel track (or dual-track) SAW resonator with gratings. The parallel track SAW resonator has a −2.8 dB insertion loss.

Figure 44:
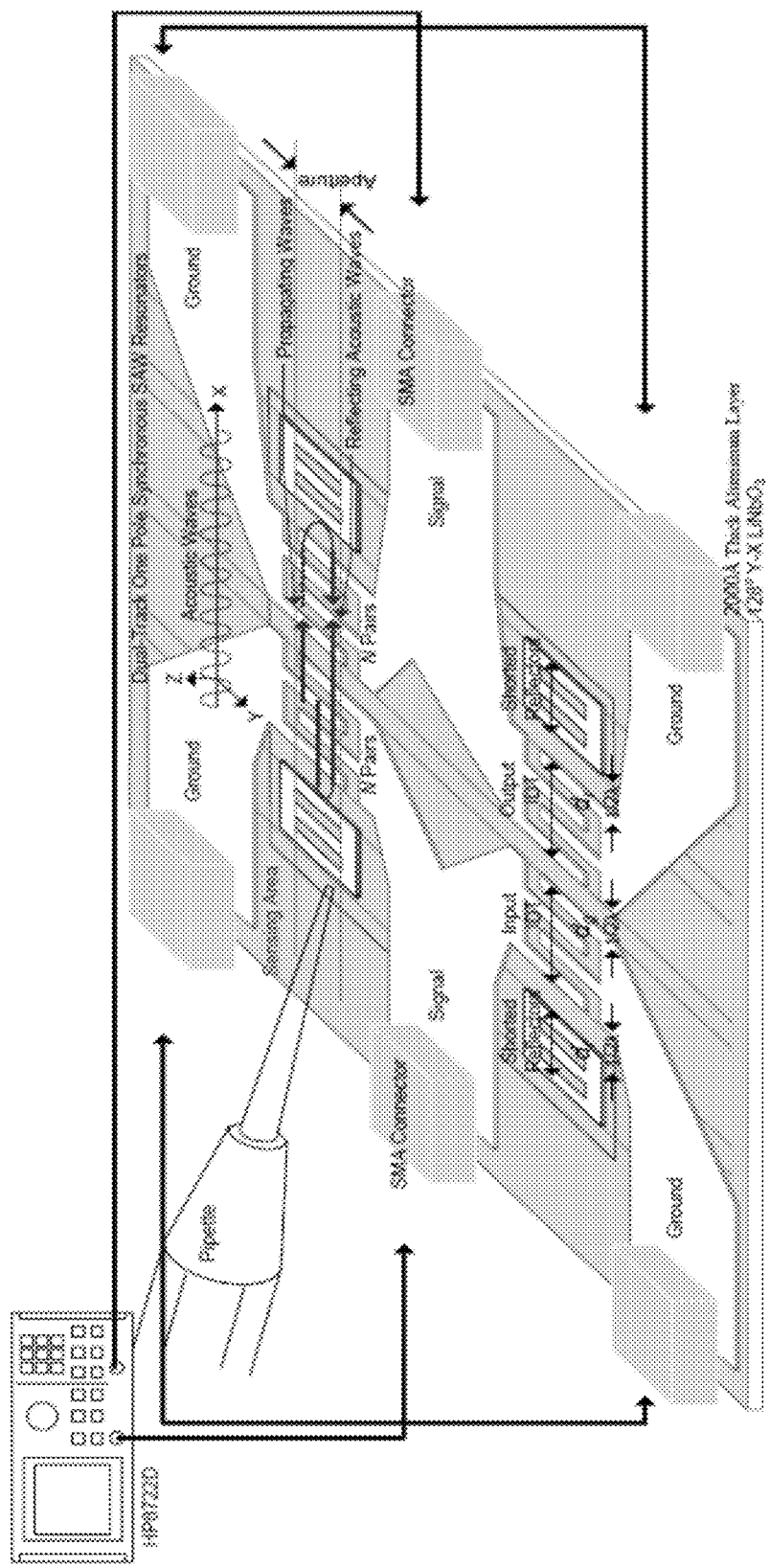

FIG. 44 illustrates a configuration and measurement of a SAW mass sensor where the sensing area covers the input IDT, the output IDT and the gratings according to the invention.

Figure 45A:
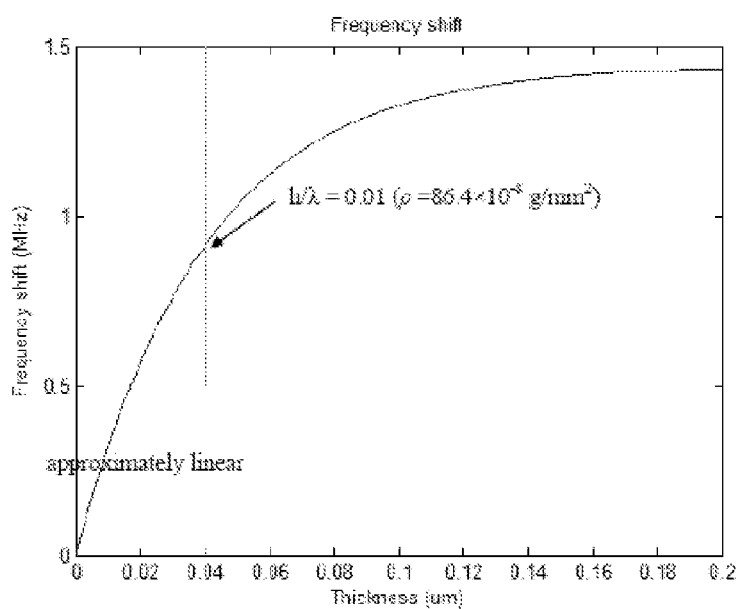
Figure 45B:
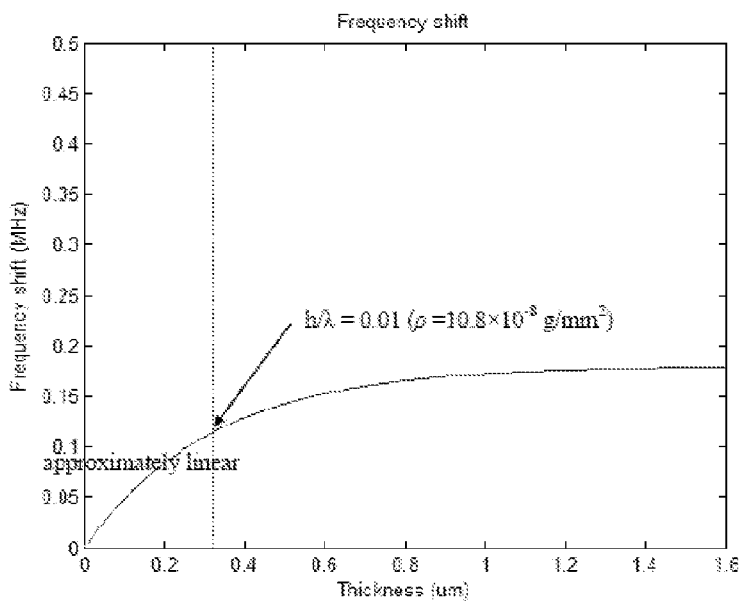

FIGS. 45A and 45B graphically illustrate the frequency shift versus different thicknesses of the mass on the electrodes. Based on Equation 26, the frequency shifts are linear to the thickness of mass where the film-thickness ratio h/A is less than 0.01. FIG. 45A illustrates the shift for a 122 MHz SAW mass sensor, while FIG. 45B illustrates a 978 MHz SAW mass sensor.

Figure 46:
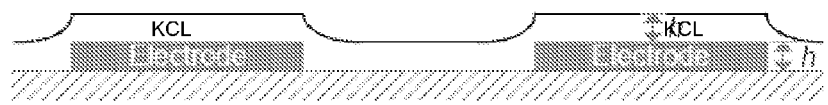

FIG. 46 illustrates a side view of two electrodes covered by KCL.

Figure 47:
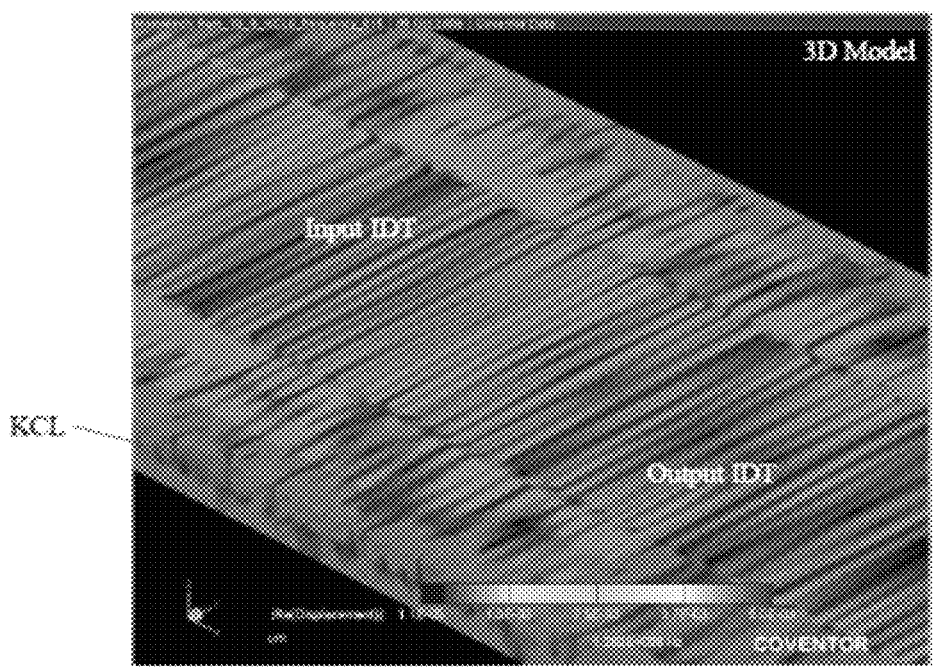

FIG. 47 depicts a 3D model of a SAW resonator with a layer of KCL in Coventorware where the displacement are shown as the acoustic waves propagate from the input IDT to the output IDT.

Figure 48:
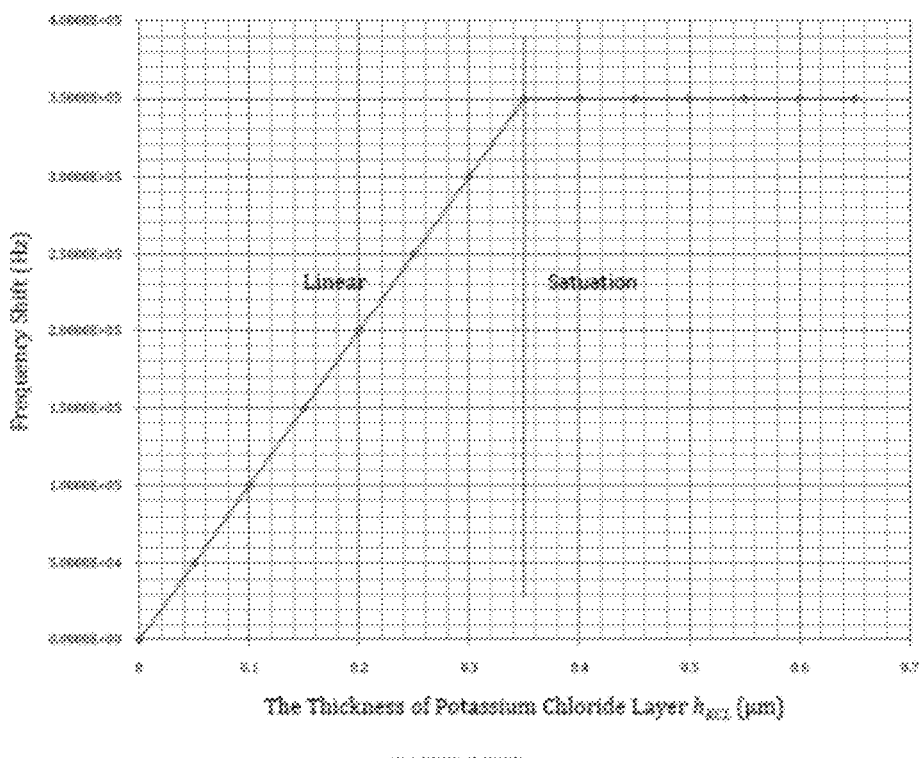

FIG. 48 graphically depicts a Coverntorware simulation of frequency shifts when different thicknesses of KCL are deposited on the surface of the SAW mass sensor. A linear region is depicted when the thickness of the KCL layer is less than 0.3 μm.

Figure 49:
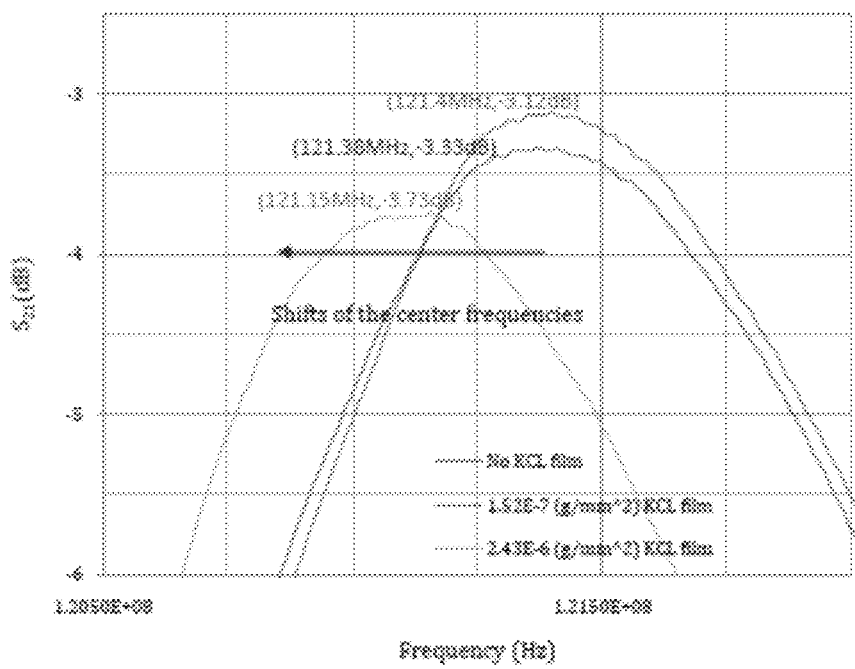

FIG. 49 graphically depicts how the center frequency of a 121 MHz parallel track SAW resonator shifts due to a KCL film on the electrodes where the center frequency decreases when the additional mass of the KCL film is deposited.

Figure 50:
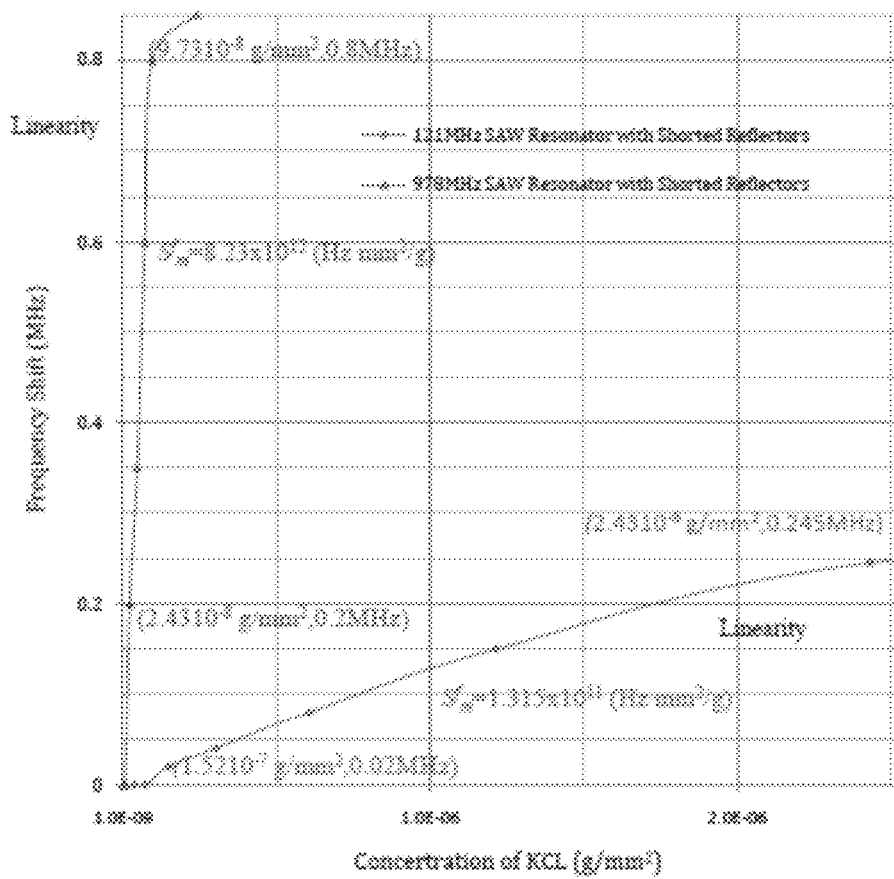

FIG. 50 graphically depicts the frequency shifts versus mass densities of different KCL films for a 121 MHz SAW mass sensor and a 978 MHz SAW mass sensor fabricated according to the invention. The results from an Aglient 8722D network analyzer found the mass sensitivities to be 1.315× 10$^{11}$ Hz·mm$^2$/g and 8.23×10$^{12}$ Hz·mm$^2$/g for the 121 MHz and 978 MHz SAW mass sensors, respectively.

Figure 51:
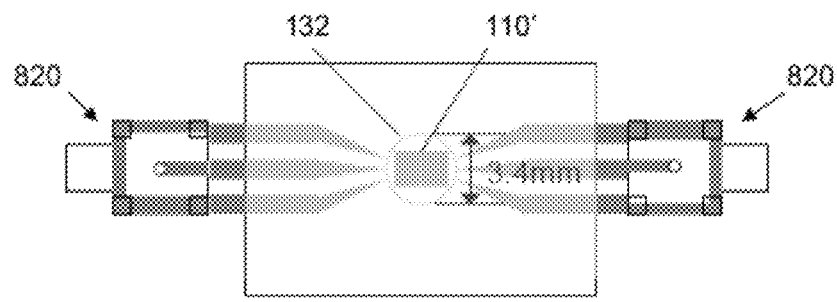

FIG. 51 illustrates a SAW mass sensor covered by a plastic well that provides a sensing area with a radius of 3.4 mm.

Figure 52:
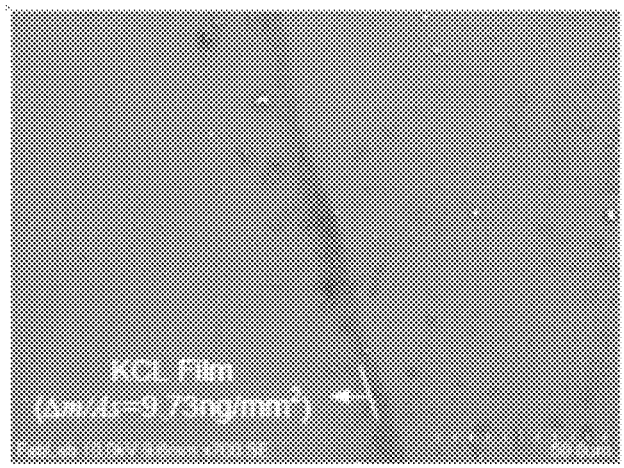

FIG. 52 depicts a KCL film (with a mass density equal to 9.73 ng/mm$^2$) that remained on the surface of the SAW mass sensor after the solvent had evaporated.

Figure 53:
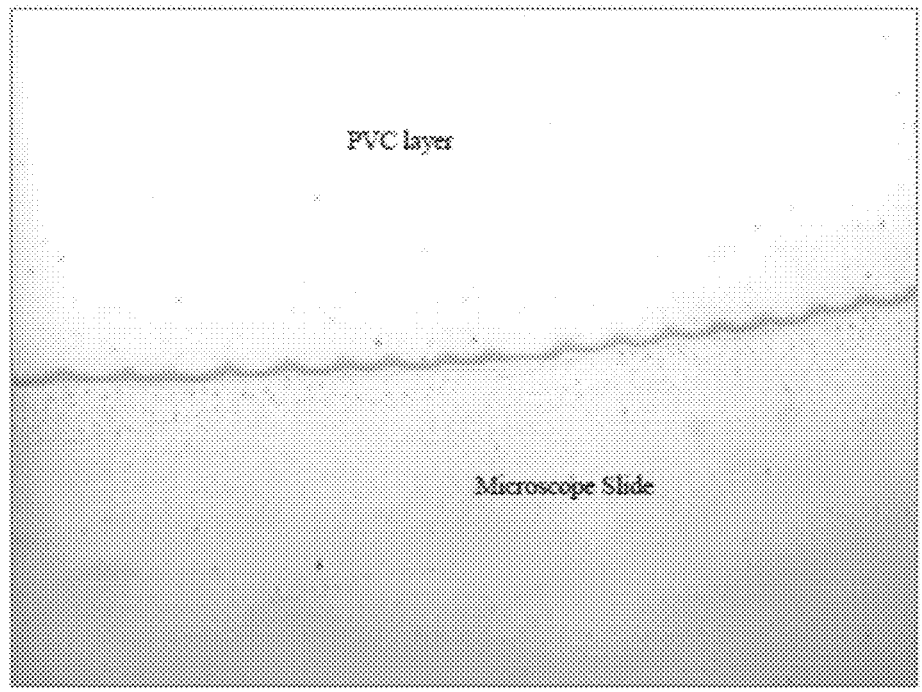

FIG. 53 depicts a PVC layer under a microscope where the PVC layer can be synthesized in a few seconds after the THF evaporates. This image also illustrates the smooth and uniform surface of the PVC layer.

Figure 54:
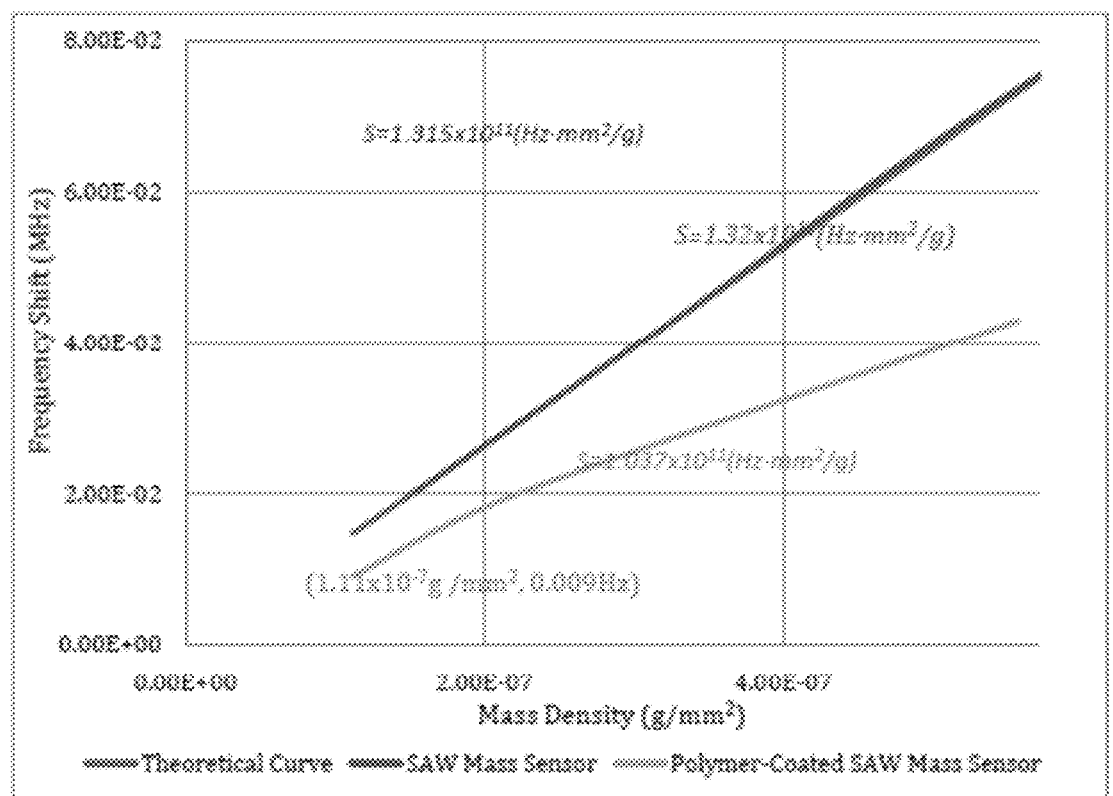

FIG. 54 graphically depicts the mass sensitivity of SAW mass sensors where a 121 MHz polymer-coated SAW mass sensor has slightly less sensitivity than a SAW mass sensor without the polymer coating.

Figure 55A:
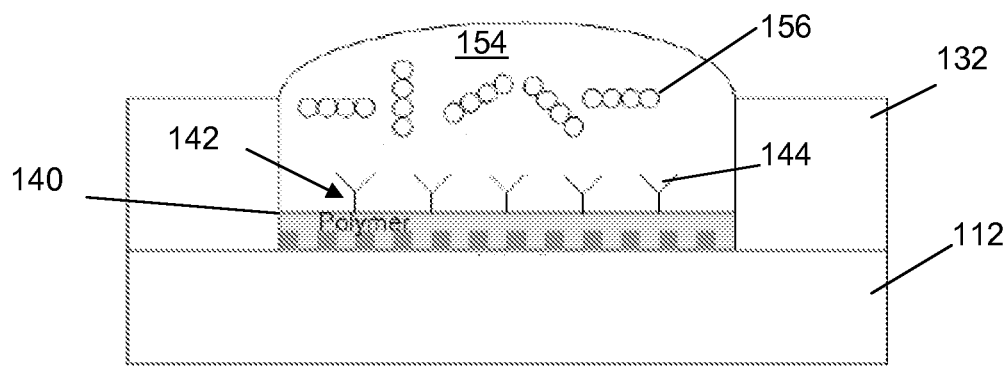
Figure 55B:
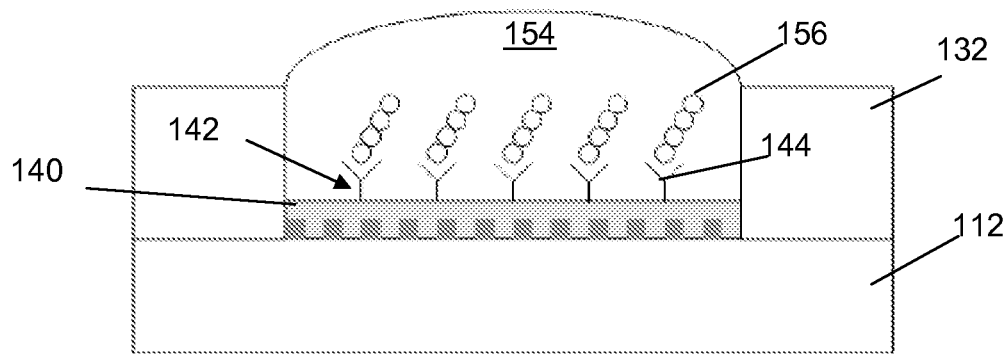
Figure 55C:
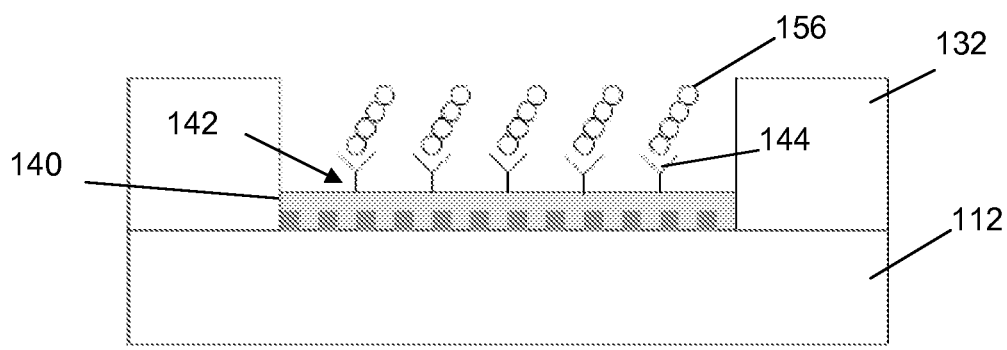

FIGS. 55A-55C illustrate the process of antibody-antigen reactions on a polymer and biochemical coated SAW mass sensor. FIG. 55A illustrates the initial deposit of the material to be analyzed into a well. FIG. 55B illustrates antigen from the material to be analyzed attaching to antibodies. FIG. 55C illustrates the excess material having been washed away so that a frequency shift can be detected.

V. DETAILED DESCRIPTION OF THE DRAWINGS

The detailed description has been broken into four sections to ease navigation through the disclosure, but the use of section headings in the detailed description is done for the convenience of the reader and is not intended on placing any limitation on the use of the material for supporting the claims.

Figure 3A:
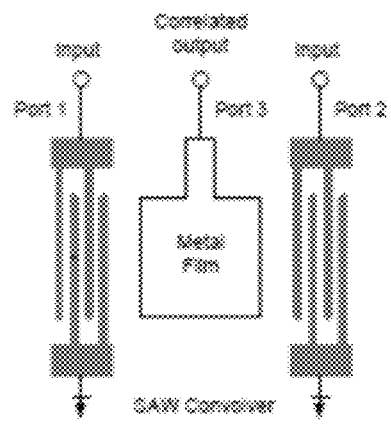
FIGS. 3A and 3B illustrate an example block diagram where a SAW resonator is used as a convolver in a spread spectrum system.
Figure 3B:
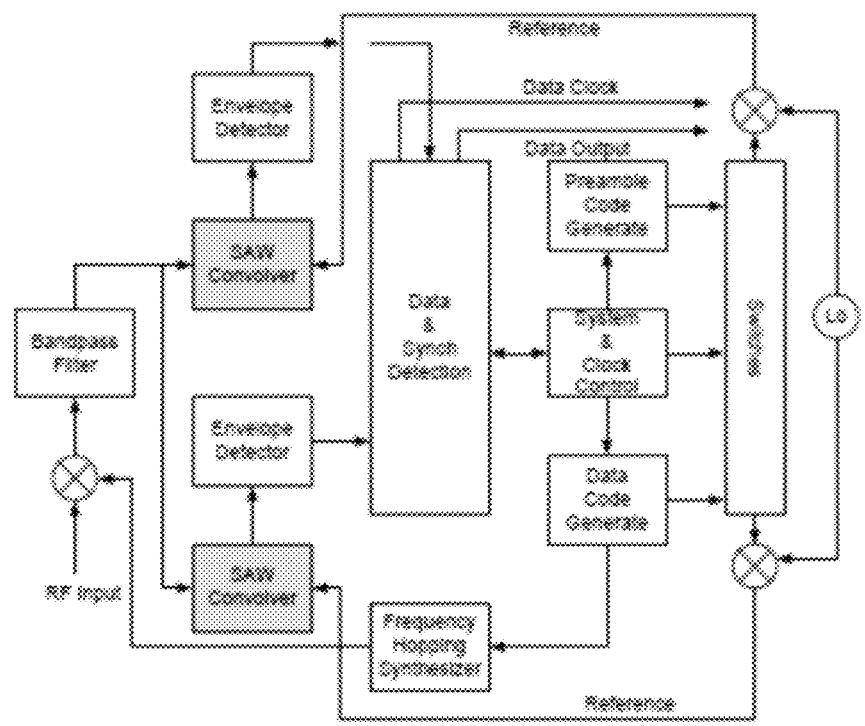

Although most of the discussion that follows relates to use of surface acoustic wave (SAW) resonators in mass sensor applications, the described embodiments for different SAW resonators also have applications in communications systems for transmission and/or receivers along with the down conversion of intermediate frequencies. In at least one embodiment, a SAW resonator is provided having an insertion loss between 0 dB and −5 dB with a very high Q, which are parameters that are important in communication systems. FIGS. 1-3B provide illustrative embodiments on how the SAW resonators disclosed in the various embodiments could be used in filters, delay lines, oscillators such as crystal oscillators, and/or convolvers in communication systems/devices. FIG. 3A illustrates an alternative embodiment where the input and output interdigital transducers (IDT) are replaced by a pair of input IDTs with a metal film located between them with the metal film attached to an output.

Based on this disclosure it should be appreciated that the disclosed SAW resonators can operate at a variety of frequencies including 0 MHz to 3.0 GHz, 1 GHz to 3.2 GHz, 1 GHz to 3.12 GHz, 800 MHz to 2.5 GHz, and 100 MHz to 1 GHz.

A. Invention Overview

Figure 4:
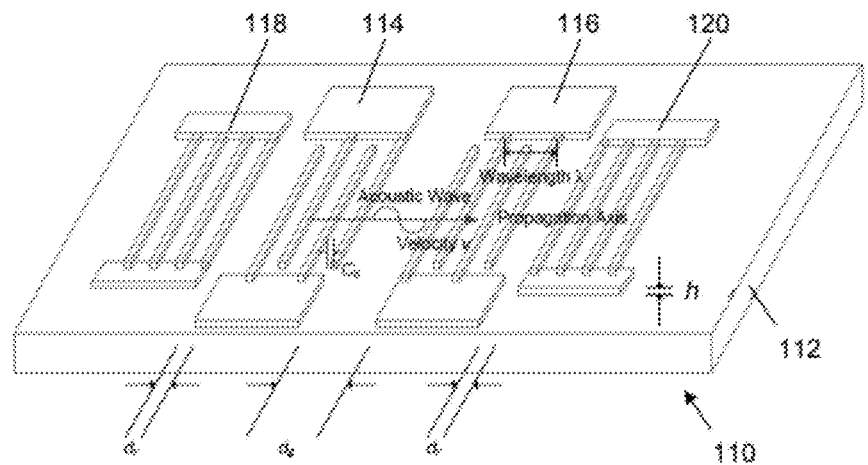
FIG. 4 illustrates an embodiment according to the invention.

As illustrated in FIG. 4, at least one embodiment of the invention includes a SAW resonator 110 having a substrate 112 with components along one surface. The illustrated SAW resonator 110 further includes an input IDT 114 (with N pair of electrodes), an output IDT 116 (with M pair of electrodes), and a pair of gratings 118, 120 (first and second gratings) located on opposing sides of the input IDT 114 and the output IDT 116. In at least one embodiment, N equals M. The input IDT 114 and the output IDT 116 in at least one embodiment are spaced from each other by a distance $d_g$ and from the nearest respective grating by a distance $d_r$. In at least one embodiment, $d_g$ equals $d_r$ (or collectively referred to as a distance L). In a further embodiment, the surfaces of the input IDT 114, the output IDT 116, and the gratings 118, 120 not connected to the substrate 112 is covered with a polymer resin 140, which then is covered at least in part by at least one biochemical coating 142 which selectively reacts with an entity under analysis.

FIG. 4 also illustrates that the wavelength of the SAW resonator 110 is λ, which is determined by the spacing of neighboring electrodes (or fingers) connected to the input signal side of the input IDT 114. The wavelength λ determines the center frequency $f_c$ for the SAW resonator 110. Also, illustrated is $C_0$ representing the width of one electrode. In at least one embodiment, the thickness h of the electrodes is 2000 Å or less. Although, the input IDT 114, the output IDT 116, and the gratings 118, 120 are illustrated as each having 4 electrodes, the number of electrodes can be any number for the gratings 118, 120 and any even number for the input IDT 114 and the output IDT 116 as will be discussed in this disclosure. FIG. 4 also illustrates that the acoustic wave produced by the input IDT 144 has a velocity v and travels on a path substantially perpendicular to the electrodes of the input IDT 114.

The substrate 112 in the described embodiments is a piezoelectric material unless noted otherwise. The material used for the substrate 112 in at least one embodiment is a single crystal cut in such a manner that waves polarized horizontally through it, i.e., the waves move substantially in planes parallel to the surface of the substrate 112 (i.e., the x-axis). Examples of suitable substrates include but are not limited to Quartz, Lithium Niobate ($LiNbO_3$), Bismuth Germanium Oxide ($Bi_{12}GeO_{20}$), Lithium Tantalite ($LiTaO_3$) and Gallium Arsenide (GaAs). In at least one embodiment the substrate 112 is $LiNbO_3$, and in yet further embodiments 128° YX $LiNbO_3$. The 128° YX $LiNbO_3$ substrate 112 has properties of high velocity v and $K^2$; however, the bidirectional SAW resonators on the high $K^2$ substrate 112 also have larger bandwidth and lower Q factors. In telecommunication applications, the bidirectional SAW resonators on a 128° YX $LiNbO_3$ substrate 112 are most often used as wideband midloss intermediate frequency (IF) resonators and as wideband filters. The escaped acoustic waves in bidirectional SAW resonators are reflected by the shorted reflectors in the gratings 118, 120, which not only improves the Q factor; but also the insertion loss in the receiving output IDT 116.

Figure 1:
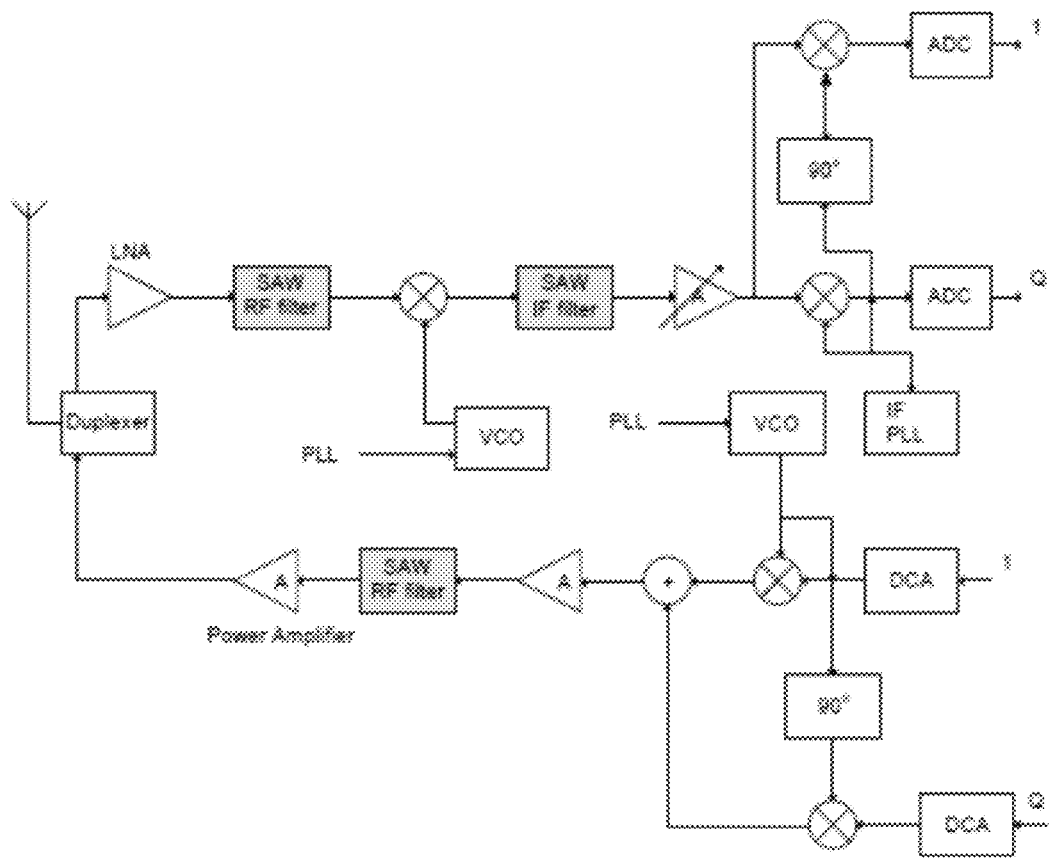
FIG. 1 illustrates an example block diagram depicting surface acoustic wave (SAW) resonators used as filters for radio frequency and/or intermediate frequency in a GSM transceiver.
Figure 2:
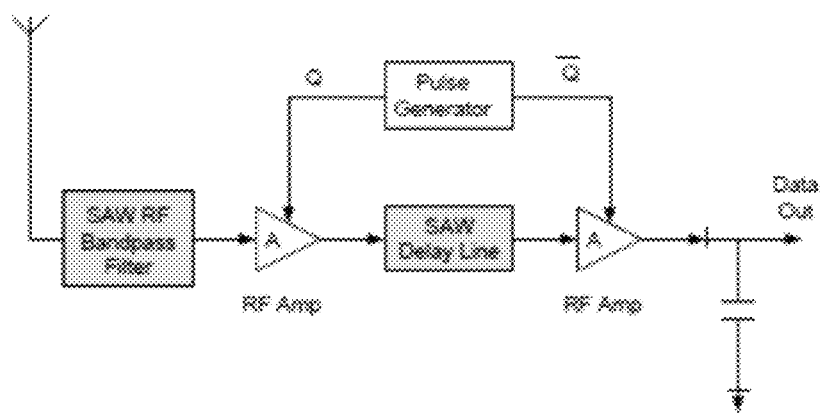
FIG. 2 illustrates an example block diagram depicting SAW resonators used as a bandpass filter and a delay line in a wireless receiver.
Figure 5:
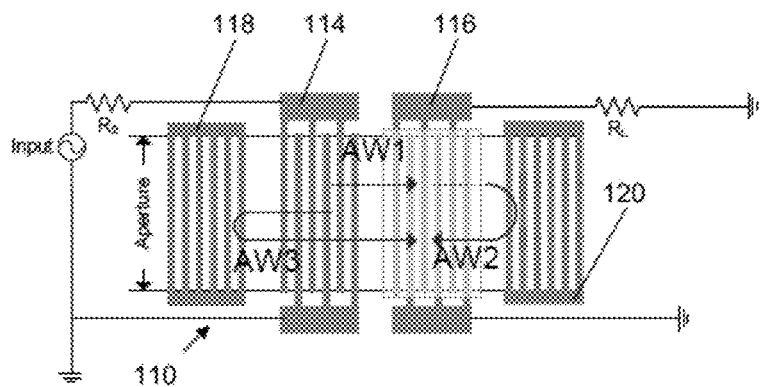
FIG. 5 illustrates a single-track SAW resonator with shorted gratings including directions of acoustic waves.
Figure 6:
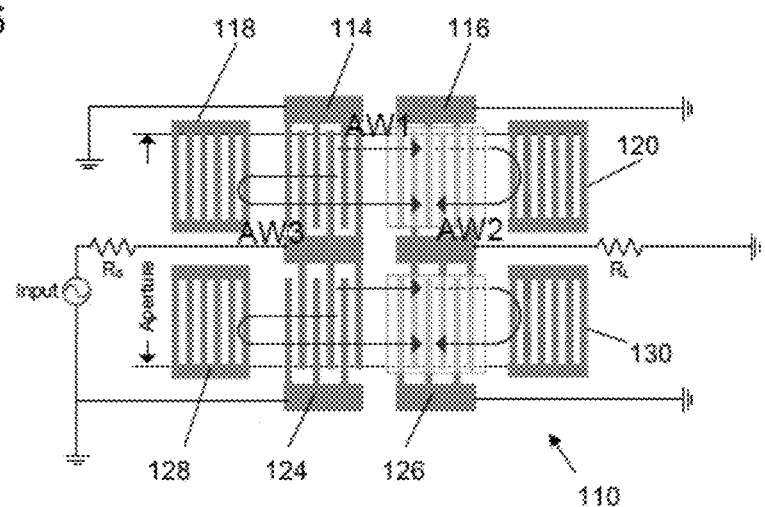
FIG. 6 illustrates a parallel track SAW resonator with shorted gratings including directions of acoustic waves.

The geometry of two one-pole synchronous resonators is illustrated in FIGS. 5 and 6. The separation between input and output IDTs was minimized to the shortest distance ($d_g=\lambda/2$) so that the propagating loss and phase shift due to the free space between the two IDTs can be minimized. In at least one further embodiment, the distance $d_g$ is a multiple of $\lambda/2$ (i.e., $i\lambda/2$ where i is an integer equal to or greater than 1). The gap distance $d_g$ is measured from the centers of the closest finger of one IDT to the other IDT and its similarly situated finger as illustrated in FIG. 1. Acoustic waves excited by input IDT 114; however, are bidirectional and half the acoustic waves propagate away from the output IDT 116 (see, e.g., AW3), which causes the loss in the transmission line, towards the gratings, which are illustrated in FIGS. 4-6 as shorted reflectors on the opposite side of the input IDT 114 from the output IDT 116. In order to improve this, the shorted reflectors are employed to reflect the acoustic waves back to the output IDT 116 as illustrated in FIGS. 5 and 6 (see AW2 and AW3).

Each IDT includes multiple pairs of fingers (or electrodes) that are spaced apart. A variety of metals as known in the art may be used for fabricating the fingers including, for example, but not limited to Aluminum, Gold, or other conductive metals. The fingers in at least one embodiment are spaced apart one-half of the desired wavelength as measured from their centers to obtain the desired frequency for use in the device. In at least one embodiment, the fingers have a width of one quarter of a wavelength ($\lambda/4$). In at least one embodiment, the metallization η is 0.5. In at least one embodiment, the fingers have a thickness h equal to approximately 2000 Å.

In at least one embodiment, the metal used to create the fingers is also used to create the shorted reflectors; however, a different metal could be used for the shorted reflectors. In at least one embodiment, the reflectors are stacked horizontally along the surface of the piezoelectric with no gaps present between neighboring shorted reflectors. The number of reflectors can be any number from 100 to infinity or between 10 and 150 in each reflector set. Additional examples of the number of layers include, but are not limited to, any number between 15 and 100, 15, and 100. In a further embodiment, the number of reflectors can be any number as space permits in a particular implementation. In a further embodiment, the space between neighboring reflectors is $\lambda/4$ as illustrated in FIG. 40B.

FIG. 7 shows the relationship between the number of single-electrode fingers and the power of the reflecting waves. The reflectors were designed with 100 electrodes and placed next to the input and output IDTs, which resulted in a near 100% reflection. FIGS. 5 and 6 (these figures omit the substrate 112) illustrate the propagating acoustic waves and reflecting acoustic waves in the SAW resonators. There are two transitions of the acoustic waves. The first transition AW1 is the propagating acoustic waves which travel to the output IDT 116 directly from the input IDT 114 and are converted into electrical signals. The second transition AW2 is the reflecting acoustic waves which are the acoustic waves passed through the output IDT 116 and reflected from the grating 120 back to the output IDT 116. The escaped acoustic waves AW3 from the input IDT 114 are reflected back by the grating 118 to the output IDT 116 and propagated though the input IDT 114. The 100 electrodes were chosen to reflect the entire wave back to the IDT according to FIG. 7.

In at least one embodiment, the distance between the gratings 118, 120 and the nearest IDT is one-half of a wavelength ($d_r=1/2\lambda$). In at least one further embodiment, the distance $d_g$ is a multiple of $\lambda/2$ (i.e., $i\lambda/2$ where i is an integer equal or greater than 1). This spacing allows for the two reflecting acoustic waves received at the output IDT 116 to have an asymmetric resonance with a 90° phase shift in the center frequency. The resonance from the second transition AW2, AW3 of acoustic waves is superimposed on the resonance from the first transition AW1. This superimposed resonance not only increases the insertion loss, but also provides a one-pole response in the center frequency. FIGS. 5 and 6 also illustrate that the aperture is based on the length of the electrode pairs and that half of each electrode pair is connected to ground.

FIG. 5 illustrates a single track SAW resonator 110 with an input IDT 114 and an output IDT 116 each having N pairs of fingers and two gratings 118, 120 each having a set of shorted reflectors. The input IDT 114, the output IDT 116, and the gratings 118, 120 are aligned along a pathway followed by the by the acoustic waves produced by the input IDT 114. The input provides the input electrical signal to the input IDT 114 to create the acoustic waves to be received by the output IDT 116 and reflected by the gratings 118, 120. Resistors $R_S$ and $R_L$ are illustrated to show the presence in at least one embodiment of resistors on the input and output sides of the SAW resonator 110.

FIG. 6 illustrates a parallel set of SAW resonator components including a second input IDT 124, a second output IDT 126, a third grating 128, and a fourth grating 130, which are aligned along a second pathway followed by the acoustic waves produced by the second input IDT 124. As illustrated, the input and output are taken in the center between the two parallel sets of SAW resonator components with the external ends being connected to ground. FIGS. 5 and 6 also illustrates the presence of resistors $R_S$ and $R_L$ along with an Input source.

FIGS. 8-10 illustrate an enclosure that can be used in connection with the various SAW embodiments in this disclosure. FIG. 9 depicts a parallel track one-pole synchronous SAW mass sensor 110'. The illustrated enclosure includes a housing 810, a pair of SMA connectors 820, and a lid 812.

Although the housing 810 is illustrated as being a channel structure, the housing 810 could however take other forms depending in part on the shape of the SMA connectors 820. Together the housing and the SMA connectors 820 define a cavity 814 in which the SAW resonator 110 on a support member 830 is able to reside. The SMA connectors 820 as illustrated include a connector 822, support member holders (or mounting member) 824 for holding the SAW resonator 110, and a connection wire 826 for connection to traces 832 present on a chip (or support member) 830 supporting the SAW resonator 110. In at least one embodiment, the traces 832 are present on the substrate 112. One of ordinary skill in the art will appreciate based on this disclosure that a variety of different connectors could be used in place of the illustrated SMA connectors 820 including different variants of SMA connectors 820 while still providing a connection between the SAW resonator 110 and external equipment (e.g., network analyzer), controller, and/or circuits. The lid 812 is illustrated as being a cover, but in other alternative embodiments the lid 812 may be hinged as illustrated in FIG. 10, tethered, or otherwise connected to the housing. In at least one embodiment according to the invention, the sensing area for a 121 MHz SAW resonator is 1.6 mm×2.0 mm and the sensing area of a 978 MHz SAW resonator is 0.4 mm×0.2 mm.

FIGS. 11 and 12 illustrate an alternative structure for supporting a SAW mass sensor 110' and a calibration SAW resonator 110 as with the previous embodiment the variously described SAW embodiments of this disclosure may be used in connection with the illustrated structure. The structure illustrated includes a channel support structure 1110 with a transverse support member 830', which as illustrated is a microscope slide but other material or items could be used in place of the slide. The support member 830' provides support to the SAW mass sensor 110' and the calibration SAW resonator 110 and the trace lines 832 providing the connection points to external equipment via the illustrated SMA connectors 820. There are two sets of SMA connectors 820 (an input side 820a, 820c and an output side 820b, 820d) with one set for the SAW mass sensor 110' and the second set for the calibration SAW resonator 110. The structure further includes a plastic well 132 sitting atop the SAW mass sensor 110' to provide a place for any coatings and/or material to be analyzed. See discussion later regarding SAW mass sensor experiment with a polymer and potassium chloride (KCL) for an example of use of this structure. The illustrated pipette 1160 (or similar delivery mechanism) may be used to deliver the material to create the polymer or provide the material to be analyzed.

FIG. 13 illustrates a further embodiment according to the invention that includes a controller 1308 that is in electrical communication with a first connector 822a and a second connector 822b. The controller 1308 provides an input signal through the first connector 822a to the input IDT(s) 114, 124 to create an acoustic wave(s) in the substrate 112 to be received by the output IDT(s) 116, 126. The output electrical signal from the output IDT(s) 116, 126 is sent to the second connector 822b to be transmitted to the controller 1308. The controller 1308 detects any change or difference in the frequencies between the input electrical signal and the output electrical signal.

In a further alternative embodiment according to the invention, FIGS. 14-16 illustrate any of the above described SAW embodiments with the addition of a polymer layer 140 overlaying the SAW resonator 110, while FIG. 17 illustrates a further biochemical coating 142 above the polymer layer 140. As described in the testing discussion at the end of this disclosure, the polymer layer 140 provides protection to the SAW resonator 110 and prevents them from being shorted out by the presence of a fluid. Suitable polymers include any polymer that will provide a fluid sealing layer around the components while having a thickness ($h_p$) of a few angstroms, which in at least one embodiment the thickness of the polymer $h_p$ is substantially less than the height of the input and output IDT fingers h. Polyvinyl chloride (PVC) was used in experiments to determine its impact on the sensitivity of a SAW resonator 110, and it was found to have an acceptable impact on the sensitivity while substantially avoiding insertion loss. The biochemical coating 142 in at least one embodiment is a thin layer of gold, but could be any coating that selectively reacts with an entity under analysis such as acting as an analyte capture binding surface. Further examples of the biochemical coatings can be found in U.S. Pat. Pub. No. 2009/0124513 listing Berg et al. as inventors, this publication is hereby incorporated by reference for its teachings regarding biological coatings. In at least one embodiment, the biochemical coating includes a plurality of islands, nanowires, and/or nanoparticles attached to the capture binding material.

FIG. 18 illustrates an alternative embodiment according to the invention. The device illustrated in FIG. 18 includes any of the above described SAW resonators 110 with the addition of a chamber 1800 in which the SAW resonator 110 resides on top of a heating plate 1802. The chamber 1800 having a plurality of walls and a floor with further embodiments including a lid. The illustrated chamber 1800 further includes a fan 1804 residing in an opening along one wall of the chamber 1800 and a temperature sensor 1806 that provides a signal to a controller 1808 for controlling the operation of the heating plate 1802 and the fan 1804. This embodiment is advantageous for controlling the temperature in the chamber 1800 to maintain a constant temperature during use of the SAW resonator 110 by providing heat and/or cooling to counteract any temperature changes within the chamber 1800. In a further embodiment, the heating plate 1802 is incorporated into the support structure 1110 illustrated in FIG. 11.

FIG. 19 also illustrates a slightly different alternative embodiment according to the invention. As illustrated in FIG. 19, this embodiment includes any of the above described SAW embodiments operating in parallel. One SAW resonator 110' is used for testing (if the well 130 is present) or as a filter (otherwise), while the second SAW resonator 110 acts as a control reference. As both SAW resonators 110, 110' are exposed to the same environment including temperature and humidity changes, the difference between the respective signals from the output IDTs from the two SAW resonators 110, 110' can be compared by the controller 1308 to determine whether there has been a frequency shift as a result of an analytical testing session. The controller 1308 provides an input electrical signal to the input IDTs of the SAW resonators 110', 110 via first and third connectors 820a, 820c to produce acoustic waves in the respective SAW resonators. The SAW resonators 110', 110 provide output signals back to the controller via second and fourth connectors 820b, 820d, respectively.

Table 1 in Section B shows that a 128° YX LiNbO$_3$ substrate has a high temperature coefficient (75 ppm/° C.), which is related to the velocity of the acoustic waves. With an increase in temperature, it causes the downward shift of the center frequency. If the temperature increases 1° C., then the center frequency shifts 13.3 KHz. Temperature stability is an important factor for using SAW resonators as narrowband filters, oscillators and mass sensors. As discussed above in at least one embodiment, the SAW resonator sits on a 128° YX LiNbO$_3$ substrate to provide a mass sensor. As discussed in Section D, the device had a frequency shifts when the mass was deposited on the electrodes. If the temperature is changing during the measurement, the factors of temperature changes have to be considered when measuring the center frequency to shift at the same time. Both of the alternative embodiments illustrated in FIGS. 18 and 19 are able to address this issue if necessary; however, as discussed later when testing devices built according to the invention (see Section D) there was negligible temperature shift during use.

B. Underlying Research

The following paragraphs and sections will discuss the development of some of the above-described embodiments along with experiments that were simulated and conducted in connection to embodiments built according to the invention.

To provide a better understanding of the characteristic of the SAW resonator on the 128°YX $LiNbO_3$ substrate, a model was developed to convert the energy between electric signals to mechanical waves. The cross-field model (also known as the Mason model) can obtain the radiation conductance parameters in the transmission of a SAW resonator yielding information on the frequency response and insertion loss, including input and output impedances. The cross-field model was employed for modeling SAW resonators on the 128° YX $LiNbO_3$ substrate. The cross-field model yields a better agreement than other models in the frequency response for the IDTs on the high-$K^2$ piezoelectric substrates.

In at least one embodiment, 128°YX $LiNbO_3$ was selected as the substrate 112, because the coupling between the electrical and mechanical energy is the highest in Table 1. In the practical design of SAW resonators, there are many factors affecting the performance. The most important parameters in SAW resonators are summarized as the following: (1) the space $d_a$ between the adjacent IDTs; (2) the space $d_r$ between the IDT and the reflector; (3) reflectivity and loss; (4) the number of IDT fingers; (5) IDT thickness and resistivity; (6) electromechanical coupling constant $K^2$ and the capacitance $C_0$ value of each finger pair; and (7) the operating frequency $f_o$. These important parameters will be discussed in the following paragraphs.

FIG. 20 shows how acoustic waves are excited by applying a voltage on the electrodes in the input IDT. These acoustic waves cause displacement and a potential difference on the surface of piezoelectric material (or substrate). The frequency of acoustic waves is governed by the periodic electrodes of IDT and the acoustic velocity of the piezoelectric material. The equation for velocity is shown in Equation 1.

$$v = \lambda_1 \times f_1 \qquad \text{Equation 1}$$

where $\lambda_1$ is the wavelength in the first harmonic frequency and $f_1$ is the center frequency.

In FIG. 20, there is more than one harmonic wave propagating along the surface between the electrodes. The wavelength of the $n^{th}$ harmonic frequency is defined in terms of in Equation 2. FIG. 21 shows the first harmonic frequency $f_1$ and second harmonic frequency $f_2$ for the IDT electrodes shown in FIG. 20.

For the second harmonic wavelength $\lambda_2$, the following equation applies $$\frac{1}{4}\lambda_1 = \frac{1}{4}\lambda_2 + \lambda_2 \qquad \text{Equation 2}$$

For the $n^{th}$ harmonic wave length $\lambda_n$, the following equation applies $$\frac{1}{4}\lambda_1 = (n-1)\lambda_n + \frac{1}{4}\lambda_n \qquad \text{Equation 3}$$

$$\lambda_n = \frac{1}{(4n-3)}\lambda_1$$

$$f_n = (4n-3)f_1, n > 2 \qquad \text{Equation 4}$$

where $\lambda_2$ is the wavelength of the second harmonic, $f_2$ is the frequency of the second harmonic, $\lambda_n$ is the wavelength of the $n^{th}$ harmonic, and $f_n$ is the frequency of the $n^{th}$ harmonic.

For the next part of this discussion, to facilitate an understanding of the present invention, a conventional SAW resonator will be described and includes input and output IDTs on the piezoelectric material, but no gratings. The input IDTs are the source of the acoustic waves illustrated in FIGS. 22A and 22B with the second (or right) illustrated IDT being the output IDT. This type of bidirectional SAW resonator is depicted in FIGS. 22A (single SAW resonator) and 22B (parallel SAW resonator) and includes uniform finger spacing and constant finger overlap in the input/output IDTs. When the input IDT is stimulated by AC signals in its frequency range, the surface acoustic waves propagate outward in two directions along the propagation axis. The acoustic waves propagating toward the output IDT generate the electric charge distribution at the output IDT; however, only half of the power in maximum received by the output IDT. The other half power from the input IDT becomes a power loss due to the escaped acoustic waves. These escaped acoustic waves cause a frequency response with a low insertion loss (<–6 dB or <20 log 0.5).

In order to model the bidirectional SAW resonator, the cross-field model is employed to translate the SAW resonator into a two port equivalent circuit. The cross-field model yields a better agreement for the SAW resonator on the high-$K^2$ piezoelectric material, such as 128°YX $LiNbO_3$. In the adaption of cross-field model, the input and output IDTs can be represented as three-port networks. In FIG. 23, Ports 1 and 2 are acoustic ports which generate the acoustic waves along the opposite propagation axis. Port 3 is an electrical port of input or output signals. When the input and output IDTs are placed next to each other, the acoustic waves from the Port 2 of the input IDT propagate into the Port 1 of the output IDT. The acoustic signals are transmitted in the transmission line between the input and output IDTs as shown in FIG. 23. In order to reduce the loss in the transmission line, the separation between the input and output IDTs is equal to the minimum distance ($d_g = \lambda/2$). The fingers in the output IDT are also placed synchronously on the maximum displacement in the Z axis of the acoustic waves.

In the cross-field model, the acoustic waves in Port 1 and Port 2 are converted into the equivalent electrical parameters. The three-port network of a single IDT is translated to an admittance matrix. As shown in FIG. 24, the $R_S$ represents input resistors. $G_0$ is the equivalent electrical characteristic conductance in the transmission line. $C_T$ is the total capacitance between fingers in the IDT. The three-port network is expressed as a 3×3 admittance matrix [Y].

The current-voltage relations $$\begin{bmatrix} I_1 \\ I_2 \\ I_3 \end{bmatrix} = [Y] \begin{bmatrix} V_1 \\ V_2 \\ V_3 \end{bmatrix} = \begin{bmatrix} Y_{11} & Y_{13} & Y_{13} \\ Y_{12} & Y_{11} & -Y_{13} \\ Y_{13} & -Y_{13} & Y_{33} \end{bmatrix} \begin{bmatrix} V_1 \\ V_2 \\ V_3 \end{bmatrix} \qquad \text{Equation 5}$$

where the admittance matrix Y is explained as $$\begin{bmatrix} Y_{11} & Y_{13} & Y_{13} \\ Y_{12} & Y_{11} & -Y_{13} \\ Y_{13} & -Y_{13} & Y_{33} \end{bmatrix}$$

$$Y_{11}(f) = -jG_0\cot(N\Theta) = -jK^2 f_0 C_S \cot\left(N \cdot 2\pi\left(\frac{f}{f_0}\right)\right) \quad \text{Equation 6}$$

$$Y_{12}(f) = jG_0\csc(N\Theta) = jK^2 f_0 C_S \csc\left(N \cdot 2\pi\left(\frac{f}{f_0}\right)\right) \quad \text{Equation 7}$$

$$Y_{13}(f) = -jG_0\tan\left(\frac{\Theta}{4}\right) = -jK^2 f_0 C_S \tan\left(\frac{2\pi\left(\frac{f}{f_0}\right)}{4}\right) \quad \text{Equation 8}$$

$$Y_{33}(f) = j4NG_0\tan\left(\frac{\Theta}{4}\right) + j\omega C_T = \quad \text{Equation 9}$$

$$j4NK^2 f_0 C_S \tan\left(\frac{2\pi\left(\frac{f}{f_0}\right)}{4}\right) + j2\pi f_0 C_T$$

where $K^2$ is electromechanical coupling constant, $f_0$ is the IDT center frequency, $C_S$ is the static capacitance of one periodic section, $C_T$ is the total IDT capacitance, $G_0$ is the equivalent characteristic admittance, $\theta$ is the electrical transit angle, and N is the total number of fingers.

The three-port Y admittance of the input and output IDTs are shown in FIG. 25. The input voltage can be expressed as $V_{in}=V_1+I_a R_S$, where $R_S$ is the source resistance. The output voltage $V_L$ can be expressed as $V_L=V_b$. The currents of $I_a$ and $I_b$ are shown in Equation 10. From Equations 10 and 11, the transfer function H(f) of input and output voltage is obtained in Equation 12.

The current-voltage relation is $$\begin{cases} I_a = y_{aa}V_a + y_{ab}V_b & \text{(at input)} \\ I_b = y_{ba}V_a + y_{bb}V_b & \text{(at output)} \end{cases} \quad \text{Equation 10}$$

The input, output and transfer admittances are $$\begin{cases} y_{aa} = \left.\frac{I_a}{V_a}\right|_{V_b=0} & \text{(at input)} \\ y_{bb} = \left.\frac{I_b}{V_b}\right|_{V_a=0} & \text{(at output)} \\ y_{ba} = \left.\frac{I_b}{V_a}\right|_{V_b=0} & \text{(input-to-output)} \\ y_{ba} = y_{ab} \end{cases} \quad \text{Equation 11}$$

The transfer function becomes $$H(f) = \frac{V_L}{V_{in}} = \frac{y_{ab}R_L}{(1+y_{aa}R_S)(1+y_{bb}R_L) - y_{ab}^2 R_S R_L} \quad \text{Equation 12}$$

The two-port equivalent circuit can be converted from FIG. 25 to FIG. 26. The output IDT is excited by a high-impedance current source. The Y admittances defined in Equation 11 can be simulated by using sinc function $$\left(\left|\frac{\sin x}{x}\right|\right)$$

instead of tan $$\left(\frac{\Theta}{4}\right).$$

So the input admittance $y_{aa}$ of the two-port equivalent circuit is shown in Equation 14 when the output IDT is shorted circuit, and $y_{bb}$ is the output admittance in term of M finger pairs in the output IDT. The third term $y_{ab}$ in Equation 16 is transfer admittance, including input and output parameters, where $\phi$ is a phase parameter of the separation between the input/output IDTs' phase centers. The insertion loss (IL) in Equation 17 using Y admittances and source/load resistance is the ratio of power received at the load resistance to the maximum available power from the source.

The radiation conductance is $$G_a(f) \approx 8K^2 f_0 C_S N^2 \left|\frac{\sin\left[\frac{N\pi(f-f_0)}{f_0}\right]}{\left[\frac{N\pi(f-f_0)}{f_0}\right]}\right|^2 \quad \text{Equation 13}$$

The input admittance is $$y_{aa} = Y_{33}(f) \approx G_a(f) + j2\pi f_0 C_T \approx \quad \text{Equation 14}$$

$$8K^2 f_0 C_S N^2 \left|\frac{\sin\left[\frac{N\pi(f-f_0)}{f_0}\right]}{\left[\frac{N\pi(f-f_0)}{f_0}\right]}\right|^2 + j2\pi f_0 C_T$$

The output admittance is $$y_{bb} = Y_{33}(f) \approx G_a(f) + j2\pi f_0 C_T \approx \quad \text{Equation 15}$$

$$8K^2 f_0 C_S M^2 \left|\frac{\sin\left[\frac{M\pi(f-f_0)}{f_0}\right]}{\left[\frac{M\pi(f-f_0)}{f_0}\right]}\right|^2 + j2\pi f_0 C_T$$

The transfer admittance is $$y_{ab} = Y_{13}(f)Y_{13}(f) \approx 8K^2 f_0 C_S NM \left|\frac{\sin\left[\frac{N\pi(f-f_0)}{f_0}\right]}{\left[\frac{N\pi(f-f_0)}{f_0}\right]}\right| \quad \text{Equation 16}$$

$$\left|\frac{\sin\left[\frac{M\pi(f-f_0)}{f_0}\right]}{\left[\frac{M\pi(f-f_0)}{f_0}\right]}\right| e^{j[\pi(1-(N+M)(f-f_0)/f_0)-\phi]}$$

The insertion loss is $$IL = 20\log_{10}\frac{P_{out}}{P_{in}} =$$ Equation 17

$$-20\log_{10}\left|\frac{[(1+y_{aa}R_S)(1+y_{bb}R_L)-y_{ab}R_S R_L]\sqrt{\frac{R_L}{R_S}}}{2R_L y_{ab}}\right|$$

where $G_a(f)$ is the radiation conductance, N is the number of input IDT finger pairs, M is the number of output IDT finger pairs, and $\phi$ is the phase parameter of the separation between IDT phase centers.

The insertion loss based on Equation 17 was simulated in MATLAB and shown in FIG. 27. The center frequency is 121 MHz when the number of finger pairs is 30 for the input and output IDTs. The maximum insertion loss is −14.3124 db which occurs in the center frequency. The insertion loss is much higher than −6 dB due to its bidirectional IDT structures. As mentioned previously, half the power from the input IDT is not received by the output IDT, because no reflectors are present. According to the simulation results in FIG. 27A, the bandwidth is 2.7 MHz which results in a low Q factor (Q=45).

The piezoelectric properties are important factors in SAW designs and the cross-field model. The illustrative embodiments in this disclosure use a 128° YX LiNbO$_3$ substrate as the piezoelectric medium for the acoustic waves. It is the piezoelectric crystal substrates that can generate surface acoustic waves. The high electromechanical coupling coefficient $K^2$ of 128° YX LiNbO$_3$ can improve the efficiency in converting mechanical waves to electrical signals in the receiving IDT; however, lithium niobate crystals have a nonzero temperature coefficient.

The most practical properties related to the surface acoustic waves are the velocity v and electromechanical coupling coefficient $K^2$. The velocity v is related to the speed of the acoustic waves and the center frequency $f_o$ of SAW resonators. The $K^2$ is the efficiency in converting the applied electrical signals into the mechanical energy of the acoustic waves. It is also related to the maximum insertion loss of two-port SAW resonators. Table 1 lists the properties of common piezoelectric substrates. 128° YX LiNbO$_3$ has high velocity (3992 m/s) and $K^2$ (5.3%). These two properties yield to a higher center frequency and insertion loss than other piezoelectric materials. FIG. 28 shows the MATLAB simulation of the insertion loss versus finger pairs of the equivalent circuit depicted in FIG. 26. The insertion loss can be calculated using Equation 17. A MATLAB simulation based on the theoretic model of the bidirectional SAW resonators depicted in FIGS. 22A and 22B for the different materials listed in Table 1 was run. The high $K^2$ materials, like 128° YX LiNbO$_3$ or LiTaO$_3$, have higher insertion loss than the low $K^2$ materials as shown in FIG. 27B.

TABLE 1

| Material | Crystal Cut | SAW Axis | Velocity (m/s) | $K^2$ (%) | Temp Coefficient (ppm/° C.) | Capacitance/Finger Pair/Unit Length $C_o$ (pF/cm) |
|---|---|---|---|---|---|---|
| Quartz | ST | X | 3158 | 0.11 | ~0 near 25° C. | 0.55 |
| Lithium Niobate LiNbO$_3$ | Y | Z | 3488 | 4.05 | 94 | 4.6 |
| LiNbO$_3$ | 128° | X | 3992 | 5.3 | 75 | 5.0 |
| Bismuth Germanium Oxide | 110 | 001 | 1681 | 1.4 | 120 | — |
| Lithium tantalite LiTaO$_3$ | 77.1° rotated | Z' | 3254 | 0.72 | 35 | 4.4 |
| Gallium arsenide GaAs | 110 | <110> | <2841 | <0.06 | 35 | — |

FIG. 27B shows the relationship between the insertion loss and finger pairs on the 128° YX LiNbO$_3$ substrate from simulations of bidirectional SAW filters from FIGS. 22A and 22B based on the cross-field model. The maximum insertion loss increases while the number of finger pairs in the input/output IDTs increases. This increase becomes saturated after the finger pairs are greater than 20.

The previous cross-field model was modified to include the superimposed reflecting acoustic waves from the use of gratings as discussed in Section A. This results in a new equation for the insertion loss. The radiation conductance is expressed $G_a(f)$ as a sinc function in the center frequency $f_a$. The equivalent circuit can be expressed by the Y admittance function of $G_a(f)$ and $C_{T \cdot y_{aa}}$ is the input admittance when the output IDT is short-circuited. In the same way, the output admittance $y_{bb}$ can be obtained when the input IDT is short-circuited. The remaining term $y_{ab}$ is the transfer admittance involving both input and output parameters. $\phi$ is a phase between input and output IDT. The insertion loss for SAW resonators can be defined based on Y admittance involving the source and load resistance $R_S$ and $R_L$. The one-pole synchronous resonators have another resonance/acoustic waves superimposed in the center frequency. This superimposed resonance in the center frequency is generated by the reflecting acoustic waves in the output IDT. The propagating waves are reflected back to the output IDT by the shorted reflectors as discussed previously. These reflecting waves generate the second resonance with 90° phase shift in the center frequency as discussed above. The additional resonance results in an asymmetric frequency response due to 90° phase shift, with the increase in insertion loss as well as the lower upper stop band as shown in FIG. 29. This additional resonance can also have a near-match (50 ohm) at the center frequency. The superimposed resonance can be simulated by using another sinc function $$\left|\frac{\sin(x)}{x}\right|^2$$

and a phase θ as shown in Equation 21.

The input admittance is $$y_{aa} = Y_{33}(f) \approx G_a(f) + j2\pi f_0 C_T \approx \qquad \text{Equation 18}$$

$$8K^2 f_0 C_S N^2 \left|\frac{\sin\left[\frac{N\pi(f-f_0)}{f_0}\right]}{\left[\frac{N\pi(f-f_0)}{f_0}\right]}\right|^2 + j2\pi f_0 C_T$$

The output admittance is $$y_{bb} = Y_{33}(f) \approx G_a(f) + j2\pi f_0 C_T \approx \qquad \text{Equation 19}$$

$$8K^2 f_0 C_S M^2 \left|\frac{\sin\left[\frac{M\pi(f-f_0)}{f_0}\right]}{\left[\frac{M\pi(f-f_0)}{f_0}\right]}\right|^2 + j2\pi f_0 C_T$$

The transfer admittance is $$y_{ab} = Y_{13}(f)Y_{13}(f) \approx 8K^2 f_0 C_S NM \left|\frac{\sin\left[\frac{N\pi(f-f_0)}{f_0}\right]}{\left[\frac{N\pi(f-f_0)}{f_0}\right]}\right| \qquad \text{Equation 20}$$

$$\left|\frac{\sin\left[\frac{M\pi(f-f_0)}{f_0}\right]}{\left[\frac{M\pi(f-f_0)}{f_0}\right]}\right| e^{j[\pi(1-(N+M)(f-f_0)/f_0)-\phi]}$$

The insertion loss becomes $$IL = \left(20\log_{10}\left|\frac{\left[(1+y_{aa}R_S)(1+y_{bb}R_L) - \right]\sqrt{\frac{R_L}{R_S}}}{2R_L y_{ab}}\right|\right) \times \qquad \text{Equation 21}$$

$$\left[1 + \left(\left|\frac{\sin\left[\frac{N^2\pi(f-f_0)}{f_0}\right]}{\left[\frac{N^2\pi(f-f_0)}{f_0}\right]}\right|^2 - \left|\frac{\sin\left[\frac{N^2\pi(f-f_0)}{f_0} - \Theta\right]}{\left[\frac{N^2\pi(f-f_0)}{f_0} - \Theta\right]}\right|^2\right)\right]$$

where $G_a(f)$ is the radiation conductance, N is the number of input IDT finger pairs, M is the number of output IDT finger pairs, φ is the phase parameter of the separation between DT's phase centers, and θ is the phase shift of second resonance in the center frequency.

The frequency response based on the distance parameters in FIGS. 5 and 6 and Equation 21 was simulated in MATLAB. FIG. 29 shows a one-pole resonance superimposed in the center frequency. This superimposed resonance is simulated by using sinc function $$\left|\frac{\sin(x)}{x}\right|^2$$

with a 90° phase shift. It results in a symmetric response in the center frequency (approximately 121 MHz) with an increase in the maximum insertion loss of −4.86 dB and Q factor of 4.16 as shown in FIG. 29. There is also a deep notch in the upper stop band due to the 90° phase shift. In this simulation, the width of the electrodes is 8 μm, which yields a center frequency of 121 MHz. There are 30 finger pairs in the input and output IDT and the separation between input/output IDTs is equal to the minimum distance (e.g., λ/2).

The finite element method (FEM) is a numerical technology used to find the approximation in complicated domains. FEM is used to analyze the surface acoustic waves on the piezoelectric substrate. The AC electrical signals simulate the piezoelectric substrate and generate the stress-strain distributions on the surface. The displacements of surface acoustic waves can be modeled and visualized in FEM simulations. As part of the underlying research, two FEM software programs were used: COMSOL and CoventorWare. These programs provide the simulations of the displacements in the frequency and time domains.

The deformation of the 128° YX LiNbO$_3$ substrate was simulated by COMSOL. COMSOL is commercial software that can simulate and model a physics-based system. It can simulate the conversion between electrical signals and mechanical waves on the surface. In FIG. 30, the crystal structures in the 128° YX LiNbO$_3$ substrate show extrusions and expansions. These deformations of the substrate show the disturbances on the surface when acoustic waves propagate across it. It also generates a potential charge due to its piezoelectric property. The harmonic frequency in this simulation is 121.758 MHz based on the properties in Table 2. This simulation shows that the acoustic waves propagate along the X axis on the surface of the LiNbO$_3$ substrate, but there are no vibrations in the other directions.

TABLE 2

| | |
|---|---|
| Density (10$^3$ Kg m$^{-3}$) | 4.646 |
| Elastic stiffness (10$^{-11}$ Nm$^{-2}$) | $C^E_{11}$ = 2.424 $C^E_{12}$ = 0.752 $C^E_{13}$ = 0.752<br>$C^E_{22}$ = 2.03 $C^E_{23}$ = 0.573 $C^E_{25}$ = 0.085<br>$C^E_{33}$ = 2.03 $C^E_{35}$ = −0.085 $C^E_{44}$ = 0.752<br>$C^E_{46}$ = 0.085 $C^E_{55}$ = 0.595 $C^E_{66}$ = 0.595 |
| Piezoelectric strain coefficient (10$^{-12}$ C/N) | $d_{11}$ = 1.33 $d_{12}$ = 0.23 $d_{13}$ = 0.23<br>$d_{24}$ = −2.5 $d_{26}$ = 3.7 $d_{32}$ = −2.5<br>$d_{33}$ = 2.5 $d_{35}$ = 3.7 |

Table 2 shows the matrixes of the stiffness and piezoelectric strain of 128° YX LiNbO$_3$ and defines the properties of 128° YX LiNbO$_3$ in the COMSOL and CoventorWare simulations.

The structures of the one-pole synchronous resonators were simulated by using Coventorware to examine acoustic waves on the 128° YX LiNbO$_3$ substrate. The elastic stiffness and piezoelectric strain coefficients of the 128° YX LiNbO$_3$ in Coventorware are shown in Table 2 above. The steps of fabrication in the simulations are identified in Table 3 (shows the depositing and etching processes in Coventorware) and the 3D models of SAW resonators are based on the layouts and steps identified in Table 3. After the 3D models were built, they were meshed by using the Manhattan brick method. The meshed model of SAW resonators was simulated in the time domain and frequency domain. The electrical signals are connected to the input IDT to generate potential differences on the surface. These potential differences excite the piezoelectric material and cause the displacements of acoustic waves in the Z direction. These acoustic waves spread out on the surface and gradually propagate toward the output IDT. FIGS. 31A-31C show the transit simulations as related to time with FIG. 31A at T=3.1 $e^{-8}$ s, FIG. 31B at T=3.5$e^{-8}$ s, and FIG. 31C at T=3.9$e^{-8}$ s. The displacements of acoustic waves are shown in different colors to represent the different magnitudes as illustrated in the key. They propagate along the propagation axis toward the output IDT. FIG. 32 shows the maximum displacements that increase gradually on the surface as time moves from 0 to 40 ns.

TABLE 3

| Number | Step name | Action | Material Name | Thickness (um) | Photoresist |
|---|---|---|---|---|---|
| 0 | Substrate | Substrate | 128° YX | 50 | |
| 1 | Planar Fill | Planar Fill | Al | 0.2 | |
| 2 | Straight Cut | Straight Cut | | | + |

Harmonic simulations of single-track and dual-track SAW resonators are shown in FIGS. 33A and 33B, which illustrate a 3D model for the single-track SAW resonator and the parallel track SAW resonator, respectively. The width of electrodes in both resonators was 8 μm and the number of finger pairs in the input and output IDTs is 10. Both SAW resonators were meshed by Manhattan brick elements. Input signals ($V_s$=5V) with different frequencies were applied at the input IDTs in the harmonic simulations. 3D models of SAW resonators were established based on the previous requirements and are shown in FIGS. 33A and 33B. The acoustic waves are traveling from the input IDT to the output IDT. Maximum displacements occur when the frequency of input signals is equal to the frequency of acoustic waves. Displacements on the surface are translated into electrical signals in the receiving IDT. FIG. 34 shows the displacements in the frequency, which ranges from 100 MHz to 150 MHz. The maximum displacement occurs in the center frequency $f_o$, which is the frequency of the acoustic waves. According to simulation results, the center frequency is 127.27 MHz with a 0.026 μm displacement in the Z direction. Another simulation, shown in FIG. 35, is the maximum displacement with different numbers of finger pairs in the input and output IDTs. The magnitude of displacement can be increased gradually by adjusting the number of finger pairs in the input and output IDTs.

C. Fabrication and Measurement of One-Pole Synchronous SAW Resonators

SAW resonators having frequencies of approximately 121 MHz and 978 MHz were fabricated on the 128° YX LiNbO$_3$ wafers. The structures of SAW resonators fabricated included both single-track and dual-track (or parallel) IDTs with gratings 118, 120 having shorted reflectors according to at least one embodiment discussed in Section A. The feature size of 121 MHz and 978 MHz SAW resonators are 8 μm and 1 μm, respectively. These SAW resonators cannot be fabricated by using standard CMOS processes due to the piezoelectric substrates, and thus the microfabrication was carried out in a clean room to fabricate the SAW resonator. The microfabrication process includes depositing, patterning and etching on the surface of substrates. The metal thin film was deposited and defined by the patterning process. The detailed processes are illustrated and discussed below. U.S. Pat. Pub. No. 2008/0230859 to Zaghloul et al. provides a description of how to fabricate SAW resonators on CMOS. This application publication is hereby incorporated by reference.

After the resonators were fabricated, the measurements were performed directly on the wafer. The Vector Network Analyzer (Model No. 8722D) was used to measure the frequency response at the output and was connected to the SAW resonator by the probe station. The probe station has ground-signal-ground (GSG) probe tips, which contacted the metal pads on the wafer directly. The input and output of the resonators were connected to probe pads by metal traces. The measurement setup is depicted in FIG. 36 (where DUT is representative of the SAW resonator being tested) and discussed in the following section. The frequency responses of single-track and dual-track IDTs with shorted reflectors were measured and compared with the single-track IDT without shorted reflectors.

The major process to define the SAW resonators on the 128° YX LiNbO$_3$ wafers is photolithography or optical lithography. This process transfers the pattern from the photomask to light-sensitive photo resist by UV light. The pattern on the photoresist can be removed to expose the material underneath it. Two different etching processes, wet etching and dry etching, were used in fabrication. The wet etching process is easy to perform but has the disadvantage of side-wall-etching. Dry etching can remove the upper layer of the substrate in areas not covered by photoresist and is generally used to avoid undercutting beneath the photo resist pattern. The processes are depicted in FIG. 37.

Before photolithography was done, the masks were prepared according to the layouts. The layout of the SAW resonators was designed using the Cadence Design System and converting the layouts to Graphic Database System (GDS) files. The structures in the layout were covered by chrome on the quartz or soda-lime substrate. The layout of SAW resonators and 5" soda-lime mask are shown in FIGS. 38-39B. After the mask was prepared, an Aluminum thin film was deposited on the surface of the LiNbO$_3$ wafers and defined as interdigital transducers (IDT) structure. These IDTs in at least one embodiment are light so that they do not dampen the surface acoustic wave. For example, Aluminum has a lower density than gold and is suitable metal for IDT structures. The thickness of the IDTs is usually between 500 Å to 2000 Å; however, the thicker IDTs have lower resistance. Thus, the 2000 Å aluminum thin-film was used in the fabricated embodiments.

The LiNbO$_3$ wafers are very sensitive to changes in temperature. The wafer has a static charge on the surface and attaches to the metal surface when the temperature increases to over 100° F. Temperature differences can cause deformation and electrical charges on the wafers. Therefore, it becomes a critical issue to heat the wafer in the deposition process. A Denton E-beam evaporator is a tool used to deposit an Aluminum thin film consistently over the LiNbO$_3$ at room temperature. After the LiNbO$_3$ wafers were coated with a 2000 Å Aluminum thin film, the IDT structures were defined using the mask aligner. The mask aligner allowed UV light to shine through the photomask to expose the photoresist. The area covered by the chrome on the mask blocked the UV light and protected the photoresist from exposure. Patterns covered by chrome on the mask were translated onto the photoresist layer. FIG. 37 shows the Denton E-beam evaporator and two different kinds of mask aligners. A MJB-3 Mask Aligner is used for the 4-inch mask and 3-inch wafer. The resolution of the MJB-3 Mask Aligner is about 3 μm in contact mode, which yields a minimum distance of 3 μm. An Oriel Mask Aligner has a higher resolution, which can yield a feature size down to 1 μm. FIGS. 39A and 39B show a STS dry etching system for a 4-inch wafer. In order to define 1 μm electrodes, the STS Etcher was used to avoid undercutting the photoresist pattern.

FIG. 40A-40C shows the structure for 121 MHz SAW resonators where the electrodes are about 8 μm wide and etched using a wet etching process. The error in electrodes due to the wet etching process can be tolerated, because the width of the electrodes is much wider than the error of the electrodes. This small difference in the width of the electrodes; however, will be relatively important if the width of the electrodes is 1 μm. To resolve this error, an ICP system was used to identify the electrodes producing vertical sidewall and avoiding the error in the electrodes' width.

The recipes and equipments of microprocesses used for fabrication are shown in Table 4. These recipes are not the same as standard CMOS processes. They were verified several times to define the best structure on the $LiNbO_3$ substrate; however, the $LiNbO_3$ substrate is highly sensitive to the temperature. Temperature effects are shown in Table 5. It is necessary to be careful during any processes involving heating or cooling.

TABLE 4

| Processes | Equipments | Recipes |
| --- | --- | --- |
| Wet Etch | Etch Tunnel Acid/ Solvent Bench | Heated Aluminum Etch: Phosphoric Acid/50°/2 mins |
| Soft bake (AZ1813 Resist) | Baker | 90°/1 mins |
| E-Beam Evaporator (Aluminum Evaporation) | Denton E-beam/ Thermal Evaporator | 6.5 KV/2E–6 torr/5-20 mins (depend on the current) |
| Dry Etch | Inductive Coupled Plasma (ICP) | Standard AlGaAs Recipe ($SiCl_4$ and Ar at 1.5 mT and |
| UV light Exposure | EVG Mask Aligner | 5 inch × 5 inch Masks plate/4 inch Window |
| Remove the Resist | March Jupiter III O2 plasma system | >8 hrs |

TABLE 5

| Processes | Temperature | Effects |
| --- | --- | --- |
| Heating Rate | 5° C./minute | The electrostatics happens on the surface. The wafer might be shattered when temperature jumps too much. |
| Soft Bake | T ≤ 90° C | A good alternative baking processes is to bake in a convection oven for 20 minutes. |
| Hard Bake | T ≤ 120° C. | The wafer breaks into pieces when the temperature is over 120° C. |
| Cooling | | The wafer adheres to the metal. The wafer might be shattered due to thermal expansion. |

FIG. 40A shows the whole structures of the 121 MHz single-track SAW resonator on the 128° YX $LiNbO_3$ wafer, which has input/output IDTs and reflectors. Input/output IDTs are connected to the traces with metal pads on the end. Measurements can be made by using probes to connect these pads directly on the wafers. The thickness of these electrodes is 2000 Å and the structure of fingers is shown in FIGS. 40B and 40C. Reflectors in the built SAW resonators are half a wavelength away from the IDT. The wavelength λ is the distance between the two continuous electrodes as depicted in FIG. 40C and is equal to 8 μm, which yields a center frequency $f_o$ of up to 121 MHz. The distance between electrodes is slightly larger than the width of the electrode. The electrodes in FIG. 40C are slightly over etched by the wet etch process. FIG. 10 shows the 121 MHz SAW resonator diced from the wafer and connected to the SAW connectors.

Before doing a $S_{21}$ measurement of the frequency response of the 121 MHz and 978 MHz resonators, the network analyzer was calibrated to eliminate the mismatch between the network analyzer and the chip. In order to increase measurement accuracy, the full two-port calibration had to be performed before the measurements by using a 3.5 mm broadband calibration tool kit. By using the full two-port calibration, including short, open, load and through between input and output, mismatch and noise from the cables can be avoided. The calibration also helps to define the Smith chart and increase the accuracy of frequency responses. A Micro-Tech Probe station was used to perform the measurement directly on the wafer. The size of the contact pads on the RF Microwave Probe was about 70 μm by 70 μm and the separation between pads was about 100 μm. The probe station was connected to the network analyzer by SMA cables. The calibration for the probe station and network analyzer had to be performed before the measurement by using Impedance Standard Substrates (ISS).

The measurement arrangement is depicted in FIG. 36. The through circuit was used to calibrate the parasitic effects in the transmission line. It was fabricated on the wafer with SAW resonators. As shown in FIG. 41, the through circuit is designed next to the resonator in Cadence. The ground-signal-ground (GSG) probe pads for input and output probes are connected together. The distance between input and output pads is the same as the distance in the resonator.

$S_{11}$ and $S_{22}$ are input and output reflection coefficients, and $S_{12}$ and $S_{21}$ are reverse and forward coefficients. The conversions from Y-parameters to S-parameters are shown in Equations 22-25. $S_{21}$ represent the ratio of power received at the load to available power from the input source, and is also the insertion loss discussed previously.

$$S_{11} = \frac{(1 - y_{11}Z_0)(1 + y_{22}Z_0) + y_{12}y_{21}Z_0^2}{(1 + y_{11}Z_0)(1 + y_{22}Z_0) - y_{12}y_{21}Z_0^2}$$ Equation 22

$$S_{12} = \frac{-2y_{12}Z_0}{(1 + y_{11}Z_0)(1 + y_{22}Z_0) - y_{12}y_{21}Z_0^2}$$ Equation 23

$$S_{21} = \frac{-2y_{21}Z_0}{(1 + y_{11}Z_0)(1 + y_{22}Z_0) - y_{12}y_{21}Z_0^2}$$ Equation 24

$$S_{22} = \frac{(1 + y_{11}Z_0)(1 - y_{22}Z_0) + y_{12}y_{21}Z_0^2}{(1 + y_{11}Z_0)(1 + y_{22}Z_0) - y_{12}y_{21}Z_0^2}$$ Equation 25

The measurement setup included a probe station, a network analyzer and 50 ohm cables. The $LiNbO_3$ wafer was placed in the center of the probe station and observed through the microscope. SAW filters on the $LiNbO_3$ wafer were connected to the network analyzer by using probe tips. After the probe tips were connected to metal pads, the calibration (open, short, 50 ohm and through) had to be performed to eliminate the mismatch. As mentioned previously, through circuits were designed and fabricated next to the SAW structures on the wafer.

FIGS. 42 and 43 show the frequency response of dual-track and single-track IDTs having the center frequencies are 121 MHz (FIG. 42) and 978 MHz (FIG. 43), respectively. In the absence of reflectors, the single-track IDT has a wide band and two pole $S_{21}$ response as shown in FIGS. 42 and 43. With the shorted reflectors included, there is an additional resonance superimposed on the center frequency. This additional resonance has 90° phase shifts in the center frequency and a deep notch as discussed previously. The SAW resonators with shorted reflectors have a one-pole response with a higher insertion loss and Q factor when compared to the frequency response of the single-track IDT without shorted reflectors. The out-of-band rejection is improved slightly by connecting two single-track IDTs in parallel to form parallel IDTs (see, e.g., FIG. 6). The dual-track IDT also has a better insertion loss and Q factor in comparison with the single-track IDT. The insertion loss of the dual-track IDT with shorted reflectors is −3.1 dB in the 121 MHz center frequency and the Q factor is 192.42. The insertion loss of the dual-track IDT with shorted reflectors in 978 MHz is −2.8 dB and the Q factor is 412.59.

D. Testing of One-Pole Synchronous SAW Resonators as Mass Sensors

This section will provided an explanation regarding the development and testing of the low-loss single-pole SAW resonator for sensing applications. As discussed previously, the 128° YX LiNbO$_3$ has the advantages of a high K$^2$ (5.3%) and velocity-shift coefficient $k_{11m}$, which is the coefficient of velocity shift due to the mass-loading effect on the electrode. The higher $k_{11m}$ yields larger frequency shifts and mass sensitivities, which is easier to observe in the output signal from the output IDT. The high K$^2$ material, like 128° YX LiNbO$_3$, can also yield a higher insertion loss in comparison with the same SAW structure on other piezoelectric materials. The disadvantage of the standard SAW resonator on 128° LiNbO$_3$ substrate is wide band response as shown in FIGS. 42 and 43.

The bidirectional IDTs without reflectors not only have a low Q factor, but also a two-pole resonance as shown in FIGS. 42 and 43. This two-pole resonance with the low insertion loss implies the difficulties in determining the center frequency and frequency shift. The improvement of the Q factor and one-pole response can make it easier to observe the frequency shift and increase the sensitivity for mass sensor applications. To achieve this one-pole frequency response, the SAW resonator was designed based on the distance parameters and shorted reflectors as illustrated in FIGS. 5 and 6. The reflecting acoustic waves in the output IDT result in an additional one-pole superimposed resonance as shown in FIGS. 42 and 43. It is easier to find its center frequency and frequency shift from this one-pole frequency response which has a maximum insertion loss in the center frequency.

The one-pole synchronous SAW resonators in at least one embodiment have the following advantages for a sensing application: a one-pole S$_{21}$ response with the maximum insertion loss in the center frequency to read the signal, a high insertion loss so that it does not need amplifiers or attenuators, and a smaller size than delay line SAW sensors, because there is no quadrate sensing area between the input and output IDTs. These advantages are also largely beneficial to filtering applications.

For this section, the dual-track IDT SAW resonator was used as a mass sensor. The frequency shift and sensitivity can be determined by its one-pole resonance where it has the maximum insertion loss. This resonator also has a low loss response and high mass sensitivity (1.315×10$^{11}$ Hz·mm$^2$/g) in comparison with a delay-line SAW mass sensor (1.24×10$^9$ Hz·mm$^2$/g).

The structures of the one-pole synchronous SAW resonators are shown in FIGS. 5 and 6, while FIG. 15 illustrates the sensing area extending over the input IDT 114, the output IDT 116, and the gratings 118, 120. There were two types of structures examined: the single-track and dual-track IDT with synchronous reflectors. These two structures were examined and compared in the frequency response. As discussed above, the out-of-band rejection and shape factor can be improved by the dual-track IDT structure. The maximum insertion loss in the main lobe of resonance can have more side lobe rejection as shown in FIGS. 42 and 43. FIGS. 5 and 6 also show that the output IDT is placed at the minimum distance ($d_g$=λ/2) next to the input IDT. This optimal minimum distance can avoid the propagating loss in the acoustic transmission line between IDTs. The reflectors are also placed symmetrically next to the input and output IDTs. The acoustic wave pattern in FIGS. 5 and 6 show that the strips of reflectors are placed in the optimal positions outwards from the minimum close-in position ($d_r$=λ/2). The gratings 118, 120 can have the maximum reflectivity when the strips are placed synchronously on the acoustic wave pattern. Furthermore, the strips in the gratings 118, 120 are connected together as "shorted reflectors." These shorted reflectors can have a larger reflection coefficient than the unshorted reflectors. The reflection coefficient is nearly 100% when there are more than 15 electrodes in the reflectors.

The configuration for taking the measurements is depicted in FIG. 44. The mass sensors are connected to a network analyzer to examine the frequency shifts. The mass is dropped on the sensing area which covers the input/output IDTs and reflectors. This additional mass affects the velocity and center frequency of acoustic waves. In order to examine the frequency shifts of mass sensors, a chemical compound potassium chloride (KCL) was deposited on the surface. The purpose of the experiment was to place small mass on the surface of SAW mass sensors. For this purpose, the KCL solution was chosen. The detail steps of the measurement are discussed later. 4 µl KCL solutions were dropped onto the sensing area using a pipette. After the solvent evaporates, the KCL remains on the surface with a uniform thin film. This KCL thin film has a small mass on the electrodes and causes the center frequency to shift. In this work, different concentrations (from 3×10$^{-5}$ M to 3×10$^{-3}$ M) of KCL solutions were used to measure the mass sensitivity of mass sensors. According to the results, the one-pole synchronous SAW mass sensor has a high sensitivity and good linearity (1.32 e$^{11}$ Hz·mm$^2$/g).

The acoustic waves are excited by electrical signals in the input IDT; however, the mass of the electrodes in the IDTs dampen these acoustic waves. The mass impacts the velocity and amplitude of acoustic waves. The SAW velocity on the free space can be reduced when it is under the IDT. This reduction also decreases the radiation conductance $G_a(f)$ and center frequency $f_o$. Both are important factors for determining the insertion loss in the output IDT.

According to the material properties of 128° YX LiNbO$_3$, the fractional velocity decrease $$\frac{\Delta v}{v}$$

can be expressed as Equation 26 in terms of the film-thickness ratio $$\frac{h_1}{\lambda_1}$$

where h is the thickness of the electrodes and λ is the acoustic wavelength. $k_{11p}$, $k_{11m}$, and $k_{11s}$ are velocity-shift coefficients, which are three important factors of velocity shifts. This first term $$\left[\frac{\Delta v}{v}\right]_p$$

is the velocity shift due to the shorting piezoelectric fields in the metalized regions. For this discussion, the metallization is equal to 50% so that the metalized region is equal to $$\frac{\lambda}{4}.$$

The second term $$\left[\frac{\Delta v}{v}\right]_m$$

is the velocity shift due to the loading mass on the metalized region. It can be expressed as $k_{11m}$ and the film-thickness ratio. When the aluminum electrodes are deposited, the mass of electrodes decreases the acoustic velocity and center frequency. When the KCL is deposited, the center frequency decreases further. The third term $$\left[\frac{\Delta v}{v}\right]_s$$

is related to the effective stiffness of the propagating surface when the metal electrodes are deposited on the piezoelectric substrate. The total velocity shifts are calculated from these three terms which can be expressed in term of three important parameters $k_{11p}$, $k_{11m}$, and $k_{11s}$. The differential equation of acoustic velocity in Equation 26 is expressed in terms of the exponential function of film-thickness ratio. If the film-thickness ratio is less than 1%, the exponential function of film-thickness ratio is approximate to film-thickness ratio as shown in Equation 27. The frequency changes can be further derived in Equation 28. If there is additional mass deposited on the electrodes, the frequency shifts further as shown in Equation 29. However, the frequency shift does not have a linear relation to the additional mass $\Delta m$ on the electrodes. It can be linear only when the third term of $k_1$ is zero. According to the properties in Table 6, 128° YX LiNbO$_3$ has a zero $k_{11s}$ and high $k_{11m}$. It implies a linear equation with the large frequency shift when additional mass is on the electrodes. Based on these properties, Equation 30 shows the linear relation between the frequency shift and additional mass on 128° YX LiNbO$_3$ substrate.

If there is additional mass deposited uniformly on the electrodes, then this additional mass causes additional shifts in the velocity and center frequency. Equation 31 shows the frequency shift due to the additional mass on the electrodes. $\Delta m$ and $A_s$ are the total additional mass on the sensing area. If the KCL is used to examine the frequency shift, the additional mass $\Delta m$ can be translated into the concentration and volume of the KCL solution (MW$_{KCL}$×M×$\Delta V$). The sensitivity of mass sensors can be expressed as the frequency shifts divided by the mass density $$\rho\left(\rho = \frac{\Delta m}{A_s}\right).$$

The velocity perturbation is $$\left[\frac{\Delta v}{v}\right] = \left[\frac{\Delta v}{v}\right]_p + \left[\frac{\Delta v}{v}\right]_m \times \left(0.0158 \times \left(1 - e^{\frac{h/\lambda}{0.01}}\right)\right) + \left[\frac{\Delta v}{v}\right]_s \times \left(0.0158 \times \left(1 - e^{\frac{h/\lambda}{0.01}}\right)\right)^2 =$$

$$k_{11p} + k_{11m} \times \left(0.0158 \times \left(1 - e^{\frac{h/\lambda}{0.01}}\right)\right) + k_{11s} \times \left(0.0158 \times \left(1 - e^{\frac{h/\lambda}{0.01}}\right)\right)^2 \quad \text{Equation 26}$$

if $\frac{h}{\lambda} \ll 0.01$, then $$\left[\frac{\Delta v}{v}\right] = k_{11p} + k_{11m} \times \left(0.0158 \times \left(1 - e^{\frac{h/\lambda}{0.01}}\right)\right) + \quad \text{Equation 27}$$

$$k_{11s} \times \left(0.0158\left(1 - e^{\frac{h/\lambda}{0.01}}\right)\right)^2 \approx$$

$$\left[\frac{\Delta v}{v}\right]_p + \left[\frac{\Delta v}{v}\right]_m \times \left(\frac{h}{\lambda}\right) + \left[\frac{\Delta v}{v}\right]_s \times \left(\frac{h}{\lambda}\right)^2 \approx$$

$$k_{11p} + k_{11m} \times \left(\frac{h}{\lambda}\right) + k_{11s} \times \left(\frac{h}{\lambda}\right)^2$$

$$\Delta f = \frac{v}{\lambda} \times \left[k_{11p} + k_{11m} \times \left(\frac{h}{\lambda}\right) + k_{11s} \times \left(\frac{h}{\lambda}\right)^2\right] \quad \text{Equation 28}$$

The frequency shift due to electrodes and the additional mass is $$\Delta f = \frac{v}{\lambda} \times \left[k_{11p} + k_{11m} \times \left(\frac{h + h_{KCL}}{\lambda}\right) + k_{11s} \times \left(\frac{h + h_{KCL}}{\lambda}\right)^2\right] \quad \text{Equation 29}$$

$$= \frac{v}{\lambda} \times \left[\begin{array}{l} k_{11p} + k_{11m} \times \\ \left(\left(\frac{h}{\lambda} + \frac{h_{KCL} \times A_S}{\lambda \times A_S}\right) + k_{11s} \times \left(\frac{h}{\lambda} + \frac{h_{KCL} \times A_S}{\lambda \times A_S}\right)^2\right) \end{array}\right]$$

$$= \frac{v}{\lambda} \times \left[\begin{array}{l} k_{11p} + k_{11m} \times \\ \left(\left(\frac{h}{\lambda} + \frac{\Delta v}{\lambda \times A_S}\right) + k_{11s} \times \left(\frac{h}{\lambda} + \frac{\Delta v}{\lambda \times A_S}\right)^2\right) \end{array}\right]$$

$$= \frac{v}{\lambda} \times \left[\begin{array}{l} k_{11p} + k_{11m} \times \left(\frac{h}{\lambda} + \frac{\Delta m}{\lambda \times A_S \times D_{Al}}\right) + \\ k_{11s} \times \left(\frac{h}{\lambda} + \frac{\Delta m}{\lambda \times A_S \times D_{Al}}\right)^2 \end{array}\right]$$

$$= \frac{v}{\lambda} \times \left[\begin{array}{l} k_{11p} + k_{11m} \times \left(\left(\frac{h}{\lambda}\right) + \frac{1}{\lambda D_{Al}} \times \frac{\Delta m}{A_S}\right) + \\ k_{11s} \times \left(\left(\frac{h}{\lambda}\right) + \frac{1}{\lambda D_{Al}} \times \frac{\Delta m}{A_S}\right)^2 \end{array}\right]$$

For 128° YX LiNbO$_3$, $k_{11p}$=0.022, $k_{11m}$=0.091, $k_{11s}$=0 with reference to Table 6.

$$\Delta f = \frac{v}{\lambda} \times \left[k_{11p} + k_{11m} \times \left(\left(\frac{h}{\lambda}\right) + \frac{1}{\lambda D_{Al}} \times \frac{\Delta m}{A_S}\right)\right]$$

$$= \frac{v}{\lambda} \times k_{11p} + \frac{v}{\lambda} \times k_{11m} \times \left(\frac{h}{\lambda}\right) + \frac{v}{\lambda} \times k_{11m}\left(\frac{1}{\lambda D_{Al}} \times \frac{\Delta m}{A_S}\right)$$

$$= \text{constant} + \text{constant} + \frac{v}{\lambda} \times k_{11m}\left(\frac{1}{\lambda D_{Al}} \times \frac{\Delta m}{A_S}\right)$$

The frequency shift due to additional mass becomes $$\Delta f = \frac{v}{\lambda} \times \frac{k_{11m}}{\lambda D_{Al}} \times \frac{\Delta m}{A_S} \qquad \text{Equation 30}$$

The frequency shift due to additional KCL film is $$\Delta f = \frac{v}{\lambda} \times \frac{k_{11m}}{\lambda D_{Al}} \times \frac{MW_{KCL} \times M \times \Delta V}{A_S} \qquad \text{Equation 31}$$

The mass sensitivity is $$S_m^f = \frac{\Delta f}{\rho} = \frac{v}{\lambda} \times \frac{k_{11m}}{\lambda D_{Al}} \qquad \text{Equation 32}$$

where v is the velocity of acoustic waves on the free space, $\lambda$ is the wavelength of acoustic waves, h is the thickness of electrodes, $\Delta v$ is the velocity shift, $\Delta f$ is the frequency shift, $k_{11p}$ is the velocity-shift coefficient due to shorted metalized region, $k_{11m}$ is the velocity-shift coefficient due to the mass, $k_{11s}$ is the velocity-shift coefficient due to stiffness, $D_{Al}$ is the density of the Aluminum electrodes (although the density of the material used for the electrode could be substituted if different than Aluminum), $\Delta m$ is the mass of the electrodes, $A_S$ is the sensing area, $MW_{KCL}$ is the molecular weight of KCL, M is the concentration of KCL solution, $\Delta V$ is the volume of KCL solution, $S_m^f$ is the mass sensitivity, and $\rho$ is the mass density.

Based on Equation 26 and Equation 30, the frequency shifts were simulated in FIGS. 45A and 45B by using MATLAB. According to previous theoretical equations, the frequency shifts are approximately linear curves if the film-thickness ratio is less than 0.01. This ratio can also imply the linear region of frequency shifts and maximum detectable mass in this theoretical model. As shown in FIGS. 45A and 45B, the maximum detectable mass densities are $10.8 \times 10^{-8}$ g/mm² and $86.4 \times 10^{-8}$ g/mm², for 978 MHz SAW mass sensors (FIG. 45B) and 122 MHz SAW mass sensors (FIG. 45A), respectively.

Table 6 shows the parameters of common piezoelectric materials, including their velocity-shift coefficients. 128°YX LiNbO₃ is the piezoelectric material with the highest velocity v and electromechanical coupling K². 128°YX LiNbO₃ also has a high $k_{11n}$ so that it is highly sensitive in detecting the mass put on it. Its properties of zero $k_{11s}$ and high $k_{11n}$ can yield a linear relation between the mass and frequency shifts, which are important for sensing applications. The fabricated IDT structures from above were used to achieve the one-pole low-loss SAW resonators for sensing applications. The characteristic of one-pole and low loss can make it easier to observe the center frequency in the output IDT. Based on Equation 31, the theoretical calculation of mass sensitivities in 121 MHz and 978 MHz are shown in Table 7.

TABLE 6

| | Substrate | | | | |
|---|---|---|---|---|---|
| | ST-X Quartz | YX LiNbO₃ | 128° YX LiNbO₃ | 64° YX LiNbO₃ | 36° YX LiTaO₃ |
| SAW velocity $v_o$ (m/s) | 3158 | 3488 | 3997 | 4742 | 4212 |
| Axis | X | Z | X | X | X |
| Electromechanical coupling coefficient K² | 0.0016 | 0.045 | 0.056 | 0.113 | 0.047 |
| $C_o$ Capacitance/finger pair/unit length | 0.503 | 4.5 | 5.0 | | |
| $k'_{11p}$ | 0.0004 | 0.018 | 0.022 | 0.052 | 0.0076 |
| $k'_{11m}$ | 0.02 (h/λ) | 0.3 (h/λ) | 0.091 (h/λ) | 0.18 (h/λ) | 0.0011 (h/λ) |
| $k'_{11s}$ | 7.9 (h/λ)² | | | 1.4 (h/λ)² | 3.6 (h/λ)² |
| TCD (ppm/° C.) | ≈0 | 94 | 75 | 70 | 35 |
| $k'_{12p}$ | 0.0001 | 0.0054 | 0.0064 | 0.0091 | 0.0069 |
| $k'_{12m}$ | 0.16 | 0.08 (h/λ) | 0.14 (h/λ) | 0.48 (h/λ) | 0.12 (h/λ) |
| $k'_{12s}$ | | | | | 2.8 (h/λ)² |
| Wave Type | Rayleigh wave | Rayleigh wave | Rayleigh wave | Leaky SAW | Leaky SAW |

Table 6 lists the parameters of piezoelectric substrates based on the 50% Aluminum metallization and shorted reflectors. h is the thickness of electrodes and $\lambda$ is the wavelength of acoustic waves.

TABLE 7

| v (m/s) | λ(m) | k11m | DAl (g/m³) | $S_m^f$ (Hz · mm²/g) |
|---|---|---|---|---|
| 3997 | 3.20e⁻⁵ | 0.091 | 2.7e⁶ | 1.32e¹¹ |
| 3997 | 4.00e⁻⁶ | 0.091 | 2.7e⁶ | 8.42e¹² |

Table 7 lists the theoretical calculation of mass sensitivities ($S_m^f$) of 121 MHz and 978 MHz SAW mass sensors.

The mass sensors depicted in FIGS. 5 and 6 were simulated using Coventorware. The KCL film was deposited on the sensing area which includes the input/output IDTs and reflectors as depicted in FIG. 46. A 3D model of the mass sensors is shown in FIG. 47 with the top layer being the KCL film. In the Coventorware simulation, the acoustic waves propagate between the KCL film and substrates, but the waves are impacted by the mass of KCL films. The presence of the KCL film causes the center frequency of the acoustic waves to decrease. In FIG. 48, the frequency shifts are simulated in connection with the thickness of KCL films. The mass of KCL films is in direct proportion to the thickness of KCL films. According to the simulation results, the frequency shift increases linearly when the thickness increases.

The configuration for taking measurements is depicted in FIG. 44. The KCL solutions, in different concentration, were dropped in the sensing area using a pipette. The $LiNbO_3$ is sensitive to temperature variance and a 1° C. temperature difference can make a 9 KHz frequency shift, so it was important to keep the temperature stable during the measurement. All measurements in this work were done at room temperature and operated in an isolated chamber having a heating place below the SAW mass sensor and a fan to cool the chamber as needed (see, e.g., FIG. 13). The temperature in the chamber was monitored using an infrared thermometer. Because there were no heating or cooling processes during depositions of KCL films, the temperature variance was less than 0.1° F. (the minimum scale of the infrared thermometer used during testing). The original center frequency $f_o$ before depositing KCL films was examined again after washing off the previously deposited KCL film. The steps used in the measurement of the KCL films were as follows: (1) the SAW resonator was connected to the network analyzer to measure the center frequency; (2) the 4 μl KCL solution was dropped onto the sensing area and left on the surface for 15 minutes; (3) the frequency shift due to the deposited KCL film on the electrodes was measured; (4) the KCL film on the surface was washed off and the center frequency was measured again. This last step was done to verify the original center frequency in the first step. If there were influences from temperature changes, the original center frequency could not be measured in step (4). Based on these measurement steps, FIG. 49 and Table 8 were developed to show the different frequency responses when different masses of KCL films were deposited on the surface of the 121 MHz SAW mass sensor. The mass of the KCL film not only decreased the velocity, but also the amplitude of the acoustic waves. When the $2.43e^{-6}$ $g/mm^2$ KCL film is deposited, the center frequency $f_o$ and insertion loss decrease in comparison with the frequency response without the KCL film. This decrease is the frequency shift $\Delta f$ due to the KCL film.

TABLE 9

| Concentration (M) | Mass density (g/mm$^2$) | Frequency shifts |
|---|---|---|
| 0.0047 | $1.52e^{-7}$ | 0.02 |
| 0.0094 | $3.04e^{-7}$ | 0.04 |
| 0.0188 | $6.08e^{-7}$ | 0.08 |
| 0.0375 | $1.22e^{-7}$ | 0.15 |
| 0.075 | $2.43e^{-7}$ | 0.245 |
| 0.15 | $4.86e^{-7}$ | 0.305 |
| 0.3 | $9.73e^{-7}$ | 0.305 |

The curves of mass sensitivity in FIG. 50 were obtained by measuring frequency shifts from low concentration to high concentration. As illustrated in FIG. 50, the frequency shifts versus the mass densities of the KCL films for the mass sensors operating at 121 MHz and 978 MHz. The minimum detectable mass of sensors in 121 MHz is 152.1 ng/mm$^2$ with a 0.02 MHz frequency shift which yields a mass sensitivity of up to $1.315e^{11}$ Hz·mm$^2$/g. The minimum detectable mass of sensors in 978 MHz is 24.3 ng/mm$^2$ with a 0.2 MHz frequency shift which yields the mass sensitivity to $8.23e^{12}$ Hz·mm$^2$/g. The mass sensitivity is the ratio of the frequency shift $\Delta f$ and mass density ρ, which is an important parameter in evaluating mass sensors. In the Coventorware simulation, the theoretical mass sensitivities of 121 MHz and 978 MHz mass sensors in Table 7 are $1.32e^{11}$ Hz·mm$^2$/g and $8.42e^{12}$ Hz·mm$^2$/g, respectively. In Equation 31 of the mass sensitivity, the frequency shift $\Delta f$ is inversely proportional to the wavelength λ. The sensor in 978 MHz has a smaller wavelength than the sensor in 121 MHz resulting in it having a sharper slope for the linear region in FIG. 50.

FIG. 51 depicts a configuration of the SAW mass sensor 110' with a 3.4 mm plastic well 132 disposed above it. This plastic well 132 gives a fixed sensing area for the KCL deposition. The SAW resonator 110' in at least one embodiment is in the center of the chip and connected directly to SMA connectors 820. In at least one embodiment, the silver paste is put between the connectors and traces to increase the conductance. The sensing area is an important factor in the measurement, which is directly proportional to the mass sensitivity. If there is a 5% difference in the area, there will be a 5% change in the sensitivity. In order to measure the precise frequency shift, it is necessary to define the sensing area. In this experiment, the plastic well 132 was used to define the size of the KCL drops. The diameter of the plastic well 132 used in the testing was 3.4 mm (or 3/16″) which makes the sensing area $A_s$ equal to approximately 9.0746 mm$^2$. The KCL drop fills the area of the well. FIG. 52 shows a SEM picture of the KCL film and the smoothness and uniform surface of the film. The mass density of the film is 9.73 ng/mm$^2$ and its thickness is about 1000 Å. The roughness of the KCL films is less than 100 Å.

The SAW mass sensor used in the experiment has a high sensitivity and good linearity for sensing applications based on the experiments using the KCL films to examine the frequency shifts and mass sensitivities. The additional KCL films were directly deposited on the electrodes impacting the velocity of acoustic waves. Based on the previous experimental results, the minimum detectable mass for the 121 MHz SAW is 131.5 ng/mm$^2$. The signal shows a high sensitivity and low-loss response for sensing application. In order to use the SAW mass sensors for bio-sensing in a liquid environment, it is necessary to isolate the electrodes from the molecules on the surface. This isolation can prevent the molecules to short the electrodes. In view of the results with KCL films, a Polyvinyl Chloride (PVC) layer was used to cover the devices and isolate electrodes to test the effectiveness of using a polymer. Although the 121 MHz SAW mass sensor is covered by PVC, it still detected the small mass ($1.11 \times 10^{-7}$ g/mm$^2$) on the surface and operate in the liquid-phase environment. The 121 MHz polymer-coated SAW mass sensor, with mass sensitivity is $1.037e^{11}$ Hz·mm$^2$/g, can be used as biosensors and operate in the liquid-phase environment. FIG. 11 depicts the configuration and measurement of the polymer-coated SAW mass sensor 110'. The mass sensor 110' was placed in center of the microscope slide 832. This slide 832 was able to be placed into housing device 1110, which was designed for this mass sensor 110' and connected to the network analyzer. This housing device 1110 was made from PCB board. As the measurement in the previously discussed KCL experiment, the standard KCL solutions with concentration from $3 \times 10^{-5}$ M to $3 \times 10^{-3}$ M were deposited onto the sensing area (5.664 mm$^2$) to examine the frequency shifts and mass sensitivities.

PVC has a chemical chain which has repeated vinyl groups and a chloride in each group. In this embodiment, PVC was selected to synthesize the thin film and isolate the electrodes. In order to synthesize PVC thin film, it was necessary to use a proper solvent to dissolve the PVC powers. The candidate solvent must have a low viscosity, easy evaporation and high solubility of PVC. Tetrahydrofuran (THF) was selected as a solvent for the PVC powder. THF is water-miscible and low-viscosity organic liquid in the standard temperature and pressure. The PVC powder can be dissolved in THF easily and formed a thin film after THF solvent evaporates. The chemical formula $(CH_2)_4O$ of THF has a heterocyclic compound structure. It is a useful solvent because of the polar ether and wide liquid range. The PVC powder can be easily dissolved in the THF solvent. For this embodiment, 0.1 mg of PVC powder was dissolved in a 100 ml of THF solvent, which yields a PVC-THF concentration of 1 g/l. 20 ml of 1 g/l PVC-THF solution was dropped onto the sensing area having a radius of 2.38125 mm. The PVC-THF solution covered the whole SAW mass sensor. The PVC film was formed after THF evaporated. The THF solvent evaporated in about 2 minutes so that the PVC film was fabricated easily. The mass of the PVC film on the surface was $1.12e^{-9}$ g/mm² and the thickness was about 1000 Å as measured by a profilometer. FIG. 53 shows the PVC layer under microscope, which has a relative smooth and uniform surface.

Although the polymer can isolate the electrodes, the mass of polymer also causes an additional mass to be placed on the surface. Equation 33 shows the frequency shift in terms of the film-thickness ratio and velocity-shift coefficients ($k_{11p}$, $k_{11m}$, $k_{11s}$). When the PVC polymer is coated on the electrodes, the mass of the polymer impacts the amplitudes and velocity of acoustic waves as shown in Equation 34. The KCL films are also deposited on the top of the polymer to examine the mass sensitivities in this experiment. The total frequency shift from the additional PVC polymer layer and the KCL film is shown in Equation 34. The frequency shift is only varied by the mass of the KCL film. The concentration of the KCL film was from $3\times10^{-5}$M to $3\times10^{-3}$ M. There were 18 μl KCL solution dropped onto the sensing area in this experiment. Equation 35 shows the frequency shifts from the variable KCL films. It also shows the linear relation between the frequency shift and total mass on the electrodes, which is important for sensing applications. The mass sensitivity of the polymer-coated SAW mass sensor can be express as Equation 36 in terms of the mass density ρ.

The frequency shift due to the electrodes is $$\Delta f = \frac{v}{\lambda} \times \left[ k_{11p} + k_{11m} \times \left(\frac{h}{\lambda}\right) + k_{11s} \times \left(\frac{h}{\lambda}\right)^2 \right] \quad \text{Equation 33}$$

The frequency shift due to the electrodes, the polymer and the KCL is $$\Delta f = \frac{v}{\lambda} \times \left[ k_{11p} + k_{11m} \times \left( \frac{\left(\frac{h}{\lambda}\right) + \frac{1}{\lambda D_{Al}} \times }{\Delta m_{polymer} + \Delta m_{KCL}} \right) + k_{11s} \times \left(\frac{h}{\lambda}\right)^2 \right]$$

$$= \frac{v \times k_{11p}}{\lambda} + \frac{v}{\lambda} \times \frac{k_{11m}}{\lambda D_{Al}} \times \frac{\Delta m_{polymer}}{A_S} + \frac{v}{\lambda} \times \frac{k_{11m}}{\lambda D_{Al}} \times \frac{MW_{KCL} \times M \times \Delta v}{A_S} + \frac{v \times k_{11s}}{\lambda} \times \left(\frac{v}{\lambda}\right)^2$$

$$= \frac{v \times k_{11p}}{\lambda} + \frac{v}{\lambda} \times \frac{k_{11m}}{\lambda D_{Al}} \times \frac{\Delta m_{polymer}}{A_S} + \text{constant} + \frac{v \times k_{11s}}{\lambda} \times \left(\frac{v}{\lambda}\right)^2$$

Equation 34

If the mass of polymer layer $\Delta m_{polymer}$ is constant, the equation for the frequency shift due to additional KCL film is as follows:

$$\Delta f = \frac{v}{\lambda} \times \frac{k_{11m}}{\lambda D_{Al}} \times \frac{\Delta m}{A_S} = \frac{v}{\lambda} \times \frac{k_{11m}}{\lambda D_{Al}} \times \frac{MW_{KCL} \times M \times \Delta V}{A_S} \quad \text{Equation 35}$$

The mass sensitivity then becomes $$S_m^f = \frac{\Delta f}{\rho} = \frac{v}{\lambda} \times \frac{k_{11m}}{\lambda D_{Al}} \quad \text{Equation 36}$$

FIG. 11 depicts the polymer-coated SAW mass sensor 110' and housing device 1110. As shown in the figure, the SAW mass sensor 110' is fabricated and placed in the center of microscope slides 832. It is placed into the housing device 1110 and connected to the network analyzer by SMA connectors 832 and cables. The through circuit for calibration is also designed and placed next to the SAW mass sensor 110'. The calibrations are performed before measurement to eliminate the mismatch from cables and the housing device 1110. The plastic well 132, as shown in FIG. 11, is used to define the sensing area. The sensing area includes the input and output IDTs 114, 116, 124, 126 and gratings 118, 120, 128, 130.

The plastic wells 132, such as those made by the 3M fabric cubicle Grip, are able to adhere to the mass sensors. This plastic well 132 has a 3/16" diameter circle and the sensing area is 17.814 mm². After putting the plastic well 132 on the SAW resonator 110', 20 ml of 1 g/l PVC-THF solution is dropped into the well to deposit a PVC thin film 142. The PVC thin film 142 is formed after the THF evaporates. In order to examine the mass sensitivity, 18 μl of the KCL solution was used to deposit a KCL thin film over the PVC layer 142. As occurred previously, different concentrations of KCL solutions are deposited on the surface to examine the frequency shifts. The KCL film remains on the top of the PVC layer 142 after the water evaporates, which takes about 30 minutes.

FIG. 54 shows the mass sensitivities of the 121 MHz SAW mass sensor. The mass sensitivity of SAW mass sensors without PVC layers is $1.315e^{11}$ (Hz·mm²/g) and the minimum detectable mass is $1.52e^{-7}$ g. The theoretical sensitivity of the 121 MHz SAW sensor is $1.32e^{11}$ (Hz·mm²/g). According to FIG. 54, the experimental result matches the theoretical model and the error is 3.78%. The mass sensitivity of the polymer-coated SAW mass sensors is $1.037e^{11}$ (Hz·mm²/g) and the minimum detectable mass is $1.11e^{-7}$ g. The frequency shifts of polymer-coated SAW mass sensors are less than SAW mass sensors without polymer. Although the PVC layer causes a decrease in sensitivity and frequency shifts, an advantage is that it protects the SAW components when it is placed in a liquid environment.

The steps of polymer-coated SAW mass sensors for biomedical applications are illustrated in FIG. 55A-55C. The electrodes are covered by a polymer 140 to provide isolation from the liquid environment 154. The polymer 140 in at least one embodiment prevents the electrodes from being shorted. The plastic well 132 is used to define the sensing area and hold the samples. The acoustic waves propagate between the polymer layer 140 and $LiNbO_3$ substrate 112. The antibodies 146 are attached on the surface of the biochemical coating 144 that covers at least part of the polymer layer 140 and is used to catch antigens 156 or other material of interest. In FIG. 55B, it shows a complete antibody-antigen 146-156 reaction on the biochemical layer 144. Table 10 shows that the smaller feature size of SAW mass sensor 110' allows it to have higher frequency shifts when a 20 pg/mm² mass is present on the electrodes. Based on the above, it should be appreciated that a nano-scale SAW (λ=40) device will have a high sensitivity (0.11 fg/Hz) and be able to detect a small mass (20 pg/mm²).

TABLE 10

| Width of electrodes (nm) | Wavelength λ (nm) | Center frequency (GHz) | frequency shift Δf (KHz) | velocity shift Δv (m/s) |
|---|---|---|---|---|
| 10 | 40 | 99.925 | 171.424078 | 0.00598376 |
| 20 | 80 | 49.9625 | 42.8560195 | 0.00299188 |
| 30 | 120 | 33.30833333 | 19.04711978 | 0.001994587 |
| 40 | 160 | 24.98125 | 10.71400488 | 0.00149594 |
| 50 | 200 | 19.985 | 6.85696312 | 0.001196752 |
| 60 | 240 | 16.65416667 | 4.761779945 | 0.000997293 |
| 70 | 280 | 14.275 | 3.498450572 | 0.000854823 |
| 80 | 320 | 12.490625 | 2.678501219 | 0.00074797 |
| 90 | 360 | 11.10277778 | 2.116346642 | 0.000664862 |
| 100 | 400 | 9.9925 | 1.71424078 | 0.000598376 |
| 110 | 440 | 9.084090909 | 1.416727917 | 0.000543978 |
| 120 | 480 | 8.327083333 | 1.190444986 | 0.000498647 |
| 130 | 520 | 7.686538462 | 1.014343657 | 0.000460289 |

Table 10 lists the frequency shifts when 20 pg/mm² mass is on the electrodes. The smaller width of electrodes yields to the higher frequency shift and mass sensitivity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," "approximately," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

VI. INDUSTRIAL APPLICABILITY

Different embodiments of this invention have application to a variety of fields including filtering applications in, for example, wireless communications and mass sensing applications with at least one advantage being an extremely low insertion loss as compared to existing technology.

We claim:
1. A surface acoustic wave resonator comprising:
a substrate that is a 128° YX LiNbO₃ crystal;
an input interdigital transducer mounted to said substrate, said input interdigital transducer having a plurality of electrode pairs;
an output interdigital transducer spaced a distance L from said input interdigital transducer and mounted to said substrate, said output interdigital transducer having a plurality of electrode pairs;
a first grating spaced the distance L from said input interdigital transducer and mounted to said substrate;
a second grating spaced the distance L from said output interdigital transducer and mounted to said substrate; and
wherein said distance L equals

$$\frac{\lambda}{2}.$$

2. The surface acoustic wave resonator according to claim 1, wherein
said input interdigital transducer and said output interdigital transducer have an identical number of electrode pairs; and
said first and second gratings each include at least 15 shorted reflectors.
3. The surface acoustic wave resonator according to claim 2 having an insertion loss between 0 dB and −5 dB.
4. The surface acoustic wave resonator according to claim 1, further comprising:
a second input interdigital transducer mounted to said substrate, said second input interdigital transducer having a plurality of electrode pairs;
a second output interdigital transducer spaced a distance L from said second input interdigital transducer and mounted to said substrate, said second output interdigital transducer having a plurality of electrode pairs;
a third grating spaced the distance L from said second input interdigital transducer and mounted to said substrate;
a fourth grating spaced the distance L from said second output interdigital transducer and mounted to said substrate; and
wherein said input interdigital transducer, said output interdigital transducer, said first grating and said second grating are aligned along a first path of the acoustic waves generated by said input interdigital transducer, said second input interdigital transducer, said second output interdigital transducer, said third grating and said fourth grating are aligned along a second path of the acoustic waves generated by said second input interdigital transducer, and said first path and said second path are parallel to each other.

5. The surface acoustic wave resonator according to claim 4, wherein
said first input interdigital transducer, said first output interdigital transducer, said second input interdigital transducer, and said second output interdigital transducer each have an identical number of electrode pairs; and
said first, second, third, and fourth gratings each include at least 15 shorted reflectors.

6. The surface acoustic wave resonator according to claim 5 having an insertion loss between 0 dB and −4 dB.

7. The surface acoustic wave resonator according to claim 4, further comprising:
a polymer layer covering said first input interdigital transducer, said first output interdigital transducer, said second input interdigital transducer, said second output interdigital transducer, said first grating, said second grating, said third grating, and said fourth grating; and
a biochemical coating over at least a part of said polymer layer.

8. The surface acoustic wave resonator according to claim 7, wherein
said polymer layer includes polyvinyl chloride, and
said biochemical coating includes gold with a plurality of analytes attached to said gold.

9. A mass sensor comprising:
a support member,
a surface acoustic wave resonator comprising
a substrate that is a 128° YX LiNbO$_3$ crystal,
an input interdigital transducer mounted to said substrate to receive an input electrical signal and transmit a pair of corresponding acoustic waves within said substrate, said input interdigital transducer having a plurality of electrode pairs,
an output interdigital transducer spaced a distance L from said input interdigital transducer and mounted to said substrate to receive the acoustic waves generated by said input interdigital transducer and transmit an output electrical signal, said output interdigital transducer having a plurality of electrode pairs,
a first grating spaced the distance L from said input interdigital transducer and mounted to said substrate,
a second grating spaced the distance L from said output interdigital transducer and mounted to said substrate,
a polymer layer having a bottom surface attached to said input interdigital transducer, said output interdigital transducer, said first grating, and said second grating, and
a biochemical coating over at least a portion of a top surface of said polymer layer;
a first connector in electrical communication with said input interdigital transducer; and
a second connector in electrical communication with said output interdigital transducer; and
wherein said distance L equals $$\frac{\lambda}{2}.$$

10. The surface acoustic wave resonator according to claim 9, wherein
said polymer layer includes polyvinyl chloride, and
said biochemical coating includes an analyte capture binding surface.

11. The mass sensor according to claim 9, further comprising an enclosure having
a housing connected to said first connector and said second connector, and
a cover connected to said housing, and together said housing and said cover define a cavity in which said surface acoustic wave resonator resides; and
wherein said first connector and said second connector each include
a jack external to said housing,
a mounting member attached to said support member and extending towards a center of said enclosure from said jack;
said support member includes tracings electrically connecting each jack to the respective interdigital transducer; and
said surface acoustic wave resonator further includes a well disposed above at least said input interdigital transducer and said output interdigital transducer.

12. The mass sensor according to claim 11, wherein said well is disposed above at least one of said first grating and said second grating.

13. The mass sensor according to claim 9, further comprising a controller electrically connected to said first connector and said second connector, said controller is capable of transmitting the input electrical signal to said first connector and receiving the output electrical signal from said second connector with any difference in frequencies between the input electrical signal and the output electrical signals representing a presence of a mass.

14. The mass sensor according to claim 9, further comprising:
a chamber defining a space with a plurality of walls in which said support member and said surface acoustic wave resonator reside;
a heating member in thermal communication with said surface acoustic wave resonator;
a fan in communication with the space defined by said chamber;
a temperature sensor in said chamber; and
a controller electrically connected to said heating member and said fan.

15. The mass sensor according to claim 9, wherein said input interdigital transducer includes electrode pairs spaced such that the acoustic wave produced is between 100 MHz and 1 GHz.

16. The mass sensor according to claim 9, wherein said surface acoustic wave resonator further includes
a second input interdigital transducer mounted to said substrate to receive an input electrical signal and transmit a second pair of corresponding acoustic waves within said substrate, said second input interdigital transducer having a plurality of electrode pairs;
a second output interdigital transducer spaced a distance L from said second input interdigital transducer and mounted to said substrate, said second output interdigital transducer having a plurality of electrode pairs;
a third grating spaced the distance L from said second input interdigital transducer and mounted to said substrate;
a fourth grating spaced the distance L from said second output interdigital transducer and mounted to said substrate; and
wherein said input interdigital transducer, said output interdigital transducer, said first grating and said second grating are aligned along a first path of the acoustic waves generated by said input interdigital transducer, said second input interdigital transducer, said second output interdigital transducer, said third grating and said fourth grating are aligned along a second path of the acoustic waves generated by said second input interdigital transducer, said first path and said second path are parallel to each other, and said polymer layer further covers said second input interdigital transducer, said second output interdigital transducer, said third grating and said fourth grating.

17. A mass sensor comprising:
a support member;
a support structure on which sits said support member;
a first acoustic wave resonator and a second acoustic wave resonator, each of which includes
   a piezoelectric substrate that is a 128° YX LiNbO$_3$ crystal,
   an input interdigital transducer mounted to said substrate to receive an input electrical signal and transmit a pair of corresponding acoustic waves within said substrate, said input interdigital transducer having a plurality of electrode pairs,
   an output interdigital transducer spaced a distance L from said input interdigital transducer and mounted to said substrate to receive the acoustic waves and transmit a reference output electrical signal, said output interdigital transducer having a plurality of electrode pairs,
   a first grating spaced the distance L from said input interdigital transducer and mounted to said substrate, and
   a second grating spaced the distance L from said output interdigital transducer and mounted to said substrate;
a first connector;
a second connector;
a third connector;
a fourth connector; and
a controller electrically connected to said first connector, said second connector, said third connector, and said fourth connector, said controller is capable of transmitting an input electrical signal to said first connector and said third connector and receiving output electrical signals from said second connector and said fourth connector with the difference in frequency in the output electrical signals representing a presence of a mass; and wherein at least one of said first surface acoustic wave resonator and said second surface acoustic wave resonator further includes a well disposed over at least two of said input interdigital transducer, said output interdigital transducer, said first grating, and said second grating; and said support member is connected to said first connector, said second connector, said third connector, and said fourth connector, said support member includes lines electrically connecting the following
   said input interdigital transducer of said first surface acoustic wave resonator to said first connector,
   said output interdigital transducer of said first surface acoustic wave resonator to said second connector,
   said input interdigital transducer of said second surface acoustic wave resonator to said third connector, and
   said output interdigital transducer of said second surface acoustic wave resonator to said fourth connector; and
   wherein said distance L equals $\lambda/2$.

18. The mass sensor according to claim 17, wherein
said input interdigital transducer, said output interdigital transducer, said second input interdigital transducer, and said second output interdigital transducer of said surface acoustic wave resonator and said second acoustic wave resonator each have an identical number of electrode pairs; and said first, second, third, and fourth gratings each include at least 15 shorted reflectors.

\* \* \* \* \*